United States Patent [19]

Ligon et al.

[11] Patent Number: 5,716,849
[45] Date of Patent: Feb. 10, 1998

[54] GENES FOR THE BIOSYNTHESIS OF SORAPHEN

[75] Inventors: James M. Ligon, Apex, N.C.; Thomas Schupp, Möhlin, Switzerland; James J. Beck; Dwight S. Hill, both of Cary, N.C.; Snezana Neff, Bubendorf, Switzerland; John A. Ryals, Cary, N.C.

[73] Assignee: Novartis Finance Corporation, New York, N.Y.

[21] Appl. No.: 764,233

[22] Filed: Dec. 14, 1996

Related U.S. Application Data

[63] Continuation-in-part of PCT/US93/07954, Aug. 24, 1993, published as WO94/07954, and a continuation-in-part of Ser. No. 729,214, Oct. 9, 1995, which is a continuation-in-part of Ser. No. 258,261, Jun. 8, 1994, Pat. No. 5,639,949.

[51] Int. Cl.[6] ............................................. C12N 1/20
[52] U.S. Cl. ................. 435/419; 435/252.3; 435/252.31; 435/252.32; 435/252.33; 435/320.1; 536/23.1; 536/23.2; 536/23.7
[58] Field of Search ..................... 435/419, 252.3, 435/252.31, 252.32, 252.33, 320.1; 536/23.1, 23.2, 23.7

[56] References Cited

FOREIGN PATENT DOCUMENTS

A 0 358 606 3/1990 Germany.
WO 94/05793 3/1994 WIPO.
WO 95/33818 6/1994 WIPO.

OTHER PUBLICATIONS

Gerth et al., "The Soraphens: A Family of Novel Antifungal Compounds From *Sorangium cellulosum* (Myxobacteria)", *The Journal of Antibiotics*, 47(1):23–31 (1994).

Jaoua et al., "Transfer of Mobilizable Plasmids to *Sorangium cellosum* and Evidence for Their Integration into the Chromosome", *Plasmid*, 28: 157–165 (1992).

Schupp et al., "A *Sorangium cellulosum* (Myxobacterium) Gene Cluster for the Biosynthesis of the Macrolide Antibiotic Soraphen A: Cloning, Characterization, and Homology to Polyketide Synthase Genes from Actinomycetes", *Journal of Bacteriology*, 177 (13): 3673–3679 (1995).

*Primary Examiner*—Robert A. Wax
*Assistant Examiner*—Nashaat T. Nashed
*Attorney, Agent, or Firm*—J. Timothy Meigs

[57] ABSTRACT

The present invention is directed to the production of a polyketide antibiotic such as soraphen in a host via recombinant expression of the polypeptides needed to biologically synthesize the polyketide antibiotic. Polyketide synthase (PKS) genes encoding polypeptides necessary to synthesize soraphen are provided, along with methods for identifying and isolating the PKS genes needed to recombinantly biosynthesize any desired polyketide antibiotic. The cloned PKS genes may be transformed and expressed in a desired host organisms to produce soraphen for a variety of purposes, including protecting the host from a pathogen, developing the host as a biocontrol agent, and producing large, uniform amounts of soraphen.

29 Claims, 4 Drawing Sheets

GENES FOR THE BIOSYNTHESIS OF SORAPHEN

This is a continuation-in-part of U.S. Ser. No. 08/729, 214, filed 9 Oct. 1995, which is itself a continuation-in-part of U.S. Ser. No. 08/258,261, filed 8 Jun. 1994 (issued as U.S. Pat. No. 5,639,949 on 17 Jun. 1997). This is also a continuation-in-part of U.S. Ser. No. 08/392,731, filed as PCT/US93/07954 on 24 Aug. 1993 (published as WO 94/05793). The disclosures of each of these applications are hereby expressly incorporated in their entireties by reference into the instant disclosure.

FIELD OF THE INVENTION

The present invention relates generally to polyketides and polyketide synthases and their use in protecting organisms from pathogens. In one aspect, the invention relates to the isolation and characterization of novel polyketide synthase genes from myxobacteria of the Sorangium/Polyangium group. In another aspect, the present invention relates to methods of producing polyketides such as soraphens using recombinant DNA technology and applying such methods to the protection of plants against microbial pathogens.

BACKGROUND OF THE INVENTION

Control of Plant Diseases

Plants routinely become infected by fungi and bacteria, and many microbial species have evolved to utilize the different niches provided by the growing plant. Some phytopathogens have evolved to infect foliar surfaces and are spread through the air, from plant-to-plant contact or by various vectors, whereas other phytopathogens are soil-borne and preferentially infect roots and newly germinated seedlings. In addition to infection by fungi and bacteria, many plant diseases are caused by soil-borne nematodes that infect roots, typically causing serious damage when the same crop species is cultivated for successive years on the same area of ground.

Plant diseases cause considerable crop loss from year to year, which results both in economic hardship to farmers and nutritional deprivation for local populations in many parts of the world. The widespread use of fungicides has provided considerable security against phytopathogen attack, but despite $1 billion worth of expenditure on fungicides, worldwide crop losses amounted to approximately 10% of crop value in 1981 (James, Seed Sci. & Technol. 9: 679–685 (1981). The severity of the destructive process of disease depends on the aggressiveness of the phytopathogen and the response of the host, and one aim of most plant breeding programs is to increase the resistance of host plants to disease.

Novel gene sources and combinations developed for resistance to disease have typically only had a limited period of successful use in many crop-pathogen systems due to the rapid evolution of phytopathogens to overcome resistance genes. In addition, there are several documented cases of the evolution of fungal strains that are resistant to particular fungicides. As early as 1981, Fletcher and Wolfe (Proc. 1981 Brit. Crop Prot. Conf. (1981)) contended that 24% of the powdery mildew populations from spring barley and 53% from winter barley showed considerable variation in response to the fungicide triadimenol and that the distribution of these populations varied between barley varieties with the most susceptible variety also giving the highest incidence of less susceptible fungal types. Similar variation in the sensitivity of fungi to fungicides has been documented for wheat mildew (also to triadimenol), Botrytis (to benomyl), Pyrenophora (to organomercury), Pseudocercosporella (to MBC-type fungicides), and *Mycosphaerella fijiensis* to triazoles, to mention just a few (Jones and Clifford; Cereal Diseases, John Wiley, 1983).

Diseases caused by nematodes have also been controlled successfully by pesticide application. Whereas most fungicides are relatively harmless to mammals and the problems with their use lie in the development of resistance in target fungi, the major problem associated with the use of nematicides is their relatively high toxicity to mammals. Most nematicides used to control soil nematodes are of the carbamate, organochlorine, or organophosphorous groups and must be applied to the soil with particular care.

In some crop species, the use of biocontrol organisms has been developed as a further alternative to protect crops. Biocontrol organisms have the advantage of being able to colonize and protect parts of the plant inaccessible to conventional fungicides. This practice developed from the recognition that crops grown in some soils are naturally resistant to certain fungal phytopathogens and that the suppressive nature of these soils is lost by autoclaving. Furthermore, it was recognized that soils that are conducive to the development of certain diseases could be rendered suppressive by the addition of small quantities of soil from a suppressive field (Scher et al. Phytopathology 70: 412–417 (1980).

Subsequent research demonstrated that root colonizing bacteria were responsible for this phenomenon, now known as biological disease control (Baker et al. Biological Control of Plant Pathogens, Freeman Press, San Francisco, 1974). In many cases, the most efficient strains of biological disease controlling bacteria are of the species *Pseudomonas fluorescens* (Weller et al. Phytopathology 73: 463–469 (1983); Kloepper et al. Phytopathology 71: 1020–1024 (1981)). Important plant pathogens that have been effectively controlled by seed inoculation with these bacteria include *Gaeumannomyces graminis*, the causative agent of take-all in wheat (Cook et al. Soil Biol. Biochem 8: 269–273 (1976)) and the Pythium and Rhizoctonia phytopathogens involved in damping off of cotton (Howell et al. Phytopathology 69: 480–482 (1979)). Several biological disease controlling Pseudomonas strains produce antibiotics that inhibit the growth of fungal phytopathogens (Howell et al. Phytopathology 69: 480–482 (1979); Howell et al. Phytopathology 70: 712–715 (1980)) and these have been implicated in the control of fungal phytopathogens in the rhizosphere.

Although biocontrol was initially believed to have considerable promise as a method of widespread application for disease control, it has found application mainly in the environment of glasshouse crops where its utility in controlling soil-borne phytopathogens is best suited for success. Large scale field application of naturally occurring microorganisms has not proven possible due to constraints of microorganism production (they are often slow growing), distribution (they are often short lived), and cost (the result of both these problems). In addition, the success of biocontrol approaches is also largely limited by the identification of naturally occurring strains which may have a limited spectrum of efficacy.

Some initial approaches have also been taken to control nematode phytopathogens using biocontrol organisms. Although these approaches are still exploratory, some Streptomyces species have been reported to control the root knot nematode (*Meloidogyne spp.*) (WO 93/118135 to Research Corporation Technology), and toxins from some *Bacillus thuringiensis* strains (such as *israeliensis*) have been shown to have broad anti-nematode activity and spore or bacillus preparations may thus provide suitable biocontrol opportunities (EP 0 352 052 to Mycogen, WO 93/19604 to Research Corporation Technologies).

Polyketide Antibiotics

Many antibiotics, in spite of the apparent structural diversity, share a common pattern of biosynthesis. The molecules are built up from two carbon building bloc, the β-carbon of which always carries a keto group, thus the name polyketide. Polyketides include many important antibiotics, immunosuppressants, and other compounds possessing a broad range of biological properties.

The tremendous structural diversity derives from the different lengths of the polyketide chain and the different side-chains introduced, either as part of the two carbon building blocks, or after the polyketide backbone is formed. The keto groups may also be reduced to hydroxyls or removed altogether. Each round of two carbon addition is carded out by a complex of enzymes called the polyketide synthases (PKS) in a manner similar to fatty acid biosynthesis.

The biosynthetic genes for an increasing number of polyketide antibiotics have been isolated and sequenced. It is quite apparent that the PKS genes are structurally conserved. The encoded proteins generally fall into two types: type I proteins are polyfunctional, with several catalytic domains carrying out different enzymatic steps covalently linked together (e.g. PKS for erythromycin, soraphen, and avermectin (Joaua et al. Plasmid 28: 157–165 (1992); MacNeil et al. in: Industrial Microorganisms: Basic and Applied Molecular Genetics, (ed.: Baltz et al.), American Society for Microbiology, Washington D.C. pp. 245–256 (1993)); whereas type II proteins are monofunctional (Hutchinson et al. in: Industrial Microorganisms: Basic and Applied Molecular Genetics, (ed.: Baltz et al.), American Society for Microbiology, Washington D.C. pp. 203–216 (1993)).

For the simpler polyketide antibiotics such as actinorhodin (produced by *Streptomyces coelicolor*), the several rounds of two carbon additions are carried out iteratively on PKS enzymes encoded by one set of PKS genes. In contrast, synthesis of the more complicated compounds such as erythromycin and soraphen involves sets of PKS genes organized into modules, with each module carrying out one round of two-carbon addition (for review see Hopwood et al. in: Industrial Microorganisms: Basic and Applied Molecular Genetics, (ed.: Baltz et al.), American Society for Microbiology, Washington D.C. pp. 267–275 (1993)).

Soraphen-Producing Myxobacteria

The myxobacteria of the Sorangium/Polyangium group are highly specialized organisms that are frequently detectable in soil samples, dead plant material, or in animal dung. Characteristic of this group of microorganisms is, inter alia, their ability to utilize cellulose or cellulose-containing degradation products as sole carbon source. Another characteristic feature of this group is their ability to produce highly active secondary metabolites such as soraphens.

To date, numerous strains of this group of organisms that are able to synthesize plant-microbicidal compounds have been described. Of particular importance in this connection are the so-called soraphens, the structural particulars of which are described, for example, in EP0358606 and in Schupp et al., Journal of Bacteriology 177: 3673–3679 (1995), both of which are hereby incorporated by reference in their entireties. The soraphens are polyketides that have a cytostatic activity and a favorable biocidal spectrum against pathogenic microorganisms, but especially against phytopathogenic fungi. These compounds have very advantageous curative, systemic and, in particular, preventive properties and are therefore ideal for the therapeutic treatment of mammalians and protecting numerous crop plants.

One object of this invention relates to the cloning of the PKS genes that are involved in the synthesis of soraphens, particularly the genes that are involved in the synthesis of soraphen in myxobacteria of the Sorangium/Polyangium group, i.e., *Sorangium cellulosum*. It is known from earlier investigations on actinomycetes, for example, that genes involved in the individual steps of secondary metabolite biosynthesis are usually organized in the form of gene clusters on the bacterial chromosome. A number of procedures have been proposed for isolating genes whose products are involved indirectly or directly in polyketide antibiotic biosynthesis. These include, for example, complementation methods in which the biosynthetic ability of defective mutants that, because of a specific mutation, are no longer able to synthesize the required antibiotic is restored with the aid of fragments obtained from wild-type DNA [see, for example, Malpartida and Hopwood, 1984].

Another method for finding genes involved in the biosynthesis of polyketide antibiotics is described in WO87/03907, hereby incorporated by reference in its entirety. This entails using a DNA fragment that comprises at least one part of a gene, which is involved in the biosynthesis of a known polyketide antibiotic, as a DNA hybridization probe for screening a genomic gene bank that has previously been prepared from the genomic DNA of the subject microorganism.

Although the principal techniques for the identification and isolation of such gene clusters are known, the applicability thereof to an organism group that has been but little investigated to date is problematic because of the uncertainties involved. This is particularly true when, as in the present case, there is no information available about the structural organization of the genome. Therefore, in the search for the gene cluster responsible for polyketide biosynthesis, it is first necessary to find a suitable starting point for the necessary genome analysis. This is also the reason why the relatively modest information concerning the genetic structuring of polyketide biosynthesis is to date concentrated on a few well-investigated organism groups, while next to nothing is known for others such as the myxobacteria.

In addition, although traditional methods of protecting crops against disease, including plant breeding for disease resistance, the continued development of fungicides, and more recently, the identification of biocontrol organisms, have all met with success, it is apparent that scientists must constantly be in search of new methods with which to protect crops against disease. Therefore, in addition to the aforementioned object of cloning the polyketide synthase genes involved in soraphen biosynthesis, another object of the invention is to use these genes to create transgenic plants with enhanced disease resistance characteristics and to also create improved biocontrol strains by expression of the isolated genes in organisms that colonize host plants or the rhizosphere. Furthermore, the availability of such genes provides methods for the production of soraphen for isolation and application in antipathogenic formulations.

SUMMARY OF THE INVENTION

In a preferred embodiment, the present invention provides an isolated DNA molecule encoding at least one polypeptide necessary for the biosynthesis of soraphen. In an especially preferred embodiment, the present invention provides an isolated DNA molecule comprising the minimal polyketide synthase (PKS) genes that are required for the biosynthesis of soraphen. The present invention additionally relates to chimeric DNA molecules that comprise one of the DNA molecules of the invention, and to plasmids and vectors derived that comprise one of the DNA molecules of the invention.

The invention further provides methods for the manipulation of PKS genes, i.e., soraphen biosynthetic genes, for their expression in transgenic plants. The transgenic plants thus modified have enhanced resistance to attack by phytopathogens. Further provided are methods for the enhancement of throughput through the soraphen biosynthetic pathway by overexpression and overproduction of genes encoding substrate precursors.

The invention further provides a novel method for the identification and isolation of the genes involved in the biosynthesis of a polyketide such as soraphen in a host organism.

The invention also describes the heterologous production of a polyketide such as soraphen in improved biocontrol strains that are efficacious in controlling microbial pathogens outside the usual range of the host.

Thus, the invention provides methods for disease control. These methods involve the use of transgenic plants expressing PKS genes such as soraphen biosynthetic genes in addition to the use of biocontrol agents expressing PKS genes such as soraphen genes to control pathogens in the plant itself and in the environment in which the plant grows.

The invention further provides methods for the production of polyketides such as soraphen in quantities large enough to enable their isolation and use in agricultural formulations. A specific advantage of these production methods is the chirality of the molecules produced; production in transgenic organisms avoids the generation of populations of racemic mixtures, within which some enantiomers may have reduced activity.

DETAILED DESCRIPTION OF THE INVENTION

Definitions

Figure 1:
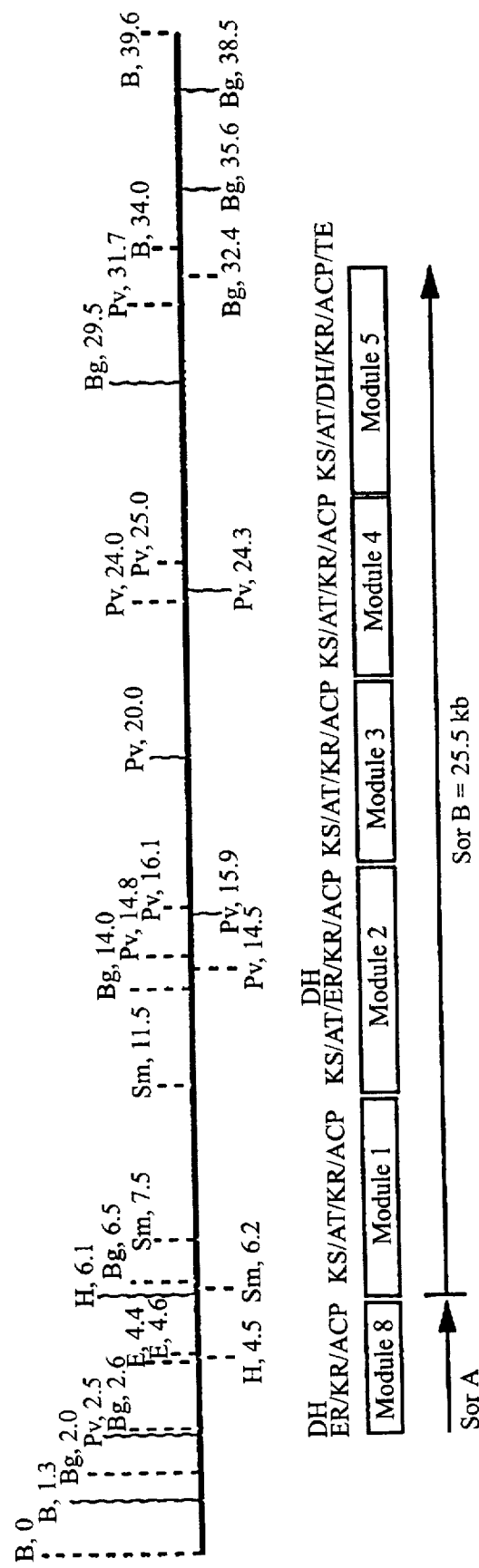
FIG. 1 shows a restriction map of the cosmid clone p98/1 from *Sorangium cellulosum* carrying a portion of the soraphen biosynthetic gene region. The top line depicts the restriction map of p98/1 and shows the position of restriction sites and their distance from the left edge in kilobases. Restriction sites shown include: B, BamHI; Bg BglII; E, EcoRI; H, HindIII; Pv, PvuI; Sm, SmaI. The boxes below the restriction map depict the location of the biosynthetic modules. The activity domains within each module are designated as follows: β-ketoacylsynthase (KS), Acyltransferase (AT), Ketoreductase (KR), Acyl Carder Protein (ACP), Dehydratase (DH), Enoyl reductase (ER), and Thioesterase (TE).

In describing the present invention, the following terms will be employed, and are intended to be defined as indicated below.

PKS: A polyketide synthase, which is a complex of enzymatic activities responsible for the biosynthesis of polyketides including, but are not limited, to ketoreductase, dehydratase, acyl carrier protein, enoylreductase, ketoacyl ACP synthase, and acyltransferase. A functional PKS is one that catalyzes the synthesis of a polyketide.

PKS genes: One or more genes encoding various proteins required for producing a functional polyketide, i.e., soraphen, when under the direction of one or more compatible control elements. For example, soraphen is the product of all the genes in the PKS gene pathway.

Minimal PKS genes: Genes that code for only the necessary PKS components to catalyze, the production of the core structure of the polyketide. As reported, a gene cluster need not correspond to the complete native genes but need only encode the necessary PKS components to catalyze the production of a polyketide. For example, in soraphen, carbon chain assembly requires the products of two ORFs: SorA and SorB. Thus, in the case of soraphen, these two ORFs, without other components, constitute a "minimal" PKS gene.

Modified PKS genes: One or more mutant or analog genes that differ from the native genes but that still encode various proteins required for producing a functional polyketide. The mutants or analogs may be prepared by deletion, insertion, or substitution of one or more nucleotides of the coding sequence.

Altered PKS enzyme activity: A PKS enzymatic activity different from that which occurs in normal quantities in Sorangium (i.e. PKS activity that occurs normally in the absence of direct or indirect manipulation of such activity by man). This is caused by changes in a portion of the DNA sequence, which results in an altered polyketide structure or altered distribution of polyketide derivatives. Altered PKS enzyme activity may be conferred upon a host according to the invention by increasing expression of wild-type or modified PKS.

Soraphen: A class of polyketides having a common core structure comprising a 17-carbon ring as described in Donadio et al., Science 252: 675–679 (1991). In this application, this class of polyketide compounds is collectively referred to as "soraphen".

DNA fragment: A piece of DNA that may comprise both coding and non-coding sections and that either can be obtained directly from a natural source or else can be prepared with the aid of recombinant or synthetic techniques or else a combination of said techniques.

Coding DNA sequence: A DNA sequence composed of individual nucleotide constituents in accordance with the rules of the genetic code, which comprises structural information and that, after transcription and translation have taken place, results in the production of a corresponding polypeptide.

Gene: A defined region that is located within a genome and that, besides the aforementioned coding DNA sequence, comprises other, primarily regulatory, DNA sequences responsible for the control of the expression, that is to say the transcription and translation, of the coding portion.

Essentially homologous: This term relates primarily to DNA and amino acid sequences that must, because of the homologies present, be regarded as structural and/or functional equivalents. The structural and/or functional differences between the relevant sequences, which should as a rule be minimal, can have very different causes. Thus, for example, these may comprise mutations which occur naturally or else are induced artificially, or else the differences to be observed compared with the initial sequence are based on a specific modification which can be introduced, for example, within the scope of a chemical synthesis. Functional differences can be regarded as minimal when, for example, the nucleotide sequence coding for a polypeptide, or a protein sequence, has essentially the same characteristic properties as the initial sequence, within the area of enzymatic activity, of immunological reactivity or, in the case of a nucleotide sequence, of gene regulation. Structural differences can be regarded as significant mininimal as long there is a significant overlap or similarity between the different sequences, or the latter have at least similar physical properties. The latter include, for example, the electrophoretic mobility, chromatographic similarities, sedimentation coefficients, spectrophotometric properties, etc. In the case of the nucleotide sequences, the agreement should be at least 60%, but preferably 75% and, very particularly preferably, 90% and more. In the case of the amino acid sequence, the corresponding values are at least 70%, but preferably 80% and, particularly preferably, 90%. A 99% agreement is very particularly preferred.

Gene(s) or DNA of heterologous origin: A DNA sequence that codes for a specific product or products or fulfills a biological function and that originates from a different species than that into which the gene is inserted; said DNA sequence is also called foreign gene or foreign DNA or exogenous DNA.

Gene(s) or DNA of homologous origin: A DNA sequence that codes for a specific product or products or fulfills a biological function and that originates from the same species into which the gene is inserted. This DNA is also called exogenous DNA.

DNA homology: Degree of agreement between two or more DNA sequences.

Synthetic gene(s) or DNA: A DNA sequence that codes for a specific product or products or fulfills a biological function and that is prepared by a synthetic route.

Termination sequence: DNA sequence at the end of a transcription unit that signals the end of the transcription process.

Overproducing promoter (OPP): Promoter that is able in a host cell to bring about the expression of any functional gene sequence(s) linked in an operable manner to an extent (measured in the form of the RNA or of the amount of polypeptide) that is distinctly higher than is naturally observed in host cells not transformed with said OPP.

3'/5' non-translated region: DNA sections which are located downstream/upstream of the coding region and that, although transcribed into mRNA, are not translated into a polypeptide. This region comprises regulatory sequences such as, for example, the ribosome binding site (5').

DNA expression vector: Cloning vehicle, such as, for example, a plasmid or a bacteriophage, which comprises all signal sequences that are necessary for expression of an inserted DNA in a suitable host cell.

DNA transfer vector: Transfer vehicle, such as, for example, a plasmid or a bacteriophage vector, which makes it possible to insert genetic material into a suitable host cell.

Homologous recombination: Reciprocal exchange of DNA fragments between homologous DNA molecules.

Mutants, variants: Derivative, produced spontaneously or else artificially using known process measures such as, for example, UV treatment, treatment with mutagenic agents etc., of a microorganism, which still has the features and properties, essential to the invention, of the initial strain which this has received because of the transformation with exogenous DNA.

Biocontrol agent: An organism that is capable of affecting the growth of a pathogen such that the ability of the pathogen to cause a disease is reduced. Biocontrol agents for plants include microorganisms which are capable of colonizing plants or the rhizosphere. Such biocontrol agents include gram-negative microorganisms such as Pseudomonas, Enterobacter and Serratia, the gram-positive microorganism Bacillus and the fungi Trichoderrna and Gliocladium. Organisms may act as biocontrol agents in their native state or when they are genetically engineered according to the invention.

Pathogen: Any organism that causes a deleterious effect on a selected host under appropriate conditions. Within the scope of this invention the term pathogen is intended to include fungi, bacteria, nematodes, viruses, viroids and insects. Promoter or Regulatory DNA Sequence: An untranslated DNA sequence that assists in, enhances, or otherwise affects the transcription, translation or expression of an associated structural DNA sequence which codes for a protein or other DNA product. The promoter DNA sequence is usually located at the 5' end of a translated DNA sequence, typically between 20 and 100 nucleotides from the 5' end of the translation start site.

Operably Linked to/Associated With: Two DNA sequences that are "associated" or "operably linked" are related physically or functionally. For example, a promoter or regulatory DNA sequence is said to be "associated with" a DNA sequence that codes for an RNA or a protein if the two sequences are operably linked, or situated such that the regulator DNA sequence will affect the expression level of the coding or structural DNA sequence.

Chimeric Construction/Fusion DNA Sequence: A recombinant DNA sequence in which a promoter or regulatory DNA sequence is operably linked to, or associated with, a DNA sequence that cedes for an mRNA or which is expressed as a protein, such that the regulator DNA sequence is able to regulate transcription or expression of the associated DNA sequence. The regulator DNA sequence of the chimeric construction is not normally operably linked to the associated DNA sequence as found in nature. The terms "heterologous" or "non-cognate" are used to indicate a recombinant DNA sequence in which the promoter or regulator DNA sequence and the associated DNA sequence are isolated from organisms of different species or genera.

Methods for Cloning PKS Genes

PKS genes such as involved in the biosynthesis of soraphen can be cloned using a variety of techniques according to the invention. The simplest procedure for the cloning of PKS genes requires the cloning of genomic DNA from an organism identified as producing a polyketide antibiotic such as soraphen, and the transfer of the cloned DNA on a suitable plasmid or vector to a host organism which does not produce the polyketide, followed by the identification of transformed host colonies to which the polyketide, i.e., soraphen-producing ability has been conferred. Using a technique such as λ::Tn5 transposon mutagenesis (de Bruijn & Lupski, Gene 27: 131–149 (1984)), the exact region of the transforming polyketide antibiotic-conferring DNA can be more precisely defined. Alternatively or additionally, the transforming polyketide antibiotic-conferring DNA can be cleaved into smaller fragments and the smallest which maintains the polyketide antibiotic-conferring ability further characterized. Whereas the host organism lacking the ability to produce the polyketide antibiotic may be a different species to the organism from which the polyketide antibiotic derives, a variation of this technique involves the transformation of host DNA into the same host which has had its polyketide antibiotic-producing ability disrupted by mutagenesis. In this method, an polyketide antibiotic-producing organism is mutated and non-polyketide antibiotic producing mutants isolated, and these are complemented by cloned genomic DNA from the polyketide antibiotic producing parent strain. A further example of a standard technique used to clone genes required for polyketide antibiotic biosynthesis is the use of transposon mutagenesis to generate mutants of an polyketide antibiotic-producing organism which, after mutagenesis, fail to produce the polyketide antibiotic. Thus, the region of the host genome responsible for polyketide antibiotic production is tagged by the transposon and can be easily recovered and used as a probe to isolate the native genes from the parent strain. PKS genes which are required for the synthesis of polyketide antibiotics and which are similar to known PKS genes may be clonable by virtue of their sequence homology to the biosynthetic genes of the known polyketide antibiotics. Techniques suitable for cloning by homology include standard library screening by DNA hybridization.

Preferred for use as probe molecule within the scope of the present invention is a DNA fragment which can be obtained from a gene or another DNA sequence which plays a part in the synthesis of a known polyketide antibiotic. A particularly preferred probe molecule is a 4.6 Kb BamHI fragment from the graI region of the granaticin gene cluster [ORF 1-4] of Streptomyces violaceoruber Tü22 [Sherman Det at, 1989], which can be used to probe a gene library of a soraphen-producing microorganism to isolate the PKS genes responsible for soraphen biosynthesis.

This invention also describes a novel technique for the isolation of PKS genes which may be used to clone the genes for any polyketide antibiotic, and is particularly useful for the cloning of PKS genes which may be recalcitrant to cloning using any of the above techniques. One reason why such recalcitrance to cloning may exist is that the standard techniques described above (except for cloning by homology) may preferentially lead to the isolation of regulators of polyketide antibiotic biosynthesis. Once such a regulator has been identified, however, it can be used using this novel method to isolate the biosynthetic genes under the control of the cloned regulator. In this method, a library of transposon insertion mutants is created in a strain of microorganism which lacks the regulator or has had the regulator gene disabled by conventional gene disruption techniques. The insertion transposon used carries a promoter-less reporter gene (e.g. lacZ). Once the insertion library has been made, a functional copy of the regulator gene is transferred to the library of cells (e.g. by conjugation or electroporation) and the plated cells are selected for expression of the reporter gene. Cells are assayed before and after transfer of the regulator gene. Colonies which express the reporter gene only in the presence of the regulator gene are insertions adjacent to the promoter of genes regulated by the regulator. Assuming the regulator is specific in its regulation for PKS genes, then the genes tagged by this procedure will be PKS genes.

In order for the cloned PKS genes, i.e. genes involved in soraphen biosynthesis, to be of use in transgenic expression, it is important that all the genes required for synthesis from a particular metabolite be identified and cloned. Using combinations of, or all the techniques described above, this is possible for any known polyketide antibiotic. As most PKS genes are clustered together in microorganisms, usually encoded by a single operon, the identification of all the genes will be possible from the identification of a single locus in an polyketide antibiotic-producing microorganism. In addition, as regulators of PKS genes are believed to regulate the whole pathway, then the cloning of the biosynthetic genes via their regulators is a particularly attractive method of cloning these genes. In many eases the regulator will control transcription of the single entire operon, thus facilitating the cloning of genes using this strategy.

Using the methods described in this application, biosynthetic genes for any polyketide antibiotic can be cloned from a microorganism that produces that polyketide antibiotic, and using the methods of gene manipulation and transgenic plant production described in this specification, the cloned PKS genes can be modified and expressed in transgenic plants. Especially suitable PKS genes include those that are involved in the biosynthesis of soraphen. Expression in transgenic plants will be under the control of an appropriate promoter and involves appropriate cellular targeting considering the likely precursors required for the particular polyketide antibiotic under consideration. Whereas the invention is intended to include the expression in transgenic plants of any PKS gene isolatable by the procedures described in this specification, those which are particularly preferred include soraphen biosynthetic genes. The cloned biosynthetic genes can also be expressed in soil-borne or plant colonizing organisms for the purpose of conferring and enhancing biocontrol efficacy in these organisms. Particularly preferred PKS genes for this purpose are those which encode polypeptides required for soraphen biosynthesis.

Production of Polyketide Antibiotics in Heterologous Microbial Hosts

Cloned PKS genes, i.e., soraphen biosynthetic genes, can be expressed in heterologous bacterial or fungal hosts to enable the production of the polyketide antibiotic with greater efficiency than might be possible from native hosts. Techniques for these genetic manipulations are specific for the different available hosts and are known in the art. For example, the expression vectors pKK223-3 and pKK223-2 can be used to express heterologous genes in E. coli, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as Bacillus are also known in the art and can be used in the context of this invention (Quax et al. In.: Industrial Microorganisms: Basic and Applied Molecular Genetics, Eds. Baltz et al., American Society for Microbiology, Washington (1993)). Alternate systems for overexpression rely on yeast vectors and include the use of Pichia, Saccharomyces and Kluyveromyces (Sreekrishna, In: Industrial microorganisms: basic and applied molecular genetics, Baltz, Hegeman, and Skatrud eds., American Society for Microbiology, Washington (1993); Dequin & Barre, Biotechnology 12: 173–177 (1994); van den Berg et al., Biotechnology 8: 135–139 (1990)).

Cloned PKS genes can also be expressed in heterologous bacterial and fungal hosts with the aim of increasing the efficacy of biocontrol strains of such bacterial and fungal hosts. Microorganisms which are suitable for the heterologous overexpression of PKS genes are all microorganisms which are capable of colonizing plants or the rhizosphere. As such they will be brought into contact with phytopathogenic fungi, bacteria and nematodes causing an inhibition of their growth. These include gram-negative microorganisms such as Pseudomonas, Enterobacter and Serratia, the gram-positive microorganism Bacillus and the fungi Trichoderma and Gliocladium. Particularly preferred heterologous hosts are *Pseudomonas fluorescens, Pseudomonas putida, Pseudomonas cepacia, Pseudomonas aureofaciens, Pseudomonas aurantiaca, Enterobacter cloacae, Serratia marscesens, Bacillus subtilis, Bacillus cereus, Trichoderma viride, Trichoderma harzianum* and *Gliocladium virens*. In a preferred embodiment of the invention, the biosynthetic genes for soraphen are transferred to the particularly preferred heterologous hosts listed above. In a particularly preferred embodiment, the biosynthetic genes for soraphen are transferred to and expressed in *Pseudomonas fluorescens* strain CGA267356 (described in the published applications EU 0 472 494 and in WO 94/01561 as well as in U.S. Pat. No. 5,348,742, all of which are hereby incorporated by reference in their entireties), which has biocontrol utility due to its production of pyrrolnitrin. In another preferred embodiment, the biosynthetic genes for soraphen are transferred to *Pseudomonas aureofaciens* strain 30–84, which has biocontrol characteristics due to its production of phenazine. Expression in heterologous biocontrol strains requires the selection of vectors appropriate for replication in the chosen host and a suitable choice of promoter. Techniques are well known in the art for expression in gram-negative and gram-positive bacteria and fungi and are described elsewhere in this specification.

Expression of PKS Genes in Plants

The PKS genes of this invention are expressed in transgenic plants thus causing the biosynthesis of the selected polyketide antibiotic such as soraphen in the transgenic plants. In this way, transgenic plants with enhanced resistance to phytopathogenic fungi, bacteria and nematodes are generated. For their expression in transgenic plants, however, the PKS genes and adjacent sequences may require modification and optimization.

Although in many cases genes from microbial organisms can be expressed in plants at high levels without modification, low expression in transgenic plants may result from PKS genes having codons which are not preferred in plants. It is known in the art that all organisms have specific preferences for codon usage, and the PKS gene codons can be changed to conform with plant preferences, while maintaining the amino acids encoded. Furthermore, high expression in plants is best achieved from coding sequences which have at least 35% GC content, and preferably more than 45%. Microbial genes which have low GC contents may express poorly in plants due to the existence of ATTTA motifs which may destabilize messages, and AATAAA motifs which may cause inappropriate polyadenylation. In addition, potential PKS genes can be screened for the existence of illegitimate splice sites which may cause message truncation. All changes required to be made within the PKS gene coding sequence such as those described above can be made using well known techniques of site directed mutagenesis, PCR, and synthetic gene construction using the methods described in the published patent applications EP 0 385 962 (to Monsanto), EP 0 359 472 (to Lubrizol, and WO 93/07278 (to Ciba-Geigy). The preferred PKS genes may be unmodified genes, should these be expressed at high levels in target transgenic plant species, or alternatively may be genes modified by the removal of destabilization and inappropriate polyadenylation motifs and illegitimate splice sites, and further modified by the incorporation of plant preferred codons, and further with a GC content preferred for expression in plants. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17: 477–498 (1989)).

For efficient initiation of translation, sequences adjacent to the initiating methionine may require modification. The sequences cognate to the selected PKS genes may initiate translation efficiently in plants, or alternatively may do so inefficiently. In the case that they do so inefficiently, they can be modified by the inclusion of sequences known to be effective in plants. Joshi has suggested an appropriate consensus for plants (NAR 15: 6643–6653 (1987) (SEQ ID NO:2)) and Clontech suggests a further consensus translation initiator (1993/1994 catalog, page 210; (SEQ ID NO:3) ). These consensuses are suitable for use with the PKS genes of this invention, including the soraphen biosynthetic genes. The sequences are incorporated into the PKS gene construction, up to and including the ATG (whilst leaving the second amino acid of the PKS gene unmodified), or alternatively up to and including the GTC subsequent to the ATG (with the possibility of modifying the second amino acid of the transgene).

Expression of PKS genes in transgenic plants is behind a promoter shown to be functional in plants. The choice of promoter will vary depending on the temporal and spatial requirements for expression, and also depending on the target species. For the protection of plants against foliar pathogens, expression in leaves is preferred; for the protection of plants against ear pathogens, expression in inflorescences (e.g. spikes, particles, cobs etc.) is preferred; for protection of plants against root pathogens, expression in roots is preferred; for protection of seedlings against soil-borne pathogens, expression in roots and/or seedlings is preferred. In many cases, however, protection against more than one type of phytopathogen will be sought, and thus expression in multiple tissues will be desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenante of selected promoters; it is sufficient that they are operational in driving the expression of the PKS genes.

Preferred promoters which are expressed constitutively include the CaMV 35S and 19S promoters, and promoters from genes encoding actin or ubiquitin. Further preferred constitutive promoters are those from the 12(4–28), CP21, CP24, CP38, and CP29 genes.

The PKS genes of this invention can also be expressed under the regulation of promoters which are chemically regulated. This enables the polyketide antibiotic to be synthesized only when the crop plants are treated with the inducing chemicals, and polyketide antibiotic biosynthesis subsequently declines. Preferred technology for chemical induction of gene expression is detailed in the published application EP 0 332 104 (to Ciba-Geigy) and application Ser. No. 08/181,271—now U.S. Pat. No. 5,614,395 (hereby incorporated herein by reference). A preferred promoter for chemical induction is the tobacco PR-1a promoter.

A preferred category of promoters is that which is wound inducible. Numerous promoters have been described which are expressed at wound sites and also at the sites of phytopathogen infection. These are suitable for the expression of PKS genes because polyketide antibiotic biosynthesis is turned on by phytopathogen infection and thus the polyketide only accumulates when infection occurs. Ideally, such a promoter should only be active locally at the sites of infection, and in this way polyketide antibiotic only accumulates in cells which need to synthesize the polyketide to kill the invading phytopathogen. Preferred promoters of this kind include those described by Stanford et al. Mol. Gem Genet. 215: 200–208 (1989), Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993) and Warner et al. Plant J. 3: 191–201 (1993).

Preferred tissue specific expression patterns include green tissue specific, root specific, stem specific, and flower specific. Promoters suitable for expression in green tissue include many which regulate genes involved in photosynthesis and many of these have been cloned from both monocotyledons and dicotyledons. A preferred promoter is the maize PEPC promoter from the phosphoenol carboxylase gene (Hudspeth & Grula, Plant Molec. Biol. 12: 579–589 (1989)). A preferred promoter for root specific expression is that described by de Framond (FEBS 290: 103–106 (1991); EP 0 452 269 to Ciba-Geigy) and a further preferred root-specific promoter is that from the T-1 gene provided by this invention. A preferred stem specific promoter is that described in patent application WO 93/07278 (to Ciba-Geigy) and which drives expression of the maize trpA gene.

Preferred embodiments of the invention are transgenic plants expressing PKS genes in a root-specific fashion. An especially preferred embodiment of the invention involves the expression of the biosynthetic genes for soraphen behind a wound-inducible or pathogen-inducible promoter for the control of foliar pathogens.

In addition to the selection of a suitable promoter, constructions for polyketide antibiotic expression in plants require an appropriate transcription terminator to be attached downstream of the heterologous PKS gene. Several such terminators are available and known in the art (e.g. tml from CaMV, E9 from rbcS). Any available terminator known to function in plants can be used in the context of this invention.

Numerous other sequences can be incorporated into expression cassettes for PKS genes. These include sequences which have been shown to enhance expression such as intron sequences (e.g. from Adh1 and bronze1) and viral leader sequences (e.g. from TMV, MCMV and AMV).

The overproduction of polyketide antibiotics in plants requires that the PKS gene encoding the first step in the pathway will have access to the pathway substrate. For each individual polyketide antibiotic and pathway involved, this substrate will likely differ, and so too may its cellular localization in the plant. In many cases the substrate may be localized in the cytosol, whereas in other cases it may be localized in some subcellular organelle. As much biosynthetic activity in the plant occurs in the chloroplast, often the substrate may be localized to the chloroplast and consequently the PKS gene products for such a pathway are best targeted to the appropriate organelle (e.g. the chloroplast). Subcellular localization of transgene encoded enzymes can be undertaken using techniques well known in the art. Typically, the DNA encoding the target peptide from a known organelle-targeted gene product is manipulated and fused upstream of the required PKS gene/s. Many such target sequence are known for the chloroplast and their functioning in heterologous constructions has been shown.

In some situations, the overexpression of PKS gene may deplete the cellular availability of the substrate for a particular pathway and this may have detrimental effects on the cell. In situations such as this it is desirable to increase the amount of substrate available by the overexpression of genes which encode the enzymes for the biosynthesis of the substrate. A further way of making more substrate available is by the turning off of known pathways which utilize specific substrates (provided this can be done without detrimental side effects). In this manner, the substrate synthesized is channeled towards the biosynthesis of the polyketide antibiotic and not towards other compounds.

Vectors suitable for plant transformation are described elsewhere in this specification. For Agrobacterium-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Sohocher et al. Biotechnology 4: 1093–1096 (1986)). For both direct gene transfer and Agrobacterium-mediated transfer, transformation is usually (but not necessarily) undertaken with a selectable marker which may provide resistance to an antibiotic (kanamycin, hygromycin or methatrexate) or a herbicide (basta). The choice of selectable marker is not, however, critical to the invention.

Synthesis of a polyketide antibiotic such as soraphen in a transgenic plant will frequently require the simultaneous overexpression of multiple genes encoding the polyketide antibiotic biosynthetic enzymes. This can be achieved by transforming the individual PKS genes into different plant lines individually, and then crossing the resultant lines. Selection and maintenance of lines carrying multiple genes is facilitated if each the various transformation constructions utilize different selectable markers. A line in which all the required PKS genes have been pyramided will synthesize the polyketide antibiotic, whereas other lines will not. This approach may be suitable for hybrid crops such as maize in which the final hybrid is necessarily a cross between two parents. The maintenance of different inbred lines with different PKS genes may also be advantageous in situations where a particular polyketide antibiotic pathway may lead to multiple polyketide products, each of which has a utility. By utilizing different lines carrying different alternative genes for later steps in the pathway to make a hybrid cross with lines carrying all the remaining required genes it is possible to generate different hybrids carrying different selected polyketide antibiotics which may have different utilities.

Alternate methods of producing plant lines carrying multiple genes include the retransformation of existing lines already transformed with a PKS gene or genes (and selection with a different marker), and also the use of single transformation vectors which carry multiple PKS genes, each under appropriate regulatory control (i.e. promoter, terminator etc.). Given the ease of DNA construction, the manipulation of cloning vectors to carry multiple PKS genes is a preferred method.

Production of Polyketide Antibiotics in Heterologous Hosts

The present invention also provides methods for obtaining polyketide antibiotics such as soraphen from heterologous hosts transformed with the appropriate PKS gene. These polyketide antibiotics may be effective in the inhibition of growth of microbes, particularly phytopathogenic microbes. The polyketide antibiotics can be produced from organisms in which the PKS genes have been overexpressed, and suitable organisms for this include gram-negative and gram-positive bacteria and yeast, as well as plants. For the purposes of polyketide antibiotic production, the significant criteria in the choice of host organism are its ease of manipulation, rapidity of growth (i.e. fermentation in the case of microorganisms), and its lack of susceptibility to the polyketide antibiotic being overproduced. These methods of polyketide antibiotic production have significant advantages over the chemical synthesis technology usually used in the preparation of antibiotics. These advantages are the cheaper cost of production, and the ability to synthesize compounds of a preferred biological enantiomer, as opposed to the racemic mixtures inevitably generated by organic synthesis. The ability to produce stereochemically appropriate compounds is particularly important for molecules with many chirally active carbon atoms. Polyketide antibiotics produced by heterologous hosts can be used in medical (i.e. control of pathogens and/or infectious disease) as well as agricultural applications.

Formulation of Antipathogenic Compositions

The present invention further embraces the preparation of antifungal compositions in which the active ingredient is the polyketide antibiotic produced by the recombinant biocontrol agent of the present invention or alternatively a suspension or concentrate of the microorganism. The active ingredient is homogeneously mixed with one or more compounds or groups of compounds described herein. The present invention also relates to methods of treating plants, which comprise application of the active ingredient, or antifungal compositions containing the active ingredient, to plants.

The active ingredients of the present invention are normally applied in the form of compositions and can be applied to the crop area or plant to be treated, simultaneously or in succession, with further compounds. These compounds can be both fertilizers or micronutrient donors or other preparations that influence plant growth. They can also be selective herbicides, insecticides, fungicides, bactericides, nematicides, molluscicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

A preferred method of applying active ingredients of the present invention or an agrochemical composition which contains at least one of the active ingredients is leaf application. The number of applications and the rate of application depend on the intensity of infestation by the corresponding phytopathogen (type of fungus). However, the active ingredients can also penetrate the plant through the roots via the soil (systemic action) by impregnating the locus of the plant with a liquid composition, or by applying the compounds in solid form to the soil, e.g. in granular form (soil application). The active ingredients may also be applied to seeds (coating) by impregnating the seeds either with a liquid formulation containing active ingredients, or coating them with a solid formulation. In special cases, further types of application are also possible, for example, selective treatment of the plant stems or buds.

The active ingredients are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations, for example, in polymer substances. Like the nature of the compositions, the methods of application, such as spraying, atomizing, dusting, scattering or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 500 g a.i./ha.

The formulations, compositions or preparations containing the active ingredients and, where appropriate, a solid or liquid adjuvant, are prepared in known manner, for example by homogeneously mixing and/or grinding the active ingredients with extenders, for example solvents, solid carriers and, where appropriate, surface-active compounds (surfactants).

Suitable solvents include aromatic hydrocarbons, preferably the fractions having 8 to 12 carbon atoms, for example, xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidized vegetable oils such as epoxidized coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverized plant residues.

Depending on the nature of the active ingredient to be used in the formulation, suitable surface-active compounds are nonionic, cationic and/or anionic surfactants having good emulsifying, dispersing and wetting properties. The term "surfactants" will also be understood as comprising mixtures of surfactants.

Suitable anionic suffactants can be both water-soluble soaps and water-soluble synthetic surface-active compounds.

Suitable soaps are the alkali metal salts, alkaline earth metal salts or unsubstituted or substituted ammonium salts of higher fatty acids (chains of 10 to 22 carbon atoms), for example the sodium or potassium salts of oleic or stearic acid, or of natural fatty acid mixtures which can be obtained for example from coconut oil or tallow oil. The fatty acid methyltaurin salts may also be used.

More frequently, however, so-called synthetic suffactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and have a 8 to 22 carbon alkyl radical which also includes the alkyl moiety of alkyl radicals, for example, the sodium or calcium salt of lignonsulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnapthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic suffactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic suffactants.

Cationic suffactants are preferably quaternary ammonium salts which have, as N-substituent, at least one C8–C22 alkyl radical and, as further substituents, lower unsubstituted or halogenated alkyl, benzyl or lower hydroxyalkyl radicals. The salts are preferably in the form of halides, methylsulfates or ethylsulfates, e.g. Stearyl trimethylammonium chloride or benzyldi(2-chloroethyl)ethylammonium bromide.

The surfactants customarily employed in the art of formulation are described, for example, in "McCutcheon's Detergents and Emulsifiers Annual," MC Publishing Corp. Ringwood, N.J., 1979, and Sisely and Wood, "Encyclopedia of Surface Active Agents," Chemical Publishing Co., Inc. New York, 1980.

The agrochemical compositions usually contain from about 0.1 to about 99%, preferably about 0.1 to about 95%, and most preferably from about 3 to about 90% of the active ingredient, from about 1 to about 99.9%, preferably from abut 1 to about 99%, and most preferably from about 5 to about 95% of a solid or liquid adjuvant, and from about 0 to about 25%, preferably about 0.1 to about 25%, and most preferably from about 0.1 to about 20% of a surfactant.

Whereas commercial products are preferably formulated as concentrates, the end user will normally employ dilute formulations.

EXPERIMENTAL

The invention is illustrated in further detail by the following detailed procedures, preparations, and examples. The examples are for illustration only, and are not to be construed as limiting the scope of the present invention.

Standard recombinant DNA and molecular cloning techniques used here are well known in the art and are described by Sambrook et al., *Molecular Cloning*, eds., Cold Spring Harbor Laboratory Press, (1989)), by T. J. Silhavy, M. L. Berman, and L. W. Enquist, *Experiments with Gene Fusions*, Cold Spring Harbor Laboratory, Cold Spring Harbor, N.Y. (1984), and by Innis et al., *PCR Protocols, a Guide to Methods and Applications* eds., Academic Press (1990)).

A. Cloning and Characterization of Soraphen Biosynthetic Genes

Example 1

Isolation of the Soraphen Gene Cluster from Sorangium

Genomic DNA was isolated from *Sorangium cellulosum* and partially digested with Sau3A. Fragments of between 30 and 40 kb were size selected and cloned into the cosmid vector pHC79 (Hohn & Collins, Gene 11: 291–298 (1980)) which had been previously digested with BamHI and treated with alkaline phosphatase to prevent self ligation. The cosmid library thus prepared was probed with a 4.8 kb fragment which contains the graI region of *Streptomyces violaceoruber* strain Tü22 encoding ORFs 1–4 responsible for the biosynthesis of granaticin in *S. violaceoruber*. Cosmid clones which hybridized to the graI probe were identified and DNA was prepared for analysis by restriction digestion and further hybridization. Cosmid p98/1 was identified to contain a 1.8 kb SalI fragment which hybridized strongly to the graI region; this SalI fragment was located within a larger 6.5 kb PvuI fragment within the ~40 kb insert of p98/1. Determination of the sequence of part of the 1.8 kb SalI insert revealed homology to the acetyltransferase proteins required for the synthesis of erythromycin. Restriction mapping of the cosmid p98/1 was undertaken and generated the map depicted in FIG. 1. The DNA sequence of the portion of the soraphen gene cluster contained on cosmid p98/1 is disclosed in SEQ ID NO:4. *E. coli* HB101 containing p98/1 was deposited at the Agricultural Research Culture Collection (NRRL), 1815 N. University Street, Peoria, Ill. 61604 on May 20, 1994, and assigned accession number NRRL B-21255.

Example 2

Functional Analysis of the Soraphen Gene Cluster

The regions within p98/1 that encode proteins with a role in the biosynthesis of soraphen were identified through gene disruption experiments. Initially, DNA fragments were derived from cosmid p98/1 by restriction with PvuI and cloned into the unique PvuI cloning site (which is within the gene for ampicillin resistance) of the wide host-range plasmid pSUP2021 (Simon et al. in: Molecular Genetics of the Bacteria-Plant Interaction (ed.: A Puhler), Springer Verlag, Berlin pp. 98–106 (1983)). Transformed *E. coli* HB101 was selected for resistance to chloramphenicol, but sensitivity to ampicillin. Selected colonies carrying appropriate inserts were transferred to *Sorangium cellulosum* SJ3 by conjugation using the method described in the published application EP 0 501 921 (to Ciba-Geigy). Plasmids were transferred to *E. coli* ED8767 carrying the helper plasmid pUZ8 (Hedges & Matthew, Plasmid 2: 269–278 (1979)) and the donor cells were incubated with *Sorangium cellulosum* SJ3 cells from a stationary phase culture for conjugative transfer essentially as described in Example 5 of EP 0 501 921. Selection was on kanamycin, phleomycin and streptomycin. It has been determined that no plasmids tested thus far are capable of autonomous replication in *Sorangium cellulosum*, but rather, integration of the entire plasmid into the chromosome by homologous recombination occurs at a site within the cloned fragment at low frequency. These events can be selected for by the presence of antibiotic resistance markers on the plasmid. Integration of the plasmid at a given site results in the insertion of the plasmid into the chromosome and the concomitant disruption of this region from this event. Therefore, a given phenotype of interest, i.e. soraphen production, can be assessed, and disruption of the phenotype will indicate that the DNA region cloned into the plasmid must have a role in the determination of this phenotype.

Recombinant pSUP2021 clones with PvuI inserts of approximate size 6.5 kb (pSN105/7), 10 kb (pSN120/10), 3.8 kb (pSN120/43-39) and 4.0 kb (pSN120/46) were selected. The map locations (in kb) of these PvuI inserts as shown in FIG. 1 are: pSN105/7—25.0-31.7, pSN120/10—2.5-14.5, pSN120/43-39—16.1-20.0, and pSN120/46—20.0-24.0. pSN105/7 was shown by digestion with PvuI and SalI to contain the 1.8 kb fragment referred to above in Example 1. Gene disruptions with the 3.8, 4.0, 6.5, and 10 kb PvuI fragments all resulted in the elimination of soraphen production. These results indicate that all of these fragments contain genes or fragments of genes with a role in the production of this compound.

Figure 2:
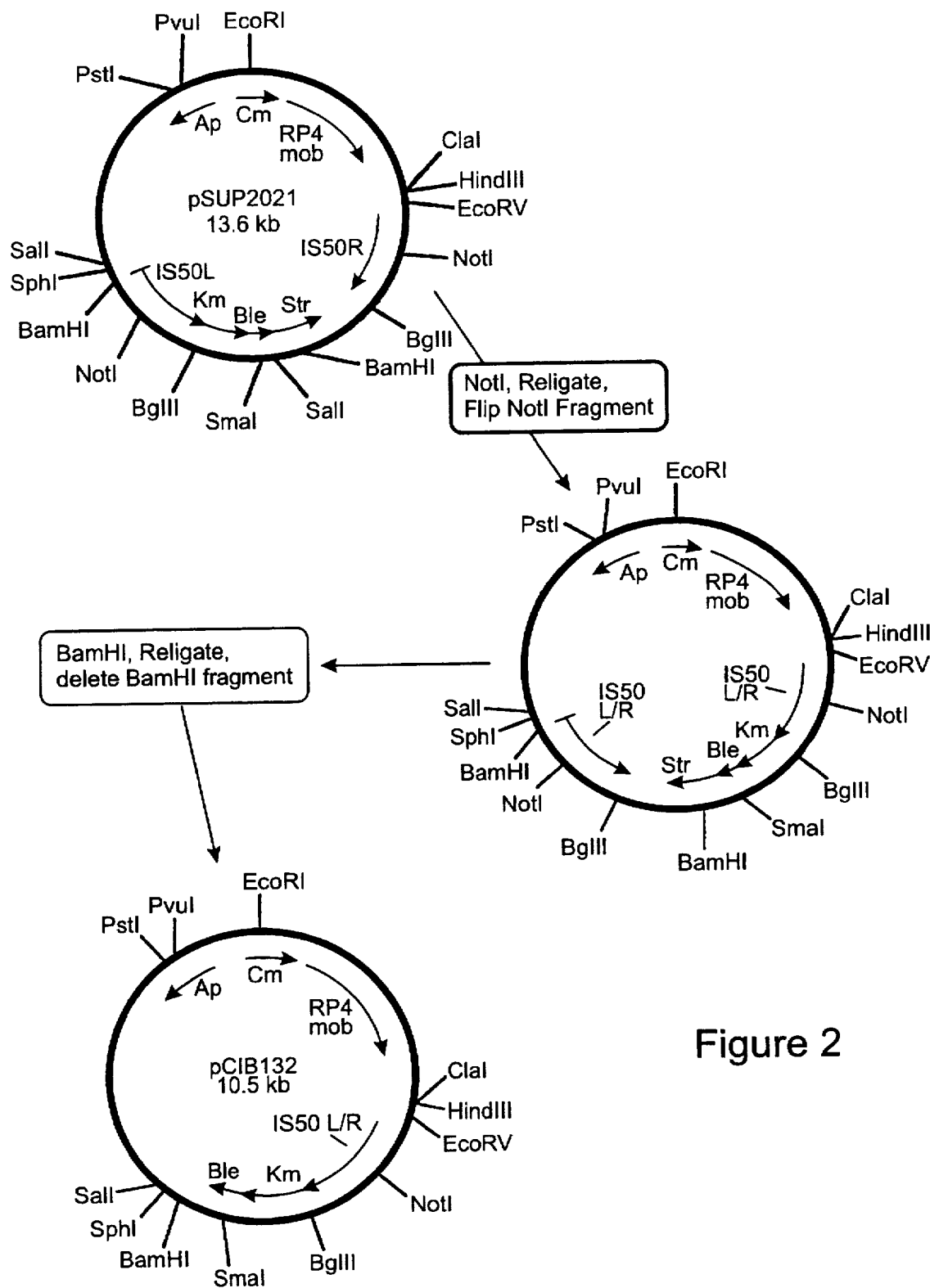
FIG. 2 shows the construction of pCIB132 from pSUP2021.

Subsequently gene disruption experiments were performed with two BglII fragments derived from cosmid p98/1. These were of size 3.2 kb (map location 32.4–35.6 on FIG. 1) and 2.9 kb (map location 35.6–38.5 on FIG. 1). These fragments were cloned into the BamHI site of plasmid pCIB132 that was derived from pSUP2021 according to FIG. 2. The ~5 kb NotI fragment of pSUF2021 was excised and inverted, followed by the removal of the ~3kb BamHI fragment. Neither of these BglII fragments was able to disrupt soraphen biosynthesis when reintroduced into *Sorangium* using the method described above. This indicates that the DNA of these fragments is not within the minimal PKS required for soraphen biosynthesis. Examination of the DNA sequence indicates the presence of a thioesterase domain 5' to, but near the BglII site at location 32.4. In addition, there are transcription stop codons immediately after the thioesterase domain which are likely to demarcate the end of the minimal PKS coding region.

Figure 3:
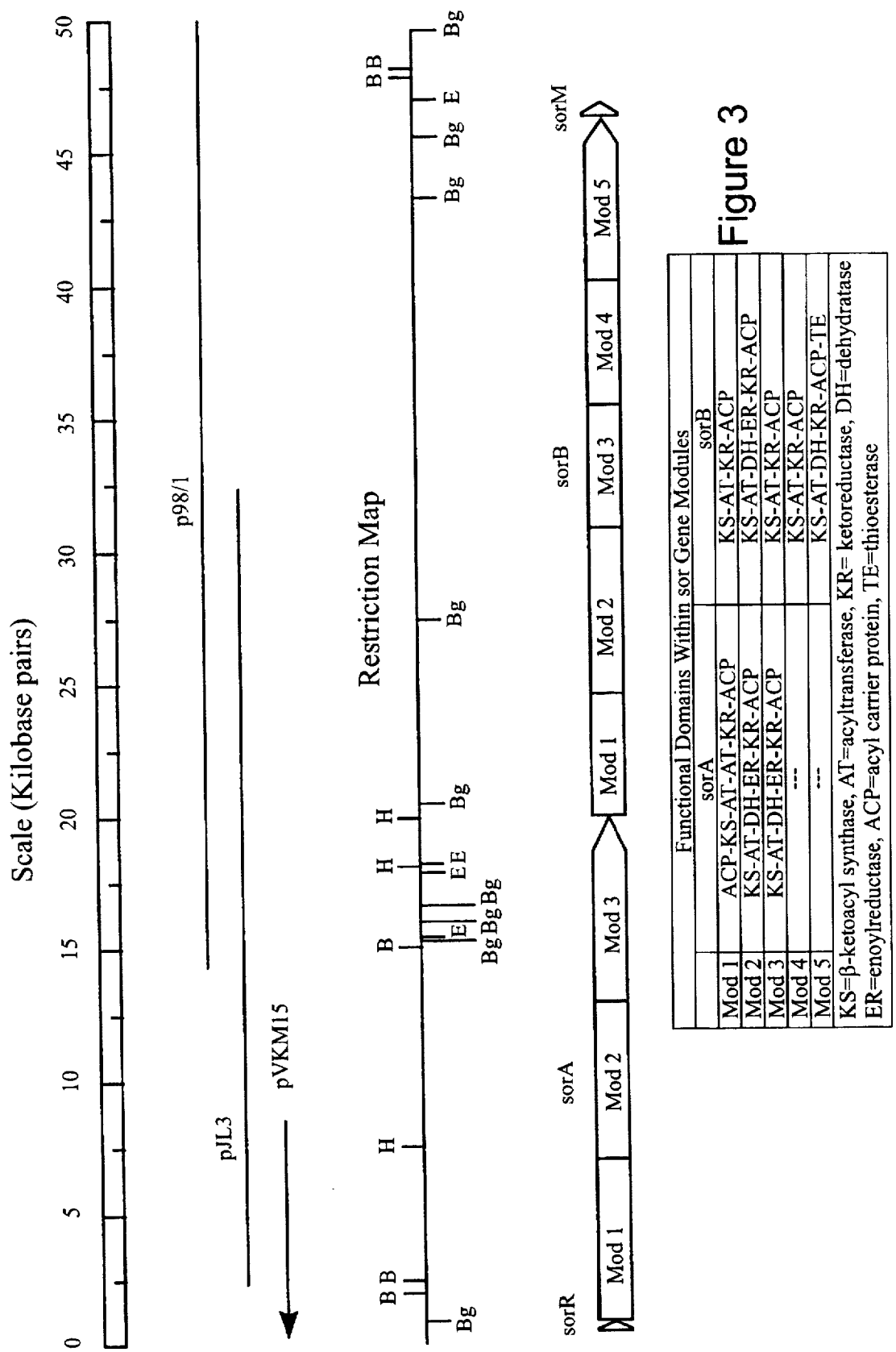
FIG. 3 depicts the genetic organization of the soraphen gene region within the sequence of SEQ ID NO:1. Positions of sorR, sorA, sorB, and sorM are indicated, along with modular locations within sorA and sorB. A restriction map and the overlapping relationships among cosmid clones pVKM15, pJL3, and p98/1 is also shown.

Delineation of the left end of the biosynthetic region required the isolation of three other cosmid clones, pJL1 and pJL3, which overlap p98/1 on the left end but include more DNA leftwards of p98/1, and pVKM15, which overlaps pJL3 on the left end. pJL1 and pJL3 were isolated by hybridization with the 1.3 kb BamHI fragment on the extreme left end of p98/1 (FIG. 1 map location 0.0–1.3) to the *Sorangium cellulosum* gene library. It should be noted that the BamHI site at 0.0 (FIG. 1) does not exist in the *S. cellulosum* chromosome but was formed as an artifact from the ligation of a Sau3A restriction fragment derived from the *Sorangium cellulosum* genome into the BamHI cloning site of pHC79. Southern hybridization with the 1.3 kb BamHI fragment demonstrated that pJL1 and pJL3 each contain an approximately 12.5 kb BamHI fragment that contains sequences common to the 1.3 kb fragment as this fragment is in fact delineated by the BamHI site at position 1.3 (FIG. 1). Gene disruption experiments using the 12.5 kb BamHI fragment indicated that this fragment contains sequences that are involved in the synthesis of soraphen. Gene disruption using smaller EcoRV fragments derived from this region and also indicated the requirement of this region for soraphen biosynthesis. For example, two EcoRV fragments of 3.4 and 1.1 kb located adjacent to the distal BamHI site at the left end of the 12.5 kb fragment resulted in a reduction in soraphen biosynthesis when used in gene disruption experiments. Plasmid pVKM15 was isolated from a second clone bank that was constructed by partially digesting genomic DNA of *Sorangium cellulosum* with SalI, size selection of the DNA to isolate fragments in the range of 20–30 kb, treatment with phosphatase, and ligation into the XhoI cloning site of the broad host range plasmid pVK100 (Knauf, V. C., and E. W. Nester. 1982. Plasmid 8: 45–54). It was identified by hybridization with a 375 base pair DNA fragment derived from the left end of plasmid pJL3 by PCR using primers including bases 3174–3191 and 3532–3549 (complementary strand) from SEQ ID NO:1. The approximate overlapping relationship of plasmids pVKM15, pJL3, and p98/1 is shown in FIG. 3. The DNA sequence of the DNA from pJL3 that is unique to the DNA of p98/1 was determined. The DNA sequence consisting of 2,270 base pairs of DNA from pVKM15 that represents DNA adjacent to the left end of DNA from pJL3 was also determined. *E. coli* HB101 containing pJL3 was deposited at the Agricultural Research Culture Collection (NRRL), 1815 N. University Street, Peoria, Ill. 61604 on May 20, 1994, and assigned accession number NRRL B-21254. *E. coli* HB101 containing pVKM15 was deposited at the NRRL on Dec. 11, 1996 and assigned accession number NRRL B-21651.

Example 3

Sequence Analysis of the Soraphen Gene Cluster

The DNA sequence of the soraphen gene cluster was determined from a SphI site in pVKM15 (base 1 of SEQ ID NO:1) to the BglII site near the right end of p98/1 (base 49377 of SEQ ID NO:1) using the Taq DyeDeoxy Terminator Cycle Sequencing Kit supplied by Applied Biosystems, Inc., Foster City, Calif. following the protocol supplied by the manufacturer. Sequencing reactions were run on a Applied Biosystems 373A Automated DNA Sequencer and the raw DNA sequence was assembled and edited using the "INHERIT" software package also from Applied Biosystems, Inc. The pattern recognition program "FRAMES" was used to search for open reading frames (ORFs) in all six translation frames of the DNA sequence. In total approximately 50 kb of contiguous DNA was assembled and this corresponds to the region determined to be critical to soraphen biosynthesis in the disruption experiments described in Example 2. This sequence encodes four genes which have the structure described below, in Table I below, and in FIG. 3.

sorR: sorR is approximately 378 base pairs size and encodes a protein that is highly homologous to the reductase domains of type I polyketide synthases such as eryA from *Saccharopolyspora erythraea*. (See Table I below and FIG. 3).

sorA: sorA is approximately 18948 base pairs in size and encodes a protein that is highly homologous to type I polyketide synthases (PKS) that are known to be involved in the synthesis of polyketide compounds. The PKS encoded by sorA contains three biosynthetic modules with homology to the modules found in the erythromycin biosynthetic genes (eryA) of *Saccharopolyspora erythraea* (Donadio et al. Science 252: 675–679 (1991)). Each module contains a β-ketoacylsynthase (KS), an acyltransferase (AT), a ketoreductase (KR) and an acyl carrier protein (ACP) domain as well as β-ketone processing domains which may include a dehydratase (DH) and/or enoyl reductase (ER) domain. In the biosynthesis of the polyketide structure each module directs the incorporation of a new two carbon extender unit and the correct processing of the β-ketone carbon. The first module in the PKS protein encoded by sorA contains two ACP and AT domains, which is typical of the module that catalyzes the first condensation of the initial and second carbon building units. (See Table I below and FIG. 3).

sorB: The sorB gene is approximately 26451 base pairs in size and is located immediately downstream of the sorA gene and its coding sequence overlaps that of the sorA sequence by four base pairs, indicating that the two genes are likely to be on the same transcriptional unit. Like the sorA gene, sorB is highly homologous to type I PKS genes such as eryA and it contains five biosynthetic modules. The last module in the sorA PKS protein contains a domain at the 3' end that has homology to the thioesterase (TE) domain of eryA which is involved in cleaving the thioester bond between the ACP domain of the PKS protein and the completed PKS carbon chain. By comparison to other polyketide biosynthetic gene units and the number of carbon atoms in the soraphen ring structure, it is likely that there should be a total of eight modules in order to direct the synthesis of 17 carbon molecule soraphen. The proteins encoded by the sorA and sorB genes together contain eight PKS biosynthetic modules. (See Table I below and FIG. 3).

sorM: The sorM gene is located downstream from sorB and is approximately 1044 base pairs in size. The protein encoded by the sorM gene is highly homolgous to known methyltransferases, including the methyltransferase from *Streptomyces hygroscopicus* that is involved in the synthesis of the polyketide rappamicin. (See Table I below and FIG. 3).

TABLE I

Positions of the sor genes, modules and activity domains.
All positions relate to the DNA sequence of SEQ ID NO: 1.

| | Nucleotide Sequence | |
|---|---|---|
| | Starting Base | Ending Base |
| sorR | 383 | 760 |
| sorA | 927 | 19874 |
| Module 1 | | |
| ACP1a | 942 | 1190 |
| KS | 1257 | 2525 |
| AT1a | 2820 | 3839 |
| AT1b | 4116 | 5156 |
| KR | 6045 | 6598 |
| ACP1b | 6864 | 7115 |
| Module 2 | | |
| KS | 7203 | 8474 |
| AT | 8802 | 9815 |
| DH | 9915 | 10413 |
| ER | 11273 | 12314 |
| KR | 12327 | 12884 |
| ACP | | |
| Module 3 | | |
| KS | 13455 | 14711 |
| AT | 15045 | 16040 |
| DH | 16137 | 16634 |
| ER | 17493 | 18536 |
| KR | 18549 | 19106 |
| ACP | 19365 | 19616 |

TABLE I-continued

Positions of the sor genes, modules and activity domains.
All positions relate to the DNA sequence of SEQ ID NO: 1.

| | Nucleotide Sequence | |
|---|---|---|
| | Starting Base | Ending Base |
| sorB | 19871 | 46318 |
| Module 1 | | |
| KS | 19870 | 21226 |
| AT | 21554 | 22567 |
| KR | 23483 | 24040 |
| ACP | 24305 | 24556 |
| Module 2 | | |
| KS | 24638 | 25909 |
| AT | 26243 | 27237 |
| DH | 27341 | 27838 |
| ER | 28697 | 29740 |
| KR | 29753 | 30310 |
| ACP | 30569 | 30820 |
| Module 3 | | |
| KS | 30881 | 32131 |
| AT | 32465 | 33457 |
| KR | 34373 | 34930 |
| ACP | 35195 | 35446 |
| Module 4 | | |
| KS | 35528 | 36799 |
| AT | 37133 | 38128 |
| KR | 39038 | 39595 |
| ACP | 39863 | 40114 |
| Module 5 | | |
| KS | 40190 | 41461 |
| AT | 41795 | 42790 |
| DH | 42890 | 43390 |
| KR | 44339 | 44896 |
| ACP | 45152 | 45399 |
| TE | 45668 | 46318 |
| sorM | 46851 | 47891 |

Example 4

Soraphen: Requirement for Methylation

Synthesis of polyketides typically requires, as a first step, the condensation of a starter unit (commonly acetate) and an extender unit (malonate) with the loss of one carbon atom in the form of $CO_2$ to yield a three-carbon chain. All subsequent additions result in the addition of two carbon units to the polyketide ring (Donadio et al. Science 252: 675–679 (1991)). Since soraphen has a 17-carbons ring, it is likely that there are 8 biosynthetic modules required for its synthesis. Three modules are encoded by sorA and five by sorB.

The polyketide modular biosynthetic apparatus present in *Sorangium cellulosum* is required for the production of the compound, soraphen C, which has less antipathogenic activity compared to soraphen A. The structure of this compound is the same as that of the antipathogenic soraphen A with the exception that the O-methyl groups of soraphen A at positions 6, 7, and 14 of the ring are hydroxyl groups. These are methylated by a specific methyltransferase to form the active compound soraphen A. A similar situation exists in the biosynthesis of erythromycin in *Saccharopolyspora erythraea*. The final step in the biosynthesis of this molecule is the methylation of three hydroxl groups by a methyltransferase (Haydock et al., Mol. Caen. Genet. 230: 120–128 (1991)). It is highly likely, therefore, that the protein encoded by the sorM gene described above is involved in the biosynthesis of soraphen A (soraphen C is unmethylated and soraphen B is partially methylated). In all polyketide biosynthesis systems examined thus far, all of the biosynthetic genes and associated methylases are clustered together (Summers et al. J Bacteriol 174: 1810–1820 (1992)).

Soraphen Determination: *Sorangium cellulosum* cells were cultured in a liquid growth medium containing an exchange resin, XAD-5 (Rohm and Haas) (5% w/v). The soraphen A produced by the cells bound to the resin which was collected by filtration through a polyester filter (Sartorius B 420-47-N) and the soraphen was released from the resin by extraction with 50 ml isopropanol for 1 hr at 30° C. The isopropanol containing soraphen A was collected and concentrated by drying to a volume of approximately 1 ml. Aliquots of this sample were analyzed by HPLC at 210 nm to detect and quantify the soraphen A. This assay procedure is specific for soraphen A (fully methylated); partially and non-methylated soraphen forms have a different $R_T$ and are not measured by this procedure. This procedure was used to assay soraphen A production after gene disruption.

Example 5

Identification of the Native sor Gene Promoter Region

Figure 4:
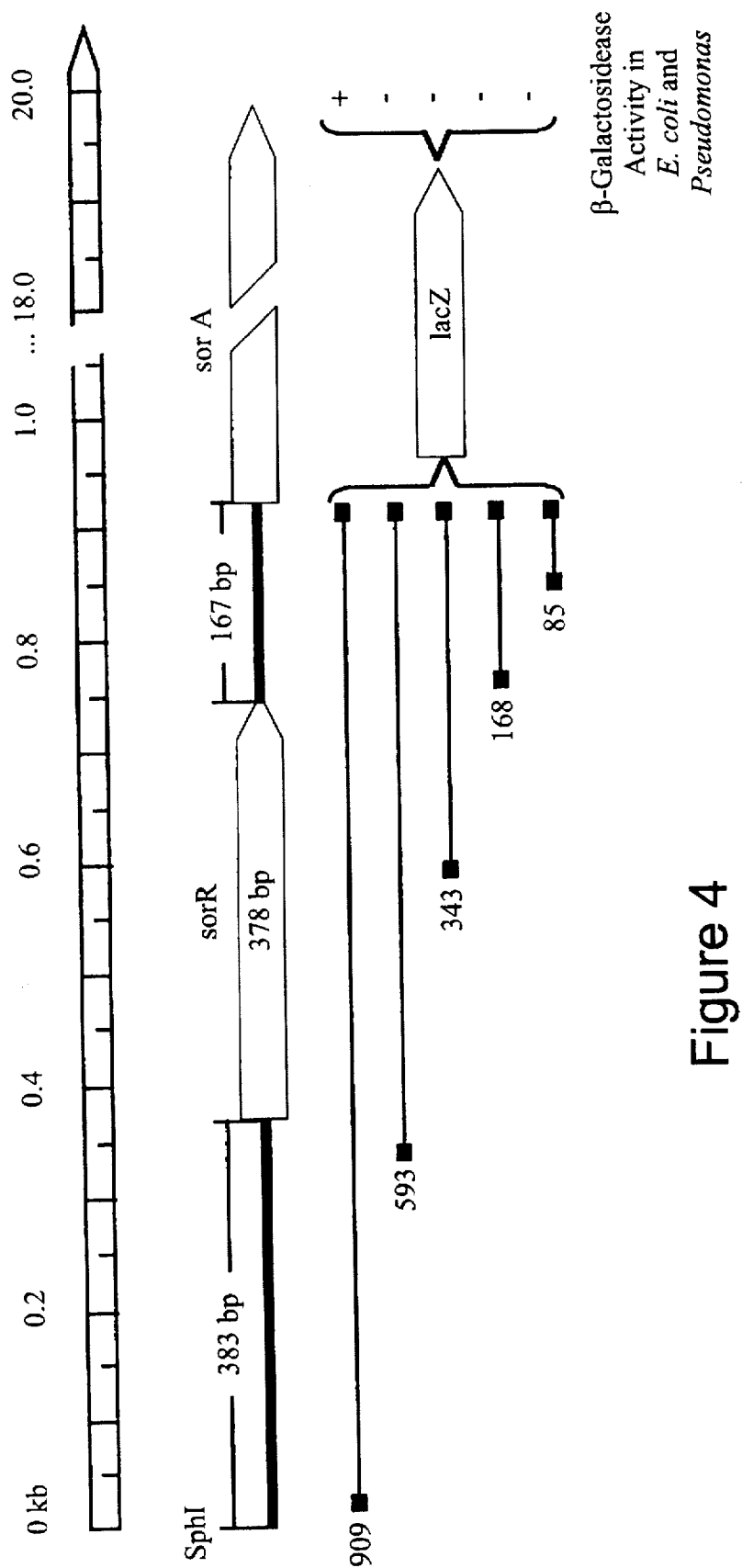
FIG. 4 shows the positions of the sorR and sorA coding sequences and the promoter fragments cloned by PCR with their sizes and base pairs below the gene region. These fragments were fused to a promoterless lacZ. The activity of lacZ in *E. coli* and Pseudomonas is shown to the fight.

Upon examination of the sorA, B, and R genes and their respective locations within the sor gene region, it was not readily apparent where the promoter for expression of these genes was located. Since the coding sequences for the sorA and B genes overlaps by 4 bases, it is likely that these genes are cotranscribed on a single transcriptional unit. However, it was not known if the sorR gene was also transcribed on the same transcriptional unit, or if it was on a separate unit. In order to address this issue, we cloned by PCR various DNA fragments of varying length that all started just 5' to the start of the sorA gene and extended varying distances in the 5' direction. The PCR primers used to anchor the 5' end of the various fragments were bases 14–30, 330–346, 580–596, 755–771, and 838–854 which generated the fragments shown in FIG. 4 (largest to smallest, respectively) by PCR with a single 3' anchor primer, bases 907–923 (complementary strand). Each of the five fragments generated by these PCR reactions were cloned and fused to the promoterless lacZ gene from *E. coli*. The lacZ gene encodes β-galactosidase which cleaves the colorless substrate X-Gal to a blue dye molecule. The PCR generated fragments from the sor gene region fused to the lacZ gene were cloned into the broad host range plasmid pRK290 and introduced into *E. coli* strain DHα and *Pseudomonas fluorescens* strain CGA267356 and these strains were cultured on Luria agar containing X-Gal. Only the largest of the PCR fragments fused to lacZ resulted in the *E. coli* and *P. fluorescens* colonies turning blue, indicating expression of the lacZ gene in these cases (FIG. 4). These results indicate that the native promoter of the sorA and sorB genes is located in the region 5' to the sorR gene. Therefore, the sorR, sorA and sorB genes are likely to be located on a single transcriptional unit and the promoter for these genes is active in *E. coli* and Pseudomonas. Furthermore, from these results it would be expected that the sor genes would be expressed from the native sor gene promoter in these and other Gram-negative bacteria.

B. Expression of PKS Genes in Microbial Hosts

Example 6

Overexpression of PKS Genes for Overproduction of Polyketide Antibiotics

The PKS genes of this invention can be expressed in heterologous organisms for the purposes of their production at greater quantities than might be possible from their native hosts. A suitable host for heterologous expression is *E. coli* and techniques for gene expression in *E. coli* are well known. For example, the cloned PKS genes can be expressed in *E. coli* using the expression vector pKK223 as described in Example 11 of Ser. No. 08/258,261. The cloned genes can be fused in transcriptional fusion, so as to use the available ribosome binding site cognate to the heterologous gene. This approach facilitates the expression of operons which encode more than one open reading frame as translation of the individual ORFs will thus be dependent on their cognate ribosome binding site signals. Alternatively PKS genes can be fused to the vector's ATG (e.g. as an NcoI fusion) so as to use the *E. coli* ribosome binding site. For multiple ORF expression in *E. coli* (e.g. in the case of operons with multiple ORFs) this type of construct would require a separate promoter to be fused to each ORF. It is possible, however, to fuse the first ATG of the PKS operon to the *E. coli* ribosome binding site while requiring the other ORFs to utilize their cognate ribosome binding sites. These types of construction for the overexpression of genes in *E. coli* are well known in the art. Suitable bacterial promoters include the lac promoter, the tac (trp/lac) promoter, and the Pλ promoter from bacteriophage λ. Suitable commercially available vectors include, for example, pKK223-3, pKK233-2, pDR540, pDR720, pYEJ001 and pPL-Lambda (from Pharmacia, Piscataway, N.J.).

Similarly, gram positive bacteria, notably Bacillus species and particularly *Bacillus licheniformis*, are used in commercial scale production of heterologous proteins and can be adapted to the expression of PKS genes (e.g. Quax et al., In: Industrial Microorganisms: Basic and Applied Molecular Genetics, Eds.: Baltz et al., American Society for Microbiology, Washington (1993)). Regulatory signals from a highly expressed Bacillus genes (e.g. amylase promoter, Quax et al., supra) are used to generate transcriptional fusions with the PKS genes.

In some instances, high level expression of bacterial genes has been achieved using yeast systems, such as the methylotrophic yeast *Pichia pastoris* (Sreekrishna, In: Industrial microorganisms: basic and applied molecular genetics, Baltz, Hegeman, and Skatrud eds., American Society for Microbiology, Washington (1993)). The PKS gene(s) of interest are positioned behind 5' regulatory sequences of the Pichia alcohol oxidase gene in vectors such as pHIL-D1 and pHIL-D2 (Sreekrishna, supra). Such vectors are used to transform Pichia and introduce the heterologous DNA into the yeast genome. Likewise, the yeast *Saccharomyces cerevisiae* has been used to express heterologous bacterial genes (e.g. Dequin & Barre, Biotechnology 12: 173–177 (1994)). The yeast *Kluyveromyces lactis* is also a suitable host for heterologous gene expression (e.g. van den Berg et al., Biotechnology 8: 135–139 (1990)).

Overexpression of PKS genes in organisms such as *E. coli*, Bacillus and yeast, which are known for their rapid growth and multiplication, will enable fermentation-production of larger quantities of polyketide antibiotics. The choice of organism may be restricted by the possible susceptibility of the organism to the polyketide antibiotic being overproduced; however, the likely susceptibility can be determined by the procedures outlined in Section D. The polyketide antibiotics can be isolated and purified from such cultures for use in the control of microorganisms such as fungi and bacteria.

C. Expression of PKS Genes in Microbial Hosts for Biocontrol Purposes

The cloned PKS genes of this invention can be utilized to increase the efficacy of biocontrol strains of various microorganisms. One possibility is the transfer of the genes for a particular polyketide antibiotic back into its native host under stronger transcriptional regulation to cause the production of larger quantities of the polyketide antibiotic. Another possibility is the transfer of genes to a heterologous host, causing production in the heterologous host of an polyketide antibiotic not normally produced by that host.

Microorganisms which are suitable for the heterologous overexpression of PKS genes are all microorganisms which are capable of colonizing plants or the rhizosphere. As such they will be brought into contact with phytopathogenic fungi causing an inhibition of their growth. These include gram-negative microorganisms such as Pseudomonas, Enterobacter and Serratia, the gram-positive microorganism Bacillus and the fungi Trichoderma and Gliocladium. Particularly preferred heterologous hosts are *Pseudomonas fluorescens, Pseuclomonas putida, Pseudomonas cepacia, Pseudornonas aureofaciens, Pseudomonas aurantiaca, Enterobacter cloacae, Serratia marscesens, Bacillus subtilis, Bacillus cereus, Trichoderma viride, Trichoderma harzianum* and *Gliocladium virens*.

Example 7

Expression of PKS Genes in *E. coli* and Other Gram-Negative Bacteria

Many genes have been expressed in gram-negative bacteria in a heterologous manner. Example 11 of Ser. No. 08/258,261 describes the expression of genes for pyrrolnitrin biosynthesis in *E. coli* using the expression vector pKK223-3 (Pharmacia catalogue #27-4935-01). This vector has a strong tac promoter (Brosius, J. et al., *Proc. Natl. Acad. Sci. USA* 81) regulated by the lac repressor and induced by IPTG. A number of other expression systems have been developed for use in *E. coli* and some are detailed in E (above). The thermoinducible expression vector pP$_L$ (Pharmacia #27-4946-01) uses a tightly regulated bacteriophage λ promoter which allows for high level expression of proteins. The lac promoter provides another means of expression but the promoter is not expressed at such high levels as the tac promoter. With the addition of broad host range replicons to some of these expression system vectors, production of antifungal compounds in closely related gram negative-bacteria such as Pseudomonas, Enterobacter, Serratia and Erwinia is possible. For example, pLRKD211 (Kaiser & Kroos, Proc. Natl. Acad. Sci. USA 81: 5816–5820 (1984)) contains the broad host range replicon ori T which allows replication in many gram-negative bacteria.

In *E. coli*, induction by IPTG is required for expression of the tac (i.e. trp-lac) promoter. When this same promoter (e.g. on wide-host range plasmid pLRKD211) is introduced into Pseudomonas it is constitutively active without induction by IPTG. This trp-lac promoter can be placed in front of any gene or operon of interest for expression in Pseudomonas or any other closely related bacterium for the purposes of the constitutive expression of such a gene. ff the operon of interest contains the information for the biosynthesis of an polyketide antibiotic, then an otherwise biocontrol-minus strain of a gram-negative bacterium may be able to protect plants against a variety of fungal diseases. Thus, genes for antifungal compounds can therefore be placed behind a strong constitutive promoter, transferred to a bacterium that normally does not produce antifungal products and which has plant or rhizosphere colonizing properties turning these organisms into effective biocontrol strains. Other possible promoters can be used for the constitutive expression of PKS genes in gram-negative bacteria. These include, for example, the promoter from the Pseudomonas regulatory genes gafA and lemA (WO 94/01561) and the *Pseudomonas savastanoi* IAA operon promoter (Gaffney et al., *J. Bacteriol.* 172: 5593–5601 (1990).

Example 8

Expression of PKS Genes in Gram-Positive Bacteria

Heterologous expression of genes involved in the biosynthesis of polyketide antibiotics in gram-positive bacteria is another means of producing new biocontrol strains. Expression systems for Bacillus and Streptorayces are the best characterized. The promoter for the erythromycin resistance gene (erroR) from *Streptococcus pneumoniae* has been shown to be active in gram-positive aerobes and anaerobes and also in *E. coli* (Trieu-Cuot et al., Nucl Acids Res 18: 3660 (1990)). A further antibiotic resistance promoter from the thiostreptone gene has been used in Streptomyces cloning vectors (Bibb, Mol Gen Genet 199: 26–36 (1985)). The shuttle vector pHT3101 is also appropriate for expression in Bacillus (Lereclus, FEMS Microbiol Lett 60: 211–218 (1989)). By expressing an operon (such as the soraphen operon) or individual PKS genes under control of the ermR or other promoters it will be possible to convert soil bacilli into strains able to protect plants against microbial diseases. A significant advantage of this approach is that many gram-positive bacteria produce spores which can be used in formulations that produce biocontrol products with a longer shelf life. Bacillus and Streptomyces species are aggressive colonizers of soils. In fact both produce secondary metabolites including antibiotics active against a broad range of organisms and the addition of heterologous antifungal genes including (including those encoding pyrrolnitrin, soraphen, phenazine or cyclic peptides) to gram-positive bacteria may make these organisms even better biocontrol strains.

Example 9

Expression of PKS Genes in Fungi

*Trichoderma harzianum* and *Gliocladium virens* have been shown to provide varying levels of biocontrol in the field (U.S. Pat. No. 5,165,928 and U.S. Pat. No. 4,996,157, both to Cornell Research Foundation). The successful use of these biocontrol agents will be greatly enhanced by the development of improved strains by the introduction of PKS genes. This could be accomplished by a number of ways which are well known in the art. One is protoplast mediated transformation of the fungus by PEG or electroporation-mediated techniques. Alternatively, particle bombardment can be used to transform protoplasts or other fungal cells with the ability to develop into regenerated mature structures. The vector pAN7-14 1, originally developed for Aspergillus transformation and now used widely for fungal transformation (Curragh et al., *Mycol. Res.* 97(3): 313–317 (1992); Tooley et al., *Curr. Genet.* 21: 55–60 (1992); Punt et al Gene 56: 117–124 (1987)) is engineered to contain the soraphen operon, or any other genes for polyketide antibiotic biosynthesis. This plasmid contains the *E. coli* the hygromycin B resistance gene flanked by the *Aspergillus nidulans* gpd promoter and the trpC terminator (Punt et al., Gene 56: 117–124 (1987)).

D. In Vitro Activity of Anti-phytopathogenic Substances Against Plant Pathogens

Example 10

Bioassay Procedures for the Detection of Antifungal Activity

Inhibition of fungal growth by a potential antifungal agent can be determined in a number of assay formats. Macroscopic methods which are commonly used include the agar diffusion assay (Dhingra & Sinclair, Basic Plant Pathology Methods, CRC Press, Boca Raton, Fla. (1985)) and assays in liquid media (Broekaert et at., FEMS Microbiol. Lett. 69: 55–60.(1990)). Both types of assay are performed with either fungal spores or mycelia as inocula. The maintenance of fungal stocks is in accordance with standard mycological procedures. Spores for bioassay are harvested from a mature plate of a fungus by flushing the surface of the culture with sterile water or buffer. A suspension of mycelia is prepared by placing fungus from a plate in a blender and homogenizing until the colony is dispersed. The homogenate is filtered through several layers of cheesecloth so that larger particles are excluded. The suspension which passes through the cheesecloth is washed by centrifugation and replacing the supernatant with fresh buffer. The concentration of the mycelial suspension is adjusted empirically, by testing the suspension in the bioassay to be used.

Agar diffusion assays may be performed by suspending spores or mycelial fragments in a solid test medium, and applying the antifungal agent at a point source, from which it diffuses. This may be done by adding spores or mycelia to melted fungal growth medium, then pouring the mixture into a sterile dish and allowing it to gel. Sterile filters are placed on the surface of the medium, and solutions of antifungal agents are spotted onto the filters. After the liquid has been absorbed by the filter, the plates are incubated at the appropriate temperature, usually for 1–2 days. Growth inhibition is indicated by the presence of zones around filters in which spores have not germinated, or in which mycelia have not grown. The antifungal potency of the agent, denoted as the minimal effective dose, may be quantified by spotting serial dilutions of the agent onto filters, and determining the lowest dose which gives an observable inhibition zone. Another agar diffusion assay can be performed by cutting wells into solidified fungal growth medium and placing solutions of antifungal agents into them. The plate is inoculated at a point equidistant from all the wells, usually at the center of the plate, with either a small aliquot of spore or mycelial suspension or a mycelial plug cut directly from a stock culture plate of the fungus. The plate is incubated for several days until the growing mycelia approach the wells, then it is observed for signs of growth inhibition. Inhibition is indicated by the deformation of the roughly circular form which the fungal colony normally assumes as it grows. Specifically, if the mycelial front appears flattened or even concave relative to the uninhibited sections of the plate, growth inhibition has occurred. A minimal effective concentration may be determined by testing diluted solutions of the agent to find the lowest at which an effect can be detected.

Bioassays in liquid media are conducted using suspensions of spores or mycelia which are incubated in liquid fungal growth media instead of solid media. The fungal inocula, medium, and antifungal agent are mixed in wells of a 96-well microtiter plate, and the growth of the fungus is followed by measuring the turbidity of the culture spectrophotometrically. Increases in turbidity correlate with increases in biomass, and are a measure of fungal growth. Growth inhibition is determined by comparing the growth of the fungus in the presence of the antifungal agent with growth in its absence. By testing diluted solutions of antifungal inhibitor, a minimal inhibitory concentration or an $EC_{50}$ may be determined.

Example 11

Bioassay Procedures for the Detection of Antibacterial Activity

A number of bioassays may be employed to determine the antibacterial activity of an unknown compound. The inhibition of bacterial growth in solid media may be assessed by dispersing an inoculum of the bacterial culture in melted medium and spreading the suspension evenly in the bottom of a sterile Petri dish. After the medium has gelled, sterile filter disks are placed on the surface, and aliquots of the test material are spotted onto them. The plate is incubated overnight at an appropriate temperature, and growth inhibition is observed as an area around a filter in which the bacteria have not grown, or in which the growth is reduced compared to the surrounding areas. Pure compounds may be characterized by the determination of a minimal effective dose, the smallest amount of material which gives a zone of inhibited growth. In liquid media, two other methods may be employed. The growth of a culture may be monitored by measuring the optical density of the culture, in actuality the scattering of incident light. Equal inocula are seeded into equal culture volumes, with one culture containing a known amount of a potential antibacterial agent. After incubation at an appropriate temperature, and with appropriate aeration as required by the bacterium being tested, the optical densities of the cultures are compared. A suitable wavelength for the comparison is 600 nm. The antibacterial agent may be characterized by the determination of a minimal effective dose, the smallest amount of material which produces a reduction in the density of the culture, or by determining an $EC_{50}$, the concentration at which the growth of the test culture is half that of the control. The bioassays described above do not differentiate between bacteriostatic and bacteriocidal effects. Another assay can be performed which will determine the bacteriocidal activity of the agent. This assay is carried out by incubating the bacteria and the active agent together in liquid medium for an amount of time and under conditions which are sufficient for the agent to exert its effect. After this incubation is completed, the bacteria may be either washed by centrifugation and resuspension, or diluted by the addition of fresh medium. In either case, the concentration of the antibacterial agent is reduced to a point at which it is no longer expected to have significant activity. The bacteria are plated and spread on solid medium and the plates are incubated overnight at an appropriate temperature for growth. The number of colonies which arise on the plates are counted, and the number which appeared from the mixture which contained the antibacterial agent is compared with the number which arose from the mixture which contained no antibacterial agent. The reduction in colony-forming units is a measure of the bacteriocidal activity of the agent. The bacteriocidal activity may be quantified as a minimal effective dose, or as an $EC_{50}$, as described above. Bacteria which are used in assays such as these include species of Agrobacterium, Erwinia, Clavibacter, Xanthomonas, and Pseudomonas.

Example 12

Antipathogenic Activity Determination of Polyketide Antibiotics

Polyketide antibiotics are assayed using the procedures of the preceding two examples to identify the range of fungi and bacteria against which they are active. The polyketide antibiotic can be isolated from the cells and culture medium of the host organism normally producing it, or can alternatively be isolated from a heterologous host which has been engineered to produce the polyketide antibiotic. A further possibility is the chemical synthesis of polyketide antibiotics of known chemical structure, or derivatives thereof.

E. Expression of PKS Genes in Transgenic Plants

Example 13

Modification of Coding Sequences and Adjacent Sequences

The cloned PKS genes described in this application can be modified for expression in transgenic plant hosts. This is done with the aim of producing extractable quantities of polyketide antibiotic from transgenic plants or, alternatively, the aim of such expression can be the accumulation of polyketide antibiotic in plant tissue for the provision of pathogen protection on host plants. A host plant expressing genes for the biosynthesis of a polyketide antibiotic and which produces the polyketide antibiotic in its cells will have enhanced resistance to phytopathogen attack and will be thus better equipped to withstand crop losses associated with such attack.

The transgenic expression in plants of genes derived from microbial sources may require the modification of those genes to achieve and optimize their expression in plants. In particular, bacterial ORFs which encode separate native microbe are best expressed by the same transcript in the native microbe are best expressed in plants on separate transcripts. To achieve this, each microbial ORF is isolated individually and cloned within a cassette which provides a plant promoter sequence at the 5' end of the ORF and a plant transcriptional terminator at the 3' end of the ORF. The isolated ORF sequence preferably includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. By "plant promoter" and "plant transcriptional terminator" it is intended to mean promoters and transcriptional terminators which operate within plant cells. This includes promoters and transcription terminators which may be derived from non-plant sources such as viruses (an example is the Cauliflower Mosaic Virus).

In some cases, modification to the ORF coding sequences and adjacent sequence will not be required. It is sufficient to isolate a fragment containing the ORF of interest and to insert it downstream of a plant promoter. For example, Gaffney et al. (Science 261: 754–756 (1993)) have expressed the Pseudomonas nahG gene in transgenic plants under the control of the CaMV 35S promoter and the CaMV tml terminator successfully without modification of the coding sequence and with x bp of the Pseudomonas gene upstream of the ATG still attached, and y bp downstream of the STOP codon still attached to the nahG ORF. Preferably as little adjacent microbial sequence should be left attached upstream of the ATG and downstream of the STOP codon. In practice, such construction may depend on the availability of restriction sites.

In other cases, the expression of genes derived from microbial sources may provide problems in expression. These problems have been well characterized in the art and are particularly common with genes derived from certain sources such as Bacillus. These problems may apply to the PKS genes of this invention and the modification of these genes can be undertaken using techniques now well known in the art. The following problems may be encountered:

(1) Codon Usage: The preferred codon usage in plants differs from the preferred codon usage in certain microorganisms. Comparison of the usage of codons within a cloned microbial ORF to usage in plant genes (and in particular genes from the target plant) will enable an identification of the codons within the ORF which should preferably be changed. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

(2) GC/AT Content: Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites (see below).

(3) Sequences Adjacent to the Initiating Methionine: Plants differ from microorganisms in that their messages do not possess a defined ribosome binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210) have suggested the sequence GTCGACCATGGTC (SEQ ID NO:2) as a consensus translation initiator for the expression of the E. coli uidA gene in plants. Further, Joshi (NAR 15: 6643–6653 (1987)) has compared many plant sequences adjacent to the ATG and suggests the consensus TAAA-CAATGGCT (SEQ ID NO:3). In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. A survey of 14 maize genes located in the GertBank database provided the following results:

| Position Before the Initiating ATG in 14 Maize Genes: | | | | | | | | | | |
|---|---|---|---|---|---|---|---|---|---|---|
|   | −10 | −9 | −8 | −7 | −6 | −5 | −4 | −3 | −2 | −1 |
| C | 3 | 8 | 4 | 6 | 2 | 5 | 6 | 0 | 10 | 7 |
| T | 3 | 0 | 3 | 4 | 3 | 2 | 1 | 1 | 1 | 0 |
| A | 2 | 3 | 1 | 4 | 3 | 2 | 3 | 7 | 2 | 3 |
| G | 6 | 3 | 6 | 0 | 6 | 5 | 4 | 6 | 1 | 5 |

This analysis can be done for the desired plant species into which PKS genes are being incorporated, and the sequence adjacent to the ATG modified to incorporate the preferred nucleotides.

(4) Removal of Illegitimate Splice Sites: Genes cloned from non-plant sources and not optimized for expression in plants may also contain motifs which may be recognized in plants as 5' or 3' splice sites, and be cleaved, thus generating truncated or deleted messages. These sites can be removed using the techniques described in pending application Ser. No. 07/961,944, hereby incorporated by reference.

Techniques for the modification of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (to Monsanto), EP 0 359

472 (to Lubrizol) and WO 93/07278 (to Ciba-Geigy). In most cases it is preferable to assay the expression of gene constructions using transient assay protocols (which are well known in the art) prior to their transfer to transgenic plants.

Example 14

Construction of Plant Transformation Vectors

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selection markers used routinely in transformation include the nptII gene which confers resistance to kanamycin and related antibiotics (Messing & Vierra, Gene 19: 259–268 (1982); Bevan et al., Nature 304: 184–187 (1983)), the bar gene which confers resistance to the herbicide phosphinothricin (White et al., Nucl Acids Res 18: 1062 (1990), Spencer et al. Theor Appl Genet 79: 625–631 (1990)), the hph gene which confers resistance to the antibiotic hygromycin (Biochinger & Diggelmann, Mol Cell Biol 4: 2929–2931), and the dhfr gene, which confers resistance to methatrexate (Bourouis et al., EMBO J. 2(7): 1099–1104 (1983)).

(1) Construction of Vectors Suitable for Agrobacterium Transformation

Many vectors are available for transformation using *Agrobacterium tumefaciens*. These typically carry at least one T-DNA border sequence and include vectors such as pBIN 19 (Bevan, Nucl. Acids Res. (1984)) and pXYZ. Below the construction of two typical vectors is described.

Construction of pCIB200 and pCIB2001: The binary vectors pCIB200 and pCIB2001 are used for the construction of recombinant vectors for use with Agrobacterium and was constructed in the following manner. pTJS75kan was created by NarI digestion of pTJS75 (Schmidhauser & Helinski, J Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982); Bevan et al., Nature 304: 184–187 (1983); McBride et at., Plant Molecular Biology 14: 266–276 (1990)). XhoI linkers were ligated to the EcoRV fragment of pCIB7 which contains the left and right T-DNA borders, a plant selectable nos/nptII chimeric gene and the pUC polylinker (Rothstein et al., Gene 53: 153–161 (1987)), and the XhoI-digested fragment was cloned into SalI-digested pTJS75kan to create pCIB200 (see also EP 0 332104, example 19). pCIB200 contains the following unique polylinker restriction sites: EcoRI, SstI, KpnI, BglII, XbaI, and SalI. pCIB2001 is a derivative of pCIB200 which created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

Construction of pCIB10 and Hygromycin Selection Derivatives thereof: The binary vector pCIB10 contains a gene encoding kanamycin resistance for selection in plants, T-DNA right and left border sequences and incorporates sequences from the wide host-range plasmid pRK252 allowing it to replicate in both *E. coli* and Agrobacterium. Its construction is described by Rothstein et al. (Gene 53: 153–161 (1987)). Various derivatives of pCIB10 have been constructed which incorporate the gene for hygromycin B phosphotransferase described by Gritz et al. (Gene 25: 179–188 (1983)). These derivatives enable selection of transgenic plant cells on hygromycin only (pCIB743), or hygromycin and kanamycin (pCIB715, pCIB717).

(2) Construction of Vectors Suitable for non-Agrobacterium Transformation.

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques which do not rely on Agrobacterium include transformation via particle bombardment, protoplast uptake (e.g. PEG and electroporation) and microinjection. The choice of vector depends largely on the preferred selection for the species being transformed. Below, the construction of some typical vectors is described.

Construction of pCIB3064: pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites were mutated using standard PCR techniques in such a way as to remove the ATGs and generate the restriction sites SspI and PvuII. The new restriction sites were 96 and 37 bp away from the unique SalI site and 101 and 42 bp away from the actual start site. The resultant derivative of pCIB246 was designated pCIB3025. The GUS gene was then excised from pCIB3025 by digestion with SalI and SacI, the termini rendered blunt and religated to generate plasmid pCIB3060. The plasmid pJIT82 was obtained from the John Innes Centre, Norwich and the a 400 bp SmaI fragment containing the bar gene from *Streptomyces viridochromogenes* was excised and inserted into the HpaI site of pCIB3060 (Thompson et al. EMBO J 6: 2519–2523 (1987)). This generated pCIB3064 which comprises the bar gene under the control of the CaMV 35S promoter and terminator for herbicide selection, a gene fro ampicillin resistance (for selection in *E. coli*) and a polylinker with the unique sites SphI, PstI, HindIII, and BamHI. This vector is suitable for the cloning of plant expression cassettes containing their own regulatory signals.

Construction of pSOG19 and pSOG35: pSOG35 is a transformation vector which utilizes the *E. coli* gene dihydrofolate reductase (DHFR) as a selectable marker conferring resistance to methotrexate. PCR was used to amplify the 35S promoter (~800 bp), intron 6 from the maize Adhl gene (~550 bp) and 18 bp of the GUS untranslated leader sequence from pSOG10. A 250 bp fragment encoding the *E. coli* dihydrofolate reductase type II gene was also amplified by PCR and these two PCR fragments were assembled with a SacI-PstI fragment from pBI221 (Clontech) which comprised the pUC19 vector backbone and the nopaline synthase terminator. Assembly of these fragments generated pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generated the vector pSOG35. pSOG19 and pSOG35 carry the pUC gene for ampicillin resistance and have HindIII, SphI, PaI and EcoRI sites available for the cloning of foreign sequences.

Example 15

Requirements for Construction of Plant Expression Cassettes

Gene sequences intended for expression in transgenic plants are firstly assembled in expression cassettes behind a suitable promoter and upstream of a suitable transcription terminator. These expression cassettes can then be easily transferred to the plant transformation vectors described above.

Promoter Selection: The selection of promoter used in expression cassettes will determine the spatial and temporal expression pattern of the transgene in the transgenic plant. Selected promoters will express transgenes in specific cell types (such as leaf epidermal cells, meosphyll cells, root cortex cells) or in specific tissues or organs (roots, leaves or flowers, for example) and this selection will reflect the desired location of biosynthesis of the polyketide antibiotic. Alternatively, the selected promoter may drive expression of the gene under a light-induced or other temporally regulated promoter. A further alternative is that the selected promoter be chemically regulated. This would provide the possibility of inducing the induction of the polyketide antibiotic only when desired and caused by treatment with a chemical inducer.

Transcriptional Terminators: A variety of transcriptional terminators are available for use in expression cassettes. These are responsible for the termination of transcription and those which are known to function in plants and include the CaMV 35S terminator, the tml terminator, the nopaline synthase terminator, the pea rbcS E9 terminator. These can be used in both monocoylyedons and dicotyledons.

Sequences for the Enhancement or Regulation of Expression: Numerous sequences have been found to enhance gene expression from within the transcriptional unit and these sequences can be used in conjunction with the genes of this invention to increase their expression in transgenic plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop 1: 1183–1200 (1987)). In the same experimental system, the intron from the maize bronze1 gene had a similar effect in enhancing expression (Callis et al., supra). Intron sequences have been routinely incorporated into plant transformation vectors, typically within the non-translated leader. A number of non-translated leader sequences derived from viruses are also known to enhance expression, and these are particularly effective in dicotyledonous cells. Specifically, leader sequences from Tobacco Mosaic Virus (TMV, the "Ω-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693–8711 (1987); Skuzeski et al. Plant Molec. Biol. 15; 65–79 (1990))

Targeting of the Gene Product Within the Cell: Various mechanisms for targeting gene products are known to exist in plants and the sequences controlling the functioning of these mechanisms have been characterized in some detail. For example, the targeting of gene products to the chloroplast is controlled by a signal sequence found at the aminoterminal end of various proteins and which is cleaved during chloroplast import yielding the mature protein (e.g. Comai et al. J. Biol. Chem. 263: 15104–15109 (1988)). These signal sequences can be fused to heterologous gene products to effect the import of heterologous products into the chloroplast (van den Broeck et al. Nature 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized.

Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting to cellular protein bodies has been described by Rogers et al. (Proc. Natl. Acad. Sci. U.S.A 82: 6512–6516 (1985)).

In addition sequences have been characterized which cause the targeting of gene products to other cell compartments. Aminoterminal sequences are responsible for targeting to the ER, the apoplast, and extracellular secretion from aleurone cells (Koehler & Ho, Plant Cell 2: 769–783 (1990) ). Additionally, aminoterminal sequences in conjunction with carboxyterminal sequences are responsible for vacuolar targeting of gene products (Shinshi et al. Plant Molec. Biol. 14: 357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the aminoterminal ATG of the transgene. The signal sequence selected should include the known cleavage site and the fusion constructed should take into account any amino acids after the cleavage site which are required for cleavage. In some cases this requirement may be fulfilled by the addition of a small number of amino acids between the cleavage site and the transgene ATG or alternatively replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) Methods in Chloroplast Molecular Biology, Elsevier. pp 1081–1091 (1982); Wasmann et al. Mol. Gem Genet. 205: 446–453 (1986)). These construction techniques are well known in the art and are equally applicable to mitochondria and peroxisomes. The choice of targeting which may be required for PKS genes will depend on the cellular localization of the precursor required as the starting point for a given pathway. This will usually be cytosolic or chloroplastic, although it may is some cases be mitochondrial or peroxisomal. The gene products of PKS genes will not normally require targeting to the ER, the apoplast or the vacuole.

The above described mechanisms for cellular targeting can be utilized not only in conjunction with their cognate promoters, but also in conjunction with heterologous promoters so as to effect a specific cell targeting goal under the transcriptional regulation of a promoter which has an expression pattern different to that of the promoter from which the targeting signal derives.

Example 16

Examples of Expression Cassette Construction

The present invention encompasses the expression of genes encoding polyketide antibiotics under the regulation of any promoter which is expressible in plants, regardless of the origin of the promoter.

Furthermore, the invention encompasses the use of any plant-expressible promoter in conjunction with any further sequences required or selected for the expression of the PKS gene. Such sequences include, but are not restricted to, transcriptional terminators, extraneous sequences to enhance expression (such as introns [e.g. Adh intron 1], viral sequences [e.g. TMV-Ω]), and sequences intended for the targeting of the gene product to specific organelles and cell compartments.

Constitutive Expression, the CaMV 35S Promoter: Construction of the plasmid pCGN1761 is described in Example 23 of the published patent application EP 0 392 225. pCGN1761 contains the "double" 35S promoter and the tml transcriptional terminator with a unique EcoRI site between the promoter and the terminator and has a pUC-type backbone. A derivative of pCGN1761 was constructed which has a modified polylinker which includes NotI and XhoI sites in addition to the existing EcoRI site. This derivative was designated pCGN1761ENX. pCGN1761ENX is useful for the cloning of cDNA sequences or gene sequences (including microbial ORF sequences) within its polylinker for the purposes of their expression under the control of the 35S promoter in transgenic plants. The entire 35S promoter-gene sequence-tml terminator cassette of such a construction can be excised by HindIII, SphI, SalI, and XbaI sites 5' to the promoter and XbaI, BamHI and BglII sites 3' to the terminator for transfer to transformation vectors such as those described above in example 35. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter.

Modification of pCGN1761ENX by Optimization of the Translational Initiation Site: For any of the constructions described in this section, modifications around the cloning sites can be made by the introduction of sequences which may enhance translation. This is particularly useful when genes derived from microorganisms are to be introduced into plant expression cassettes as these genes may not contain sequences adjacent to their initiating methionine which may be suitable for the initiation of translation in plants. In cases where genes derived from microorganisms are to be cloned into plant expression cassettes at their ATG it may be useful to modify the site of their insertion to optimize their expression. Modification of pCGN1761ENX is described by way of example to incorporate one of several optimized sequences for plant expression (e.g. Joshi, supra).

pCGN1761ENX is cleaved with SphI, treated with T4 DNA polymerase and religated, thus destroying the SphI site located 5' to the double 35S promoter. This generates vector pCGN1761ENX/Sph-. pCGN1761ENX/Sph- is cleaved with EcoRI, and ligated to an annealed molecular adaptor of the sequence 5'-AATTCTAAAGCATCCGATCGG-3'(SEQ ID NO:5)/5'-AATTCCGATCCGATCGGCATGCTTTA-3' (SEQ ID NO:6). This generates the vector pCGNSENX which incorporates the quasi-optimized plant translational initiation sequence TAAA-C adjacent to the ATG which is itself part of an SphI site which is suitable for cloning heterologous genes at their initiating methionine. Downstream of the SphI site, the EcoRI, NotI, and XhoI sites are retained.

An alternative vector is constructed which utilizes an NcoI site at the initiating ATG. This vector, designated pCGN 1761NENX is made by inserting an annealed molecular adaptor of the sequence 5'-AATTCTAAACCATGGCGATCGG-3' (SEQ ID NO:7)/5'AATTCCGATCGCCATGGTTTA-3' (SEQ ID NO:8) at the pCGN1761ENX EcoRI site. Thus, the vector includes the quasi-optimized sequence TAAACC adjacent to the initiating ATG which is within the NcoI site. Downstream sites are EcoRI, NotI, and XhoI. Prior to this manipulation, however, the two NcoI sites in the pCGN 1761ENX vector (at upstream positions of the 5' 35S promoter unit) are destroyed using similar techniques to those described above for SphI or alternatively using "inside-outside" PCR (Innes et al. PCR Protocols: A guide to methods and applications. Academic Press, New York (1990). This manipulation can be assayed for any possible detrimental effect on expression by insertion of any plant cDNA or reporter gene sequence into the cloning site followed by routine expression analysis in plants.

Expression under a Chemically Regulatable Promoter: This section describes the replacement of the double 35S promoter in pCGN1761ENX with any promoter of choice; by way of example the chemically regulated PR-1a promoter is described. The promoter of choice is preferably excised from its source by restriction enzymes, but can alternatively be PCR-amplified using primers which carry appropriate terminal restriction sites. Should PCR-amplification be undertaken, then the promoter should be resequenced to check for amplification errors after the cloning of the amplified promoter in the target vector. The chemically regulatable tobacco PR-1 a promoter is cleaved from plasmid pCIB1004 (see EP 0 332 104, example 21 for construction) and transferred to plasmid pCGN 1761ENX. pCIB 1004 is cleaved with NcoI and the resultant 3' overhang of the linearized fragment is rendered blunt by treatment with T4 DNA polymerase. The fragment is then cleaved with HindIII and the resultant PR-1a promoter containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1 a promoter and the tml terminator and an intervening polylinker with unique EcoRI and NotI sites. Selected PKS genes can be inserted into this vector, and the fusion products (i.e. promoter-gene-terminator) can subsequently be transferred to any selected transformation vector, including those described in this application.

Constitutive Expression, the Actin Promoter: Several isoforms of actin are known to be expressed in most cell types and consequently the actin promoter is a good choice for a constitutive promoter. In particular, the promoter from the rice Act1 gene has been cloned and characterized (McElroy et al. Plant Cell 2: 163–171 (1990)). A 1.3 kb fragment of the promoter was found to contain all the regulatory elements required for expression in rice protoplasts. Furthermore, numerous expression vectors based on the Act1 promoter have been constructed specifically for use in monocotyledons (McElroy et al. Mol. Gem Genet. 231: 150–160 (1991)). These incorporate the Act1-intron 1, Adh1 5' flanking sequence and Adh1-intron 1 (from the maize alcohol dehydrogenase gene) and sequence from the CaMV 35S promoter. Vectors showing highest expression were fusions of 35S and the Act1 intron or the Act1 5' flanking sequence and the Act1 intron. Optimization of sequences around the initiating ATG (of the GUS reporter gene) also enhanced expression. The promoter expression cassettes described by McElroy et al. (Mol. Gem Genet. 231: 150–160 (1991)) can be easily modified for the expression of PKS genes and are particularly suitable for use in monocotyledonous hosts. For example, promoter containing fragments can be removed from the McElroy constructions and used to replace the double 35S promoter in pCGN1761ENX, which is then available for the insertion or specific gene sequences. The fusion genes thus constructed can then be transferred to appropriate transformation vectors. In a separate report the rice Act1 promoter with its first intron has also been found to direct high expression in cultured barley cells (Chibbar et al. Plant Cell Rep. 12: 506–509 (1993)).

Constitutive Expression, the Ubiquitin Promoter: Ubiquitin is another gene product known to accumulate in many call types and its promoter has been cloned from several species for use in transgenic plants (e.g. sunflower—Binet et al. Plant Science 79: 87–94 (1991), maize—Christensen et al. Plant Molec. Biol. 12: 619–632 (1989)). The maize ubiquitin promoter has been developed in transgenic monocot systems and its sequence and vectors constructed for monocot transformation are disclosed in the patent publication EP 0 342 926 (to Lubrizol). Further, Taylor et al. (Plant Cell Rep. 12: 491–495 (1993)) describe a vector (pAHC25) which comprises the maize ubiquitin promoter and first intron and its high activity in cell suspensions of numerous monocotyledons when introduced via microprojectile bombardment. The ubiquitin promoter is clearly suitable for the expression of PKS genes in transgenic plants, especially monocotyledons. Suitable vectors are derivatives of pAHC25 or any of the transformation vectors described in this application, modified by the introduction of the appropriate ubiquitin promoter and/or intron sequences.

Root Specific Expression: A preferred pattern of expression for the polyketide antibiotics of the instant invention is root expression. Root expression is particularly useful for the control of soil-borne phytopathogens such as Rhizoctonia and Pythium. Expression of polyketide antibiotics only in root tissue would have the advantage of controlling root invading phytopathogens, without a concomitant accumulation of polyketide antibiotic in leaf and flower tissue and seeds. A suitable root promoter is that described by de Framond (FEBS 290: 103–106 (1991)) and also in the published patent application EP 0 452 269 (to Ciba-Geigy). This promoter is transferred to a suitable vector such as pCGN1761ENX for the insertion of an PKS gene of interest and subsequent transfer of the entire promoter-gene-terminator cassette to a transformation vector of interest.

Wound Inducible Promoters: Wound-inducible promoters are particularly suitable for the expression of PKS genes because they are typically active not just on wound induction, but also at the sites of phytopathogen infection. Numerous such promoters have been described (e.g. Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), Warner et al. Plant J. 3: 191–201 (1993)) and all are suitable for use with the instant invention. Logemann et al. (supra) describe the 5' upstream sequences of the dicotyledonous potato wun1 gene. Xu et al. (supra) show that a wound inducible promoter from the dicotyledon potato (pin2) is active in the monocotyledon rice. Further, Rohrmeier & Lehle (supra) describe the cloning of the maize Wip1 cDNA which is wound induced and which can be used to isolated the cognate promoter using standard techniques. Similarly, Firek et al. (supra) and Warner et al. (supra) have described a wound induced gene from the monocotyledon *Asparagus officinalis* which is expressed at local wound and pathogen invasion sites. Using cloning techniques well known in the art, these promoters can be transferred to suitable vectors, fused to the PKS genes of this invention, and used to express these genes at the sites of phytopathogen infection.

Pith Preferred Expression: Patent Application WO 93/07278 (to Ciba-Geigy) describes the isolation of the maize trpA gene which is preferentially expressed in pith cells. The gene sequence and promoter extend up to −1726 from the start of transcription are presented. Using standard molecular biological techniques, this promoter or parts thereof, can be transferred to a vector such as pCGN1761 where it can replace the 35S promoter and be used to drive the expression of a foreign gene in a pith-preferred manner. In fact fragments containing the pith-preferred promoter or parts thereof can be transferred to any vector and modified for utility in transgenic plants.

Pollen-Specific Expression: Patent Application WO 93/07278 (to Ciba-Geigy) further describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a foreign gene in a pollen-specific manner. In fact fragments containing the pollen-specific promoter or parts thereof can be transferred to any vector and modified for utility in transgenic plants.

Leaf-Specific Expression: A maize gene encoding phosphoenol carboxylase (PEPC) has been described by Hudspeth & Grula (Plant Molec Biol 12: 579–589 (1989)). Using standard molecular biological techniques the promoter for this gene can be used to drive the expression of any gene in a leaf-specific manner in transgenic plants.

Expression with Chloroplast Targeting: Chen & Jagendorf (J. Biol. Chem. 268: 2363–2367 (1993) have described the successful use of a chloroplast transit peptide for import of a heterologous transgene. This peptide used is the transit peptide from the rbcS gene from *Nicotiana plumbaginifolia* (Poulsen et al. Mol. Gen. Genet. 205: 193–200 (1986)). Using the restriction enzymes DraI and SphI, or Tsp509I and SphI the DNA sequence encoding this transit peptide can be excised from plasmid prbcS-8B (Poulsen et al. supra) and manipulated for use with any of the constructions described above. The DraI-SphI fragment extends from −58 relative to the initiating rbcS ATG to, and including, the first amino acid (also a methionine) of the mature peptide immediately after the import cleavage site, whereas the Tsp509I-SphI fragment extends from −8 relative to the initiating rbcS ATG to, and including, the first amino acid of the mature peptide. Thus, these fragment can be appropriately inserted into the polylinker of any chosen expression cassette generating a transcriptional fusion to the untranslated leader of the chosen promoter (e.g. 35S, PR-1a, actin, ubiquitin etc.), whilst enabling the insertion of a required PKS gene in correct fusion downstream of the transit peptide. Constructions of this kind are routine in the art. For example, whereas the DraI end is already blunt, the 5' Tsp509I site may be rendered blunt by T4 polymerase treatment, or may alternatively be ligated to a linker or adaptor sequence to facilitate its fusion to the chosen promoter. The 3' SphI site may be maintained as such, or may alternatively be ligated to adaptor of linker sequences to facilitate its insertion into the chosen vector in such a way as to make available appropriate restriction sites for the subsequent insertion of a selected PKS gene. Ideally the ATG of the SphI site is maintained and comprises the first ATG of the selected PKS gene. Chen & Jagendorf (supra) provide consensus sequences for ideal cleavage for chloroplast import, and in each case a methionine is preferred at the first position of the mature protein. At subsequent positions there is more variation and the amino acid may not be so critical. In any case, fusion constructions can be assessed for efficiency of import in vitro using the methods described by Bartlett et al. (In: Edelmann et al. (Eds.) Methods in Chloroplast Molecular Biology, Elsevier. pp 1081–1091 (1982)) and Wasmann et al. (Mol. Gen. Genet. 205: 446–453 (1986)). Typically the best approach may be to generate fusions using the selected PKS gene with no modifications at the aminoterminus, and only to incorporate modifications when it is apparent that such fusions are not chloroplast imported at high efficiency, in which case modifications may be made in accordance with the established literature (Chen & Jagendorf, supra; Wasman et al., supra; Ko & Ko, J. Biol. Chem. 267: 13910–13916 (1992)).

A preferred vector is constructed by transferring the DraI-SphI transit peptide encoding fragment from prbcS-8B to the cloning vector pCGN1761ENX/Sph-. This plasmid is cleaved with EcoRI and the termini rendered blunt by treatment with T4 DNA polymerase. Plasmid prbcS-8B is cleaved with SphI and ligated to an annealed molecular adaptor of the sequence 5'-CCAGCTGGAATTCCG-3' (SEQ ID NO:9)/5'-CGGAATTCCAGCTGGCATG-3' (SEQ ID NO:10). The resultant product is 5'-terminally phosphorylated by treatment with T4 kinase. Subsequent cleavage with DraI releases the transit peptide encoding fragment which is ligated into the blunt-end ex-EcoRI sites of the modified vector described above. Clones oriented with the 5' end of the insert adjacent to the 3' end of the 35S promoter are identified by sequencing. These clones carry a DNA fusion of the 35S leader sequence to the rbcS-8A promoter-transit peptide sequence extending from −58 relative to the rbcS ATG to the ATG of the mature protein, and including at that position a unique SphI site, and a newly created EcoRI site, as well as the existing NotI and XhoI sites of pCGN1761ENX. This new vector is designated pCGN1761/CT. DNA sequences are transferred to pCGN1761/CT in frame by amplification using PCR techniques and incorporation of an SphI, NsphI, or NlaIII site at the amplified ATG, which following restriction enzyme cleavage with the appropriate enzyme is ligated into SphI-cleaved pCGN1761/CT. To facilitate construction, it may be required to change the second amino acid of cloned gene, however, in almost all cases the use of PCR together with standard site directed mutagenesis will enable the construction of any desired sequence around the cleavage site and first methionine of the mature protein.

A further preferred vector is constructed by replacing the double 35S promoter of pCGN 1761ENX with the BamHI-SphI fragment of prbcS-8A which contains the full-length light regulated rbcS-8A promoter from −1038 (relative to the transcriptional start site) up to the first methionine of the mature protein. The modified pCGN1761 with the destroyed SphI site is cleaved with PstI and EcoRI and treated with T4 DNA polymerase to render termini blunt. prbcS-8A is cleaved SphI and ligated to the annealed molecular adaptor of the sequence described above. The resultant product is 5'-terminally phosphorylated by treatment with T4 kinase. Subsequent cleavage with BamHI releases the promoter-transit peptide containing fragment which is treated with T4 DNA polymerase to render the BamHI terminus blunt. The promoter-transit peptide fragment thus generated is cloned into the prepared pCGN1761ENX vector, generating a construction comprising the rbcS-8A promoter and transit peptide with an SphI site located at the cleavage site for insertion of heterologous genes. Further, downstream of the SphI site there are EcoRI (re-created), NotI, and XhoI cloning sites. This construction is designated pCGN1761 rbcS/CT.

Similar manipulations can be undertaken to utilize other GS2 chloroplast transit peptide encoding sequences from other sources (monocotyledonous and dicotyledonous) and from other genes. In addition, similar procedures can be followed to achieve targeting to other subcellular compartments such as mitochondria.

Example 17

Isolation of New Promoters Suitable for the Expression of PKS Genes

New promoters are isolated using standard molecular biological techniques including any of the techniques described below. Once isolated, they are fused to reporter genes such as GUS or LUC and their expression pattern in transgenic plants analyzed (Jefferson et al. EMBO J. 6: 3901–3907 (1987); Ow et al. Science 234: 856–859 (1986)). Promoters which show the desired expression pattern are fused to PKS genes for expression in planta.

Subtractive cDNA Cloning: Subtractive cDNA cloning techniques are useful for the generation of cDNA libraries enriched for a particular population of mRNAs (e.g. Hara et al. Nucl. Acids Res. 19: 1097–7104 (1991)). Recently, techniques have been described which allow the construction of subtractive libraries from small amounts of tissue (Sharma et al. Biotechniques 15: 610–612 (1993)). These techniques are suitable for the enrichment of messages specific for tissues which may be available only in small amounts such as the tissue immediately adjacent to wound or pathogen infection sites.

Differential Screening by Standard Plus/Minus Techniques: λ phage carrying cDNAs derived from different RNA populations (viz. mot versus whole plant, stem specific versus whole plant, local pathogen infection points versus whole plant, etc.) are plated at low density and transferred to two sets of hybridization filters (for a review of differential screening techniques see Calvet, Pediatr. Nephrol. 5: 751–757 (1991). cDNAs derived from the "choice" RNA population are hybridized to the first set and cDNAs from whole plant RNA are hybridized to the second set of filters. Plaques which hybridize to the first probe, but not to the second, are selected for further evaluation. They are picked and their cDNA used to screen Northern blots of "choice" RNA versus RNA from various other tissues and sources. Clones showing the required expression pattern are used to clone gene sequences from a genomic library to enable the isolation of the cognate promoter. Between 500 and 5000 bp of the cloned promoter is then fused to a reporter gene (e.g. GUS, LUC) and reintroduced into transgenic plants for expression analysis.

Differential Screening by Differential Display: RNA is isolated from different sources i.e. the choice source and whole plants as control, and subjected to the differential display technique of Liang and Pardee (Science 257: 967–971 (1992)). Amplified fragments which appear in the choice RNA, but not the control are gel purified and used as probes on Northern blots carrying different RNA samples as described above. Fragments which hybridize selectively to the required RNA are cloned and used as probes to isolate the cDNA and also a genomic DNA fragment from which the promoter can be isolated. The isolated promoter is fused to a the GUS or LUG reporter gene as described above to assess its expression pattern in transgenic plants.

Promoter Isolation Using "Promoter Trap" Technology: The insertion of promoterless reporter genes into transgenic plants can be used to identify sequences in a host plant which drive expression in desired cell types or with a desired strength. Variations of this technique is described by Ott &Chua (Mol. Caen. Genet. 223: 169–179 (1990)) and Kertbundit et al. (Proc. Natl. Acad. Sci. U.S.A 88: 5212–5216 (1991)). In standard transgenic experiments the same principle can be extended to identify enhancer elements in the host genome where a particular transgene may be expressed at particularly high levels.

Example 18

Transformation of Dicotyledons

Transformation techniques for dicotyledons are well known in the art and include Agrobacterium-based techniques and techniques which do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J 3: 2717–2722 (1984), Potrykus et al., Mol. Gen. Genet. 199: 169–177 (1985), Reich et al., Biotechnology 4: 1001–1004 (1986), and Klein et al., Nature 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. The many crop species which are routinely transformable by Agrobacterium include tobacco, tomato, sunflower, cotton, oilseed rape, potato, soybean, alfalfa and poplar (EP 0 317 511 (cotton [1313]), EP 0 249 432 (tomato, to Calgene), WO 87/07299 (Brassica, to Calgene), U.S. Pat. No. 4,795,855 (poplar)). Agrobacterium transformation typically involves the transfer of the binary vector carrying the foreign DNA of interest (e.g. pCIB200 or pCIB2001) to an appropriate Agrobacterium strain which may depend of the complement of vir genes carded by the host Agrobacterium strain either on a co-resident Ti plasmid or chromosomally (e.g. strain CIB542 for pCIB200 and pCIB2001 (Uknes et al. Plant Cell 5: 159–169 (1993)). The transfer of the recombinant binary vector to Agrobacterium is accomplished by a triparental mating procedure using E. coli carrying the recombinant binary vector, a helper E. coli strain which carries a plasmid such as pRK2013 and which is able to mobilize the recombinant binary vector to the target Agrobacterium strain. Alternatively, the recombinant binary vector can be transferred to Agrobacterium by DNA transformation (Höfgen & Willmitzer, Nucl. Acids Res. 16: 9877(1988)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Example 19

Transformation of Monocotyledons

Transformation of most monocotyledon species has now also become routine. Preferred techniques include direct gene transfer into protoplasts using PEG or electropotation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093–1096 (1986)).

Patent Applications EP 0 292 435 ([1280/1281] to Ciba-Geigy), EP 0 392 225 (to Ciba-Geigy) and WO 93/07278 (to Ciba-Geigy) describe techniques for the preparation of callus and protoplasts from an élite inbred line of maize, transformation of protoplasts using PEG or electroporation, and the regeneration of maize plants from transformed protoplasts. Gordon-Kamm et al. (Plant Cell 2: 603–618 (1990)) and Fromm et al. (Biotechnology 8: 833–839 (1990)) have published techniques for transformation of A188-derived maize line using particle bombardment. Furthermore, application WO 93/07278 (to Ciba-Geigy) and Koziel et al. (Biotechnology 11: 194–200 (1993)) describe techniques for the transformation of élite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al., Plant Cell Rep 7: 379–384 (1988); Shimamoto et al. Nature 338: 274–277 (1989); Datta et al. Biotechnology 8: 736–740 (1990)). Both types are also routinely transformable using particle bombardment (Chfistou et al. Biotechnology 9: 957–962 (1991)).

Patent Application EP 0 332 581 (to Ciba-Geigy) describes techniques for the generation, transformation and regeneration of Pooideae protoplasts. These techniques allow the transformation of Dactylis and wheat. Furthermore, wheat transformation was been described by Vasil et al. (Biotechnology 10: 667–674 (1992)) using particle bombardment into cells of type C long-term regenerable callus, and also by Vasil et al. (Biotechnology 11: 1553–1558 (1993)) and Weeks et al. (Plant Physiol. 102: 1077–1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashiga & Skoog, Physiologia Plantatum 15: 473–497 (1962)) and 3 mg/l 2,4-D for induction of somatic embryos which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to mover for about 24 h (still on osmoticum). After 24 hrs, the embryos are removed from the osmotieum and placed back onto induction medium where they stay for about a month before regeneration. Approximately one month later the embryo explants with developing embryogenie callus are transferred to regeneration medium (MS+1 mg/liter NAA, 5 mg/liter GA), further containing the appropriate selection agent (10 mg/l basra in the case of pCIB3064 and 2 mg/l methotrexate in the case of pSOG35). After approximately one month, developed shoots are transferred to larger sterile containers known as "GA7s" which contained half-strength MS, 2% sucrose, and the same concentration of selection agent. Application Ser. No. 08/147,161 describes methods for wheat transformation and is hereby incorporated by reference.

Example 20

Expression of Soraphen in Transgenic Plants

Clones pVKM15, pJL3, and p98/1 contain between them the entire minimal PKS genes, sorA and sorB, that are required for the synthesis of the minimal soraphen PKS structure which is proposed to be soraphen C. In addition, these plasmids contain other genes, including sorR and sorM that are likely to have roles in processing soraphen C to the final structure of soraphen A.

These genes are manipulated for expression in transgenic plants in the following manner. A DNA fragment is amplified from the aminoterminus of sorA using PCR and p98/1 as template. The 5' oligonucleotide primer includes either an SphI site or an NcoI site at the ATG for cloning into the vectors pCGN1761SENX or pCGNNENX respectively. Further, the 5' oligonucleotide includes either the base C (for SphI cloning) or the base G (for NcoI cloning) immediately after the ATG, and thus the second amino acid of the protein is changed either to a histidine or an aspartate (other amino acids can be selected for position 2 by additionally changing other bases of the second codon). The 3' oligonucleotide for the amplification is located at a convenient restriction site in sorA and incorporates a distal EcoRI site enabling the amplified fragment to be cleaved with SphI (or NcoI) and EcoRI, and then cloned into pCGN1761SENX (or pCGN1761NENX). To facilitate cleavage of the amplified fragments, each oligonucleotide includes several additional bases at its 5'. The oligonucleotides preferably have 12–30 bp homology to the template DNA, in addition to the required restriction sites and additional sequences. This manipulation fuses the aminoterminal ~112 amino acids of sorA or B at its ATG to the SphI or NcoI sites of the translation optimized vectors pCGN1761SENX or pCGN1761NENX in linkage to the double 35S promoter. The remainder of sorA or B is carded on three BglII fragments which can be sequentially cloned into the unique BglII site of the above-detailed constructions. The introduction of the first of these fragments is no problem, and requires only the cleavage of the aminoterminal construction with BglII followed by introduction of the first of these fragments. For the introduction of the two remaining fragments, partial digestion of the aminoterminal construction is required (since this construction now has an additional BglII site), followed by introduction of the next BglII fragment. Thus, it is possible to construct a vector containing the entire ~25 kb of sorA in operable fusion to the 35S promoter.

An alternative approach to constructing sorA by the fusion of sequential restriction fragments is to amplify the entire gene using PCR. Bames (Proc. Natl. Acad. Sci U.S.A 91: 2216–2220 (1994)) has recently described techniques for the high-fidelity amplification of fragments by PCR of up to 35 kb, and these techniques can be applied to sorA or B. Oligonucleotides specific for each end of sorA or B, with appropriate restriction sites added are used to amplify the entire coding region, which is then cloned into appropriate sites in a suitable vector such as pCGN1761 or its derivatives. Typically after PCR amplification, resequencing is advised to ensure that no base changes have arisen in the amplified sequence. Alternatively, a functional assay can be done directly in transgenic plants.

Yet another approach to the expression of the genes for polyketide biosynthesis (such as soraphen) in transgenic plants is the construction, for expression in plants, of transcriptional units which comprise less than the usual complement of modules, and to provide the remaining modules on other transcriptional units. As the biosynthesis of polyketide antibiotics such as soraphen is a process which requires the sequential activity of specific modules and that for the synthesis of a specific molecule these activities should be provided in a specific sequence, it is likely that the expression of different transgenes in a plant carrying different modules may lead to the biosynthesis of novel polyketide molecules because the sequential enzymatic nature of the wild-type genes is determined by their configuration on a single molecule. It is postulated that the localization of the three specific modules of sorA and five of sorB is determinatory in the biosynthesis of soraphen, and that the expression of, for example, three modules from sorB on one transgene and the other two on another, together with the sorA gene, may result in biosynthesis of a polyketide with a different molecular structure and possibly with a different antipathogenic activity. This invention encompasses all such deviations of module expression which may result in the synthesis in transgenic organisms of novel polyketides.

Fusions of the kind described above can be made to any desired promoter with or without modification (e.g. for optimized translational initiation in plants or for enhanced expression). As the genes identified for soraphen biosynthesis are around 70% GC rich it is not anticipated that the coding sequences should require modification to increase GC content for optimal expression in plants. It may, however, be advantageous to modify the genes to include codons preferred in the appropriate target plant species.

F. Analysis of Transgenic Plants for polyketide antibiotic Accumulation

Example 21

Analysis of PKS Gene Expression

Expression of PKS genes in transgenic plants can be analyzed using standard Northern blot techniques to assess the amount of PKS mRNA accumulating in tissues. Alternatively, the quantity of PKS gene product can be assessed by Western analysis using antisera raised to PKS gene products. Antisera can be raised using conventional techniques and proteins derived from the expression of PKS genes in a host such as *E. coli*. To avoid the raising of antisera to multiple gene products from *E. coil* expressing multiple PKS genes from multiple ORF operons, the PKS genes can be expressed individually in *E. coli*. Alternatively, antisera can be raised to synthetic peptides designed to be homologous or identical to known PKS predicted amino acid sequence. These techniques are well known in the art.

Example 22

Analysis of polyketide antibiotic Production in Transgenic Plants

For each polyketide antibiotic, known protocols are used to detect its production in transgenic plant tissue. These protocols are available in the appropriate polyketide literature. For soraphen the procedure described in Section A of the examples. Alternative techniques are described in Game & Brazhnikova (Lancet 247: 715 (1944)) and in the Merck Index (Merck & Co., Rahway, N.J. (1989)).

G. Assay of Disease Resistance in Transgenic Plants

Transgenic plants expressing APS biosynthetic genes are assayed for resistance to phytopathogens using techniques well known in phytopathology. For foliar pathogens, plants are grown in the greenhouse and at an appropriate stage of development inoculum of a phytopathogen of interest is introduced at in an appropriate manner. For soil-borne phytopathogens, the pathogen is normally introduced into the soil before or at the time the seeds are planted. The choice of plant cultivar selected for introduction of the genes should take into account relative phytopathogen sensitivity. Thus, it is preferred that the cultivar chosen will be susceptible to most phytopathogens of interest to allow a determination of enhanced resistance.

Assays of resistance to foliar and soil-borne phytopathogens as well as examples of important phytopathogens in agricultural crop species are presented in Examples 48–54 of U.S. application Ser. No. 08/258,261, now U.S. Pat. No. 5,614,395.

H. Assay of Biocontrol Efficacy in Microbial Strains Expressing PKS Genes

Examples of protecting cotton against *Rhizoctonia solani* and potato against *Claviceps michiganese subsp*. Speedonicum are presented in Examples 55 and 56 of U.S. application Ser. No. 08/258,261, now U.S. Pat. No. 5,614,393.

I. Isolation of Polyketide Antibiotics from Organisms Expressing the Cloned PKS Genes Extraction procedures for polyketide antibiotic isolation are given in Example 57 of U.S. application Ser. No. 08/258,261, now U.S. Pat. No. 5,614,395.

P. Formulation and Use of Isolated Antibiotics

Antifungal formulations can be made using active ingredients which comprise either the isolated APSs or alternatively suspensions or concentrates of cells which produce them. Formulations can be made in liquid or solid form. Examples of liquid and solid formulations of antifungal compositions are presented in Examples 58 and 59 of U.S. application Ser. No. 08/258,261, now U.S. Pat. No. 5,614,695.

While the present invention has been described with reference to specific embodiments thereof, it will be appreciated that numerous variations, modifications, and embodiments are possible, and accordingly, all such variations, modifications and embodiments are to be regarded as being within the spirit and scope of the present invention.

---

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 49377 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Sorangium cellulosum ( v i i ) IMMEDIATE SOURCE:
        ( B ) CLONE: p98/1, pJL3, and pVKM15

( i x ) FEATURE:
        ( A ) NAME/KEY: misc_feature
        ( B ) LOCATION: 383..760
        ( D ) OTHER INFORMATION: /product="SorR"
            / note="This gene encodes a protein that is highly
            homologous to the reductase domains of type I PKSs
            such as eryA from Saccharopolyspora erythraea."

( i x ) FEATURE:
        ( A ) NAME/KEY: misc_feature
        ( B ) LOCATION: 927..19874
        ( D ) OTHER INFORMATION: /product="SorA"

/ note="Gene product is highly homologous to type I
PKSs that are known to be involved in the synthesis
of polyketide compounds."

( i x ) FEATURE:
    ( A ) NAME/KEY: misc_feature
    ( B ) LOCATION: 942..7115
    ( D ) OTHER INFORMATION: /product="Module 1 of SorA"

( i x ) FEATURE:
    ( A ) NAME/KEY: misc_feature
    ( B ) LOCATION: 7203..12884
    ( D ) OTHER INFORMATION: /product="Module 2 of SorA"

( i x ) FEATURE:
    ( A ) NAME/KEY: misc_feature
    ( B ) LOCATION: 13455..19616
    ( D ) OTHER INFORMATION: /product="Module 3 of SorA"

( i x ) FEATURE:
    ( A ) NAME/KEY: misc_feature
    ( B ) LOCATION: 19871..46318
    ( D ) OTHER INFORMATION: /product="SorB"
        / note="Gene product is highly homologous to type I
        PKS genes."

( i x ) FEATURE:
    ( A ) NAME/KEY: misc_feature
    ( B ) LOCATION: 19870..24556
    ( D ) OTHER INFORMATION: /product="Module 1 of SorB"

( i x ) FEATURE:
    ( A ) NAME/KEY: misc_feature
    ( B ) LOCATION: 24638..30820
    ( D ) OTHER INFORMATION: /product="Module 2 of SorB"

( i x ) FEATURE:
    ( A ) NAME/KEY: misc_feature
    ( B ) LOCATION: 30881..35446
    ( D ) OTHER INFORMATION: /product="Module 3 of SorB"

( i x ) FEATURE:
    ( A ) NAME/KEY: misc_feature
    ( B ) LOCATION: 35528..40114
    ( D ) OTHER INFORMATION: /product="Module 4 of SorB"

( i x ) FEATURE:
    ( A ) NAME/KEY: misc_feature
    ( B ) LOCATION: 40190..46318
    ( D ) OTHER INFORMATION: /product="Module 5 of SorB"

( i x ) FEATURE:
    ( A ) NAME/KEY: misc_feature
    ( B ) LOCATION: 46851..47891
    ( D ) OTHER INFORMATION: /product="SorM"
        / note="The protein encoded by the sorM gene is highly
        homologous to the methyltransferase from Streptomyces
        hygroscopicus that is involved in the synthesis of the
        polyketide rappamicin."

( x i ) SEQUENCE DESCRIPTION: SEQ ID NO:1:

```
GCATGCGCCT CTGTAGGCAA AGTGATTCGT GGTTGACGAT CGCACGACTG CTCGACATTG      60

TGGCACCACT GCAGGTCACC GCGCGCCATC TGGTCGCCGG TATCCAGCGC CGCCAGCGCG     120

GGCTAGACCT GCAGCAGGAG GAGATCCGCG AGAGAAACGA GGCAATCCGG CTGCTCCGGC     180

CTCGCGAGGC GCGGGCCGCC CGGCCGTCCG GCTTGCGCCA GATCCAATCC TGCTCTAGAA     240

TCCTTCGGTG TCGCGGGACG ACCTCCTCGC CCGCCAGCGT TCCTCGTACC CGCGGCGAAT     300

GAGTGTAATT CACCATTTCT TCACGCGCCC GACACCTATC CGAGACGCGC CCGACACCTA     360

TCCGAGCTCG GAAAGAGCGT CCATGCTCGC GCAGGTTCGA TCAGGCTGCA CGCCCATGGT     420

GGTCGGTGTA GACGCCTTCC TCCTCTTCTC CTCGAGTGCA GGTGTCTTGG GGAGCGGGCT     480

GCAGGGCGCC TACTCGGCGG CCAACGCTTT CCTGGACGTG CTGTCCGAGC AGCCTCGCGT     540
```

```
CCTCGGACGG TCGGCCACGT CGATTGCCTG GTGCATATGG AACGGCGGAG GTATTGTCGA    600
CCACGCAGGC AAAGAGCATC TCAGAAGACG TGGCGTGTCC GTGATGCCGC TAGATCTCGC    660
CCTCGCGGCC TCGTATCGTG AGGAATCCAG GGGTGGGAGC CCGCAAAGAT CCTCACCCTC    720
ACTCTGCTCG CCCGTGCCAT CGAGCCGTTG TCCGGGATGA TCGAGGAAGT CTTGCCAGGC    780
AGCGGCGATC GGCGCCTCCA CTGGGAGGCG GGCTCACACC ACCGTGGCGC TGCCAGGCAA    840
CCACTTCAGC ATCACGAAGC GGCACGCCGA GCCCACCGCT CGAATCACCC ATAACTGGTT    900
CTCGACATCT GGGTCCTGAG GAGTTTATGA CAAAGGAGTA CACGCGTCCG CAGTCGGCGC    960
CGTTGACTGA GGGCGACCTC CTCACCTTGA TCGTCGCCCA TCTCGCGGAG CGGCTGCGCA   1020
TGGACGCGCG GTTCATCGAT GTCCACGAGC CCTTCAGCCG CCATGGGCTC GACTCACGCG   1080
GCGCGGTGGA CCTGGTCGTG GATCTGAGGA CGGCGCTTGG GCGCCCGCTG TCGCCCGTCG   1140
TGGTTTGGCA ACACCCGACT CCCGATGCCC TGGCCCGCCA CCTGGCCGGT GGGGCGGACG   1200
CGCGCGAGGG CCAAGCGCGC GCGGACTCTG CCTACGAGCG TCCTGGAGCA CCAAATGAGC   1260
CCATCGCGAT CGTCGGGATG GCCTGCCGGT TCCCGGGGGC GCCGGACGTG GACAGCTACT   1320
GGAGACTCCT ATCCGGCGGC GTGGATGCGG TCACCGAGGT GCCCGCTGGC CGGTGGGACA   1380
TGGACGCGTT CTACGATCGC GATCCTCGCT CTCTCGGCGA CGTGAGCACC CTCCGGGGCG   1440
GCTTCATCGA TGACGTCGAT CGCTTCGACG CGATGTTCTT CGGCATCTCT CCGCGAGAGG   1500
CCGTCTCCAT GGATCCACAG CAACGGCTCA TGCTGGAGCT CGCGTGGGAG GCCCTGGAAG   1560
ACGCGGGGAT CGTCGCGGAG AGGCTGAAGG AAAGTCTGAC CGGAGTCTTC TTCGGGTGCA   1620
TCTGGGACGA CTACGTCACG CTGATCCATC AGAGGGGGCG AGGAGCCATC GCCCAGCATA   1680
CGGTGACGGG GAATCACCGC AGCATCATCG CGAACCGCGT ATCGTACACG CTCGACCTGC   1740
GCGGTCCCAG CATGACGGTC GATTCGGCCT GCTCGTCCGC GCTCGTTACC ATACATATGG   1800
CCTGCGAGAG CCTGCGCAGC GGCGAGTCCA CATTGGCCCT CGCAGGCGGC GTCAACCTGA   1860
ACATAGCTCC CGAGAGCACG ATCGGTGTCC ACAAGTTCGG CGGCCTGTCC CCCGACGGCC   1920
GCTGCTTCAC CTTCGATGCG CGCGCGAACG GCTATGTGCG CGGCGAGGGG GGCGGCGTGG   1980
TGGTGCTCAA ACGCCTGTCC TCGGCCATCG CGGACGGCGA TCCATCATT TGTGTCATCC    2040
GCGGCTCCGC GGTCAACAAC GATGGTGCCA GCAACGGGTT GACCGGCCCC AATCCCCTGG   2100
CACAGGAAGC CGTCTTGCGG ACCGCGTACG AACGGGCAGG CGTGAACCCG GCCGATGTTC   2160
AGTATGTCGA GCTGCACGGA ACTGGCACCC AACTGGGGGA TCCCGTCGAG GCAAGCGCGC   2220
TCGGTGCAGT GCTCGGAAAG AGAAGGCCCG CCGAACGCCC GCTGCTCGTG GGATCCGCCA   2280
AGACCAACGT CGGGCACCTG GAAGGTGCCG CCGGCATCGT AGGGCTGCTC AAGGCAGCGC   2340
TCTGCCTCAA ACACAAGCAG CTCGCGCCCA ACCTCAACTT CGAGACCCCG AATCCGCACA   2400
TTCCATTCGC CGAGCTGAAT CTGAAGGTGC AGGGCGCTCT GGGGCCTTGG CCGGACATGG   2460
ATCGTCCGCT CGTTTGCGGC GTGAGTTCGT TCGGTCTGGG AGGGACGAAC GCGCACGTCG   2520
TGCTGTCGGA GTGGGCATCG CTCGAGGCCG AGCTCCACCC TCTCGCCGCA GAAAGCCCGG   2580
AGGCGCTGCG CGAAGAGGTG CAGCGGCGGC TCTTGACCAT GACCTCGCTC GTCGGGCGAG   2640
CACCCCTGTC GTTCCTGTGC GGTCGCTCGG CGGCACAGCG CTCTGCGAAG GAGCATCGCC   2700
TCGCGGTCAC CGCGCGCTCG TTCGAGGAGC TGAAGCAGCG TCTGCTAGGC TTTCTCGAGC   2760
ATGAGAAGCA CGTCTCCGTG TCGGCGGGGC GAGTGGATCT GGGCGCGGCG CCCAAGGTGG   2820
TCTTCGTCTT CGCCGGGCAG GGGGCGCAGT GGTTCGGCAT GGGTCGAGCG CTGCTGCAAC   2880
GCGAGCCCGT ATTCCGGACG ACGATCGAGC AGTGCAGCTC CTTCATCCAG CAGAACCTGG   2940
```

```
GCTGGTCGTT GCTCGATGAG CTGATGACAG ATCGGGAGAG CTCGCGGCTC GATGAGATCG    3000
ACGTCAGCCT CCCGGCCATC ATATCCATCG AGATCGCCCT GGCGGCGCAA TGGCGTGCTT    3060
GGGGCGTCGA GCCGGCGTTC GTAGTGGGCC ATAGCACAGG CGAGATCGCG GCGGCTCATG    3120
TCGCCGGCGT CCTGAGCATC GAGGACGCGA TGCGGACCAT CTGCGCGTAC GGGCGCATCA    3180
TCCGCAAGCT CCGAGGCAAG GGGGGCATGG GGCTCGTGGC GCTGTCGTGG AAGACGCTG    3240
GCAAGGAGCT GACCGGCTAC GAGGGGCGCC TCTTCCGCGC GATAGAGCAC AGCGCGGATT    3300
CAACGGTGCT GGCGGGCGAG CCGGACGCGC TCGACGCGCT GCTCCAGGCA CTGGAGCGGA    3360
AGAACGTCTT TTGTCGTCGA GTGGCGATGG ACGTTGCCCC CCATTGCCCC CAGGTCGACT    3420
GCCTTCGCGA CGAGTTGTTC GATGCGCTCC GTGAGGTGCG GCCCAACAAA GCGCAGATCC    3480
CCATCGTCTC CGAAGTGACG GGTACCGCGC TCGACGGCGA GCGCTTCGAC GCTTCCCACT    3540
GGGTCCGAAA TTTCGGCGAT CCTGCGCTCT TCTCCACGGC CATCGATCAT CTTTTGCAGG    3600
AAGGATTCGA CATCTTCCTG GAGCTCACGC CACATCCCCT CGCGCTACCT GCGATCGAGT    3660
CCAACCTGCG CCGGTCCGGC CGGCGTGGCG TCGTGCTCCC GTCGCTCCGC CGTAACGAGG    3720
ACGAGCGTGG GGTGATGCTG GACACGTTGG GCGTCCTCTA TGTGCGAGGC GCGCCGGTGC    3780
GGTGGGACAA TGTCTATCCG GCAGCCTTCG AGAGCATGCC TTTGCCCTCG ACGGCCGGTG    3840
GCGGGAAGCC GCTGCCACCC ATGCCCTGC TCATATCGGC CAGAACGGAC GCAGCCCTCG     3900
CTGCGCAAGC CGCGCGGCTG CGGGCGCACC TCGATTCTCA TCTCGACCTC GAGCTCGTGG    3960
ACGTCGCCTA TTCCCTCGCC GCCACGCGGA CGCACTTCGA GCGGCGCGCG GTGGTGGTCG    4020
CGCGCGATCG CGCGGGCATC CTCGATGGGC TGGACGCGCT CGCCCACGGC GGCTCCGCCG    4080
CCCTCCTCGG ACGGAGCGCC GCGCACGGAA AGCTCGCCAT TCTCTTTACG GGACAAGGAA    4140
GCCAGCGGCC CACCATGGGC CGAGCGCTCT ACGATGCTTT CCCCGTCTTC CGAGGTGCCC    4200
TCGACGCCGC CGCGGCTCAC CTCGACCGCG ACCTCGACCG CCCCTGCGC GACGTCCTCT     4260
TCGCTCCCGA CGGCTCCGAG CAGGCCGCGC GCCTCGACCA GACCGCCTTC ACCCAGCCGG    4320
CCCTGTTTGC CCTCGAAGTC GCCCTTTTTG AGCTTCTTCA ATCCTTCGGC CTAAAGCCCG    4380
CTCTCCTCCT CGGGCACTCC ATCGGGGAGC TCGTCGCCGC CCATGTCGCC GGCGTCCTTT    4440
CTCTCCAGGA CGCCTGCACT CTCGTCGCCG CCCGCGCGAA GCTCATGCAA GCGCTCCCAC    4500
AAGGCGGCGC CATGGTCACC CTCCAGGCCT CCGAGCAAGA AGCTCGCGAC CTGCTTCAGG    4560
CCGCGGAAGG ACGCGTCAGC CTCGCCGCCG TCAACGGACA TCTCTCCACC GTCGTCGCCG    4620
GCGACGAAGA CGCAGTGCTC AAGATCGCCC GGCAGGTCGA AGCCCTCGGA CGAAAGGCCA    4680
CACGCCTGCG CGTCAGCCAC GCCTTCCACT CCCCTCACAT GGACGGCATG CTCGACGACT    4740
TCCGCCGCGT CGCCCAGGGC CTCACCTTCC ATCCTGCGCG CATCCCCATC ATCTCCAACG    4800
TCACCGGCGC GCGCGCCACA GACCAGGAGC TGGCGTCGCC CGAAACTTGG GTCCGCCACG    4860
TCCGCGACAC CGTCCGCTTC CTCGACGGCG TCCGTACCCT CCACGCCGAA GGAGCACGCG    4920
CTTTCCTCGA GCTCGGGCCT CACCCTGTAC TCTCCGCCCT TGCGCAAGAC GCCCTCGGAC    4980
ACGACGAAGG CCCGTCGCCA TGCGCCTTCC TTCCCACCCT CCGCAAGGGA CGCGACGACG    5040
CCGAGGCGTT CACCGCCGCG CTCGGCGCTC TCCACGCTGC AGGGCTCACC CCCGACTGGA    5100
ACGCTTTCTT CGCGCCCTTC GCTCCATGCA AAGTCCCACT CCCCACCTAT ACCTTCCAGC    5160
GTGAGCGCTT CTGGCTCGAC GCCTCTACAG CACACGCCGC CAGCGCCACT CCCGCTGCGG    5220
CGCTCGAGGG GCGGTTCTGG CAAGCCGTCG AGAGCGGCGA CATCGACACA CTCAGCAGCG    5280
AGCTCCACGT GGACGGCGAT GAGCAGCGCG CCGCCCTTGC CCTCGTCCTT CCCACCCTCT    5340
```

```
CGAGCTTTCG CCACAAGCGG CAAGAGCAGA GCACGGTCGA TGCCTGGCGC TACCGCGTCA    5400
CCTGGAAGCC TCTGACCACC GCCGCCACGC CCGCCGACCT CGCCGGCACC TGGCTCCTCG    5460
TCGTGCCGTC CGCGCTGGGC GACGACGCGC TCCTCGCCAC GCTCACCGAG GCACTCACCC    5520
GGCGCGGAGC GCGCGTCCTC GCGCTGCGCG TGAGCGATAT CCACATAGGC CGCAGCGCTC    5580
TCGTCGAGCA CCTGCGCGAG GCTCTGGCGG AGACCGCCCC GCTGCGCGGC GTGCTCTCGC    5640
TCCTCGCCCT CGATGAGCAT CGCCTCGCGG ACCGTTCTGC TCTGCCCGCG GGTCTGGCCC    5700
TGTCGCTCGC CCTCGTCCAA GGCCTCGACG ACCTCGCCAT CGAGGCTCCC TTGTGGCTCT    5760
TCACCCGCGG CGCCGTCTCC ATCGGACACT CCGACCCCAT CACTCATCCC ACCCAGGCCA    5820
TGATCTGGGG CCTTGGCCGC GTCGTCGGCC TCGAGCACCC CGAGCGATGG GGCGGGCTCG    5880
TCGACGTCAG CGCTGGGGTC GACGAGAGCG CCGTGGGCCG CTTGCTCCCG GCCCTCGCCC    5940
AGCGCCACGA CGAAGACCAG CTCGCTCTCC GCCCGGCCGG ACTCTACGCT CGCCGCATCG    6000
TCCGTGCCCC GCTCGGCGAT GCGCCTCCCG CGCGGGAGTT TAGACCCCGA GGCACCATCC    6060
TCATCACCGG AGGCACCGGC GCCCTCGGCG CTCACGTCGC CCGATGGCTC GCTCGCCAGG    6120
GCGCAGAGCA CCTCATCCTC ATCAGCCGCC GAGGCGCCGA GGCCCTGGC GCCTCGGAGC     6180
TCCACGCCGA GCTCAATGCC CTCGGCGTCC GCACCACCCT CGCCGCGTGC GATGTCGCCG    6240
ATAGAAGCGC TCTCCAAGCT CTCCTCGACA GCATTCCGTC GGACTGCCCG CTCACGGCGG    6300
TGTTTCACAC GGCAGGAGCT CGCGACGATG GCCTGATCGG CGACATGACG CCCGAGCGCA    6360
TCGAGCGGGT CCTTGCGCCC AAGCTCGATT CGGCGTTGCA CTTGCACGAG CTCACGAAAA    6420
ATAGCGCTCT CGACGCCTTC GTCCTCTACG CTTCACTCTC GGGTGTCCTC GGCAATCCCG    6480
GTCAGGCCAA TTACGCCGCT GCAAACGCTT TCCTCGATGC CCTGGCCGAG CATCGGCGTA    6540
GCCTTGGACT GACGGCGACG TCCGTGGCGT GGGGCGGGTG GGCGGCGGT GGCATGGCCA     6600
CCGAGCGCGT GGCAGCCCAG CTCCAGCAAC GCGGGCTGTT GCAGATGGCC CCCTCGCTTG    6660
CCCTGGCGGC GCTCGCGCAA GCCCTGCAGC AAGACGAGAC CACCATCACT GTCGCCGATA    6720
TCGACTGGTC GCGCTTTGCG CCTGCGTTCA GCGTCGCTCG CCAGAGGCCG CTGCTGCGCG    6780
ATCTGCCAGA AGCGCAGCGG GCTCTCCAAG CCAGCGAAGG CGCGTCCTCC GAGCACGGCC    6840
CGGCCACGGG CCTGCTCGAC GAGCTCCGAA GCCGCTCGGA AAGCGAGCAG CTCGATCTGC    6900
TCGCAACGCT TGTGCGCGGC GAGACGGCCA CTGTCCTCGG CCACGCCGAG GCCTCCCATG    6960
TCGACCCCGA CAAGGGCTTC ATGGACCTCG GTCTCGATTC GCTCATGACC GTCGAGCTCC    7020
GCCGGCGCTT GCAAAAGGCC ACCGGCGTCA AGCTCCCGCC CACGCTCGCG TTCGATCACC    7080
CCTCTCCTCA TCGCGTCGCG TTTTTCTTGC GCGACTCGCT CGCCCGAGCC TTCGGCACGA    7140
GGCTCTCCGC CGAACGCGAC GGCGCCGCGC TCCCGGCTCC TGGCGCCACC AGCGACAGCG    7200
ACGAGCCGAT TGCCATCGTC GGCATGGCCC TCCGTCTGCC GGGCGGCATT GGCGATGTCG    7260
ACGCTCTTTG GGATTCCTC CACCAAGGAC GCGACGCGGT CGAGCCCATC CCACCTACCC     7320
GATGGGATGC CGGTGCCCTC TACGACCCTG ATCCCGACGC CAAGGCCAAG AGCTACGTCC    7380
GGCATGCTGC CATGCTCGAC CAGGTCGATC TCTTCGACCC TGGATTCTTT GGCATCAGCC    7440
CTCGTGAGGC CAAACACATC GACCCCCAGC ACCGCCTACT CCTCGAAGCT GCCTGGCAGG    7500
CCCTCGAAGA GGCCGGTATC GTCCCCTCCA CCCTCAAGGA TTCTCCCACC GGCGTGTTCG    7560
TCGGCATCGG CGCCAGCGAG TACGCGCCGC GGGAACCGGG CGCGGAGGAT TCCGAAGCTT    7620
ACATCGTCCA AGGCACTTAC GCGTCCTTTG CCGCGGGGCG CTTGGCCTTC ACGCTCGGGC    7680
TGCAAGGGCC AGCGCTCTCG GTCGACACCG CTTGCTCCTC CTCGCTCGTC GCCCTCCACC    7740
```

```
TCGCCTGCCA GGCCCTTCGC CGCGATGAGT GCAACCTCGC CCTCGCCGCA GGGGCCTCTG   7800
TCATGGTCTC TCCCGAGACC TTCGTCCTCC TTTCCCGCCT GCGCGCTTTG GCCCCCGACG   7860
GCCGCTCCAA GACCTTCTCG GCCAGCGCCG ACGGCTACGG TCGCGGTGAA GGCGTCATCG   7920
TCCTTGCCCT CGAGCGGCTC CGCGACGCCC TTGCCCAAGG ACGCCGCGTC CTCGCCGTCG   7980
TGCGCGGCAC CGCCGTCAAC CACGACGGCG CATCGAGCGG CATCACCGCC CCCAATGGCA   8040
CCTCCCAGAA GAAGGTCCTC CGCGCCGCGC TCCACGACGC CCGCATCGCT CCCGCCGATG   8100
TCGACGTCGT CGAGTGCCAT GGCACCGGCA CCTCCTTGGG CGATCCCATC GAGGTCCAAG   8160
CCCTGGCTGC TGTCTACGGT GAAGGCAGAT CCGCGGAAAA GCCTCTTTTT CTGGGTGCGG   8220
TCAAGACCAA CGTTGGCCAC CTCGAGGCCG CCGCCGGCCT CGCGGGCGTC GCCAAGATCG   8280
TCGCTTCCCT CCTGCACAAC GCCCTGCCCC CCACCCTCCA CACCACCCCA CGCAATCCCC   8340
TGATCGCGTG GGATGCGCTC GCCGTCGCCG TCGTCGATGC CACGAGGCCT TGGGTCCGCC   8400
ACGCGGATGG GCGTCCCCGC CGCGCCGGCG TCTCCGCCTT CGGACTCTCC GGCACCAACG   8460
CTCACGTCAT CCTCGAAGAG GCCCCCGCCA TCGCCCGGGT CGAGCCCGCA GCGTCACAGC   8520
CGGCGTCCGA GCCGCTTCCC GCAGCGTGGC CCGTGCTCCT GTCGGCCAAG AGCGAGGCGG   8580
CCGTGCGCGC CCAGGCAAAG CGGCTCCGCG ACCACCTCCT CGCCAAAAGC GAGCTCGCCC   8640
TCGCCGACGT GGCCTATTCG CTCGCGACCA CGCGCGCCCA CTTCGAGCAG CGCGCCGCTC   8700
TCCTCGTCAA AGGCCGCGAC GAGCTCCTCT CCGCCCTCGA TTCGCTGGCC CAAGGACATT   8760
CCGCCGCCGT GCTCGGACGA AGCGGCGCCC CAGGAAAGCT CGCCGTCCTC TTCACGGGGC   8820
AAGGAAGCCA GCGGCCCACC ATGGGCCGCG CCCTCTACGA CGCTTTCCCC GTCTTCCGGG   8880
ACGCCCTCGA CACCGTCGCC GCCCACCTCG ACCGCGACCT CGACCGCCCC CTGCGCGACG   8940
TCCTCTTCGC TCCCGACGGC TCCGAGCAGG CCGCGCGCCT CGACCAAACC GCCTTCACCC   9000
AGCCGGCCCT GTTTGCCCTC GAAGTCGCCC TCTTTCAGCT TCTCCAATCC TTCGGTCTGA   9060
AGCCCGCTCT CCTCCTCGGA CACTCCATTG GCGAGCTCGT CGCCGCCCAC GTCGCCGGCG   9120
TCCTTTCTCT CCAGGACGCC TGCACCCTCG TCGCCGCCCG CGCAAAGCTC ATGCAAGCGC   9180
TCCCACAAGG CGGCGCCATG GTCACCCTCC GAGCCTCCGA GGAGGAAGTC CGCGACCTTC   9240
TCCAGCCCTA CGATGGACGA GCTAGCCTCG CCGCCCTCAA TGGGCCTCTC TCCACCGTCG   9300
TCGCTGGCGA TGAAGACGCG GTGGTGGAGA TCGCCCGCCA GGCCGAAGCC CTCGGACGAA   9360
AGACCACACG CCTGCGCGTC AGCCACGCCT TCCACTCTCC GCACATGGAC GGAATGCTCG   9420
ACGACTTCCG CCGCGTCGCC CAGAGCCTCA CCTACCATCC GCACGCATC CCCATCATCT   9480
CCAACGTCAC CGGCGCGCGC GCCACGGACC ACGAGCTCGC CTCGCCCGAC TACTGGGTCC   9540
GCCACGTTCG CCACACCGTC CGCTTCCTCG ACGGCGTACG TGCCCTTCAC GCCGAAGGGG   9600
CACGCGTCTT TCTCGAGCTC GGGCCTCACG CTGTCCTCTC CGCCCTTGCG CAAGACGCCC   9660
TCGGACAGGA CGAAGGCACG TCGCCATGCG CCTTCCTTCC CACCCTCCGC AAGGGACGCG   9720
ACGACGCCGA GGCGTTCACC GCCGCGCTCG GCGCTCTCCA CGCTGCAGGG CTCACACCCG   9780
ACTGGAGCGC TTTCTTCGCC CCCTTCGCTC CACGCAAGGT CTCCCTCCCC ACCTATGCCT   9840
TCCAGCGCGA GCGCTTCTGG CTCGATGCCT CCAAGGCACA CGCTGCCGAC GTCGCCTCCG   9900
CAGGCCTGAC CTCGACCGAT CACCCGCTGC TCGGCGCCGG CGTCCCCTC GCCGACCGCG   9960
ATGGCTTCCT CTTCACAGGA CGACTCTCAC TCTCAGAGCA TCCGTGGCTC GCCGATCACG   10020
TCGTCTTCGG TACACCCATC CTTCCGGGCA CTGCCTTTCT CGAGCTTGCC CTGTTCGTCG   10080
CCGGTCGCGT CGGCCTCGAC ACCGTCGAAG AGCTCACCCT CGAAACCCCC CTCGCTCTCC   10140
```

```
CGTCTGAAGG CGCCCTCCTC GTCCAGGTGT CGGTCGGGCC TTTGGACGAC GCAGGACGAA    10200
GGCCACTCTC TCTTCACAGC CGACCCCAAG GCGCTCCTCA GGACGCCCCT TGGACTCGCC    10260
ACGCGAGCGG CTCGCTCGCT CCAGCTACCC CGTCCCCTTC CTTCGATCTC CACGACTGGC    10320
CTCCCTCGGG CGCCACCCAG GTAGACACCC AAGGCCTCTA CGCAACCCTC GAAAGCGCTG    10380
GGCTTGCCTA CGGCCCTCAG TTCCAGGGCC TCCGCTCGGT CTGGAGGCGC GGCGACGAGC    10440
TCTTTGCGGA AGCTCAGCTC CCGGACGCCG CCAAAAAGGA TGCCGCTCGG TTTGCCCTCC    10500
ACCCCGCCCT GCTCGACAGC GCCCTGCACG CGCTTGCCCT TGACGACGAG CGGGCACCGG    10560
GCGTCGCGCT GCCCTTCTCG TGGGGCGGAG TCTCTCTGCG CGCTGTCGGT GCCACCACGC    10620
TGCGCGTGCG CTTCCACCGT CCGAAAGGCG AAACCGCCGG CTCGCTCGTC CTCGCCGACG    10680
CCGCAGGCGG ACCCATCGCC TCGGTGCAAG CGCTCGCCAC GCGCATCACG TCCGCCGAGC    10740
AGCTCCGCAC CCCAGGAGCT TCCCACCACG ATGCCCTCTT CCGCGTCGAC TGGAGCGAGC    10800
TGCCGAGCCC CACCTCACCG TCTGGAGCCC CAAGCGCCGT CCTTCTCGGC ATCGGCGGCC    10860
TCGACCTCGC CCCCGAGGTG CCTCTCGCCC GCGTCGCCGA CCTCGCTGCC CTCCAGAGCG    10920
CGCTCGACCA AGGCGCTTCG CCTCCAGGCC TCGTCGTCGT CCCCTTCATG GCTAGAACCG    10980
CCGACGACCT CATCCAGAGC GCCCACTCCA TCACCGCGCG CGCCCTCGCC CTGCTGCAAG    11040
CCTGGCTGGC CGACGAACGC CTCGCCTCCT CGCGCCTCGT CCTGCTCACC CGACGCGCCA    11100
TCGCTGCCCG CGCCGATGAA GACGTCAAGG ACCTCGCTCA CGCCCCTCTC TGGGGGCTCG    11160
CACGCTCCGC GCAAAGCGAA CACCCAGAAC TCCCGCTCTT TCTCGTCGAC CTGGACCTCA    11220
GTGAGGCCTC CCAGCACACC CTGCTCGCCG CGCTCGAAAC AGGAGAGCGT CACTCGCGTC    11280
TCCGCAACGG AAAACCCTTC ATCCCGAGAT GGCGAATGC ACGCTCGAAG GATGAGCTCA     11340
TCGCCCCGGA CGCGTCCAAC TGGCGCCTCC ATATTCCGAC CAAAGGCAAC TTCGACGCGC    11400
TCACCCTCGT CGACGCCCCT CTAGCCCGTG CGCCCCTCGC ACACGGCCAA GTCCGCGTCG    11460
CCGTGCACGC CGCAGCCTTC AATTTCCGCG ATGTCCTCGA CACCCTTGGT CTGTATCCGG    11520
GCGACGCGGG ACCGCTCGGC GGCGAAGGCG CAGGCATCGT TACTGAAGTC GGTCCAGGTG    11580
TTTCGCGGTA CACCGTAGGC GACCGGGTGA TGGGATCTT CGGCGCAGCT GCGGTCCCA     11640
CGGCCATCGC CGACGCCCGC ATGATCTGCC CCATCCCCCA CGCCTGGTCC TTCGCCCAAG    11700
CCGCCAGCGT CCCCATCATC TATCTCACCG CCTACTACGG ACTCGTCGAT CTCGGGCATC    11760
TGAAACCCAA TCAACGTGTC CTCATCCATG CGGCCGCCGG CGGCGTCGGG ACGGCCGCCG    11820
TTCAGCTCGC ACGCCACCTC GGCGCCGAGG TCTTTGCCAC CGCCAGCGCA GGGAAGTGGA    11880
GCGCTCTCCG CGCGCTCGGC TTCGACGACG CGCACCTCGC GTCCTCACGT GACCTGGACT    11940
TCGAGCAGCA CTTCCTGCGC TCCACGCATG GGCGCGGCGT GGATGTCGTC CTCGACTGCT    12000
TGGCACGCGA GTTCGTCGAC GCTTCGCTGC GCCTCATGCC GAGCGGTGGA CGCTTCGTCG    12060
AGATGGGCAA GACGGACATC CGTGAGCCCG ACGCGGTCGG CGTCGCCTAC CCTGGTGTCG    12120
TTTACCGCGC CTTCGACCTC ATAGAGGCCG GACCGGATCG AATAGAGCAG ATGCTCGCAG    12180
AGCTGCTCAG CCTCTTCGAG CGCGGTGCGC TTCGTCCGCC GCCCATCACA TCTTGGGACA    12240
TCCGTCATGC CCCCCAGGCC TTTCGCGCGC TCGCTCAGGC GCGGCATGTT GGGAAGTTCG    12300
TCCTCACCAT ACCCGTCCC ATAGACCCCG AAGGCACCGT CCTCATCACG GGAGGCACCG     12360
GCACGCTAGG AGCCCTGGTC GCACGCCATC TCGTCGCAAG ACACGGCGCC AAGCACCTGC    12420
TTCTCACGTC GAGGCAGGGC GCGCACGCTC CGGGCGCCGA GGCCTCGCGA ACCGAGCTCG    12480
AAGCGCTGGG GGCCTCTGTC ACACTTCGCG CGTGCGACGC GGCCGACCCA CGCGCCCTCC    12540
```

| | | | | | | |
|---|---|---|---|---|---|---|
| AAGCCCTCTT | GGACTCCATC | CCGAGCGCTC | ACCCGCTCAC | CGCCGTCGTC | CACGCCGCGG | 12600 |
| GCGCCCTCGA | CGACGGCCTG | CTCGGCGCCA | TGAGCCCCGA | GCGCATCGAC | CGCGTCTTTG | 12660 |
| CCCCCAAGCT | CGATGCTGCT | TGGCACTTGC | ATGAGCTCAC | CCAAGACAAG | CCCCTCGCCG | 12720 |
| CCTTCGTCCT | CTTCTCGTCC | GCTGCTGGCG | TCCTTGGTAG | TCCAGGTCAG | TCGAACTACG | 12780 |
| CCGCGGCCAA | TGCCTTCCTC | GATGCGCTCG | CGCATCACCG | GCGTGCCCAC | GGGCTCCCGG | 12840 |
| CCTCCTCGCT | CGCATGGGGC | TATTGGGCCG | AGCGCAGTCG | AATGACCGAG | CACCTCAGCG | 12900 |
| CCGCCGATGT | TTCTCGCATG | AGGCGCGCCG | GCGTCCGGCC | CCTCGCCACA | GACGAGGCGC | 12960 |
| TCTCCCTCTT | CGATGCGGCT | CTCTTGCGGC | CCGAGCCCGC | CCTGGTCCCC | GCACGCTTCG | 13020 |
| ACGTGAACGC | GCTCGGCGCG | AATGCCGACG | AGGTGCCCCC | GCTGTTCCAG | CGTCTCGTCC | 13080 |
| GCGCTCGCGT | CGCACGCAAG | GCCGCCAGCA | ATACCGCCCT | GGCCTCTTCA | CTCTCTCAGC | 13140 |
| GCCTCTCCTC | CCTCCCGCCC | GCAGAAAGCG | AGCGCTTCCT | CCTCGATCTC | GTCCGCACCG | 13200 |
| AAGCCGCCAC | CGTCCTCGGC | CTCGCCTCAT | TCGAATCGCT | CGATCCCCAT | CGCCCTCTCC | 13260 |
| AAGAGCTCGG | CCTCGATTCT | CTTATCGCTC | TCGAGCTCCG | AGGTCGACTC | GCCGCGGCCA | 13320 |
| CCGGGCTGCG | ACTCCAACCT | ACTCTCCTCT | TCGACTATCC | AACCCCGGCT | GCACTCTCAC | 13380 |
| GCTTTTTCAC | GACGCAGTTC | TTCGGGGAAA | CCACCGACCG | TCCCGCAGCG | CCGCTCACCC | 13440 |
| CGGCGGGAAG | CGAAGACCCT | ATCGCCATCG | TGTCGATGAG | CTGCCGCTTC | CCTGGCGACG | 13500 |
| TGCGCACGCC | CGAGGATCTC | TGGAAGCTCT | TGCTCGATGG | GAAAGATGCC | ATCTCCAGCT | 13560 |
| TTCCCCAGAA | TCGCGGTTGG | AGTCTCGATG | CGCTCGACGC | TCCCGGTCGC | TTCCCAGTCC | 13620 |
| GAGAGGGAGG | CTTCGTCTAC | GACGCAGACG | CCTTCGATCC | GGCCTTCTTC | GGGATCAGTC | 13680 |
| CACGCGAAGC | GCTCGCCATC | GATCCCCAAC | AGCGGCTCCT | CCTCGAGATC | AGCTGGGAAG | 13740 |
| CGTTGGAGCG | TGCAGGCATC | GACCCGGCCT | CGCTCCAAGG | GAGCCAAAGC | GGCGTTTTCG | 13800 |
| TCGGCATTAT | ACACAACGAC | TACGGCGCAT | GGCTGATGAA | CGGGACTGAC | GAACACAAGG | 13860 |
| GATTCGCTGC | CACGGGTAGC | ACGGCGAGCG | TCGCCTCCGG | CCGGATCGCC | TATACGTTCG | 13920 |
| GCTTCCAAGG | GCCCGCCATC | AGCGTTGACA | CGGCGTGCAG | CTCCTCGCTC | GTCGCGGTTC | 13980 |
| ACCTCGCCTG | CCAGGCCCTC | CGGCACGGCG | AATGCTCCCT | GGCGCTCGCT | GGCGGCGTGA | 14040 |
| CCGTCCTGGC | CACGCCAGCA | GTCTTCGTCG | CGTTCGACTC | CGAGAGCGCG | GGTGCCCCCG | 14100 |
| ATGGTCGCTG | CAAGGCCTTC | TCGGCGGAAG | CGAACGGTGC | GGGCTGGGCC | GAGGGCGCCG | 14160 |
| GGATGCTCTT | GCTCGAGCGC | CTCTCCGATG | CGGTCCGAAA | CGGTCATCCC | GTCCTCGCCG | 14220 |
| TCCTTCGAGG | CTCCGCCGTC | AACCAAGACG | GCCGAAGCCA | GGGCCTCACC | GCGCCCAACG | 14280 |
| GCCCTGCCCA | GGAGCGGGTC | ATCCGGCAGG | CGCTCGACAG | CGCGCGGCTC | ACGCCAAAGG | 14340 |
| ACATCGACGC | CGTCGAGGCT | CACGGCACGG | GGACGACCCT | CGGAGACCCC | ATCGAGGCTC | 14400 |
| AAGCCATTCT | TGCCACCTAT | GGAGAGTCCC | ATTCCCAAGA | CAGCCCCCTC | TGGCTTGGAA | 14460 |
| GTCTCAAGTC | CAACATGGGA | CATACTCAGG | CCGCGGCCGG | CGTAGGAAGC | GTCATCAAGA | 14520 |
| TGGTGCTCGC | GTTGCAGCAC | GGTCTCTTGC | CCAAGACCCT | CCATGCCAAA | AACCCTTCCC | 14580 |
| CCCACATCGA | CTGGTCTCCG | GGCACGGTAA | AGCTCCTGGA | CGAGCCCGTC | GTCTGGAAGA | 14640 |
| CCAATGGGCA | TCCACGCCGC | GCTGGCGTCT | CCTCGTTCGG | GTTCTCCGGC | ACCAATGCCC | 14700 |
| ACGTCATCCT | CGAAGAGGCC | CCCGCCATCG | CCCGGGCCGA | GTCCGCCGCC | GCACAGCCTG | 14760 |
| CGTCCGAGCC | GCTTCCCGCA | GCGTGGCCCG | TGCTCCTTTC | AGCCAAGAGC | GAGGCGGCCC | 14820 |
| TGCGCGCGCA | GGCCGCGCGG | TTGCGGGACC | ACCTCCAGGC | ACACCCCGAC | CTCGAGCTCG | 14880 |
| CGGACGTCGC | CTATTCACTC | GCCACGACGC | GGGCGCACTT | CGAGCGGCGC | GCGGTGGTCG | 14940 |

| | | | | | |
|---|---|---|---|---|---|
| TCGCAAAGGA | CCGCGACGAG | GCCACCTTCG | CCCTCGATGC | CTTCGAGCAA | GGCAGCCCGG | 15000 |
| CCCACCACGT | CGCGCACGGC | GAAGCCAGGG | TCGCGGGCAA | GCTCGTCTTC | GTCTTTCCAG | 15060 |
| GCCAGGGATC | CCAGTGGCCC | GGAATGGCGC | AGCAACTGCT | CACGACATCC | GATGCGTTCC | 15120 |
| GCGCGCAAGT | CGAAGCGTGC | GCGCGCGCGT | TCGCACCTCA | CCTCGGCTGG | TCGCTCTTGG | 15180 |
| CCGTGCTCCG | CGGCGACGAG | GGGGCCCCGT | CGCTGGAGCG | GATCGAGGTC | GTGCAACCAG | 15240 |
| CGCTCTTCAC | CGTCATGGTC | TCCTTGGCTG | CCCTCTGGCG | CTCCAGGGGT | ATCGAGCCCG | 15300 |
| ATGCCGTCGT | TGGACACAGC | CAAGGCGAGC | TCGCCGCCGC | CTACGTGGCC | GGCGCGCTGT | 15360 |
| CGCTCGACGA | CGCCGCCAAG | GTGGTGGCAC | GGCGCAGCCG | CCTGCTGAGC | ACGCTCTCCG | 15420 |
| GTCAGGGCGC | GATGGCCGCC | GTGGAGCGGC | CGCCCGCGGC | GCTCGAGCCC | TACCTCGCGC | 15480 |
| GCTTCGGTCG | GCGCCTCTCC | ATCGCCGCCA | TCAACAGCCC | GAGCGCCACC | ACGGTCTCCG | 15540 |
| GCGAGCCCGA | CGCCATTGAC | CATCTGCTCC | GGCTGCTCAA | AGCCGAGCAG | ATCTTCGCGC | 15600 |
| TCAAGCTGCG | CGTCGACGTG | GCGTCCCACG | GCGCGCAGAT | CGAAGGCATG | CGCGAGCAGC | 15660 |
| TGCTCGAGGA | GCTCCGCGAG | ATCGAGCCGC | GGGAAAGCCG | AATTCCGTTC | TACTCCACGG | 15720 |
| TTCGAGGCGA | GAAGCTCGCC | GGTACCGAGC | TCGGCGCCGC | CTACTGGTAC | GACAACCTGC | 15780 |
| TGCGGCCCGT | CCGCTTCGCC | GACGCCACCC | AGCTCCTGCT | CGACGACGCG | CACCGCTTCT | 15840 |
| TCGTCGAGGT | GAGCCCCCAT | CCGGTGCTGA | TGCTGCCGCT | TGAGGAGACC | CTCGAAGCCT | 15900 |
| CCGGTCTCCC | CACGGCGGTC | CTTGGCTCGC | TCTGGCAGGA | CGAGGGGGAC | CTCTCGCGCT | 15960 |
| TTCTCGCTTC | GCTCGGCGAG | CTCTACGCGC | GCGGATACGC | CGTCGATTGG | CGCGCTTTCT | 16020 |
| TCGAGCCGCT | GCGGCCGCGT | CGCGTCGCTC | TGCCCACGTA | TGCCTTCCAG | CGCGAGCGCT | 16080 |
| TCTGGCTCGA | CGCCCCCACA | GCACACGCCG | ACGTCGCCTC | CGCAGGCCTG | ACCTCGGCCG | 16140 |
| ACCACCCGCT | GCTCGGCGCC | GCCGTCCGCC | TCGCCGACAC | CGATGCCTTC | CTCTTCACCG | 16200 |
| GCCGCCTCTC | GCTGCAGAGC | CATCCCTGGC | TCGCCGAGCA | CGCCGCCTTC | GGCATACCCA | 16260 |
| TCCTGCCGGG | CACCGCCTTT | CTCGAGCTTG | CCCTGCTCGC | CGCCGATCGC | GTCGGCCTCG | 16320 |
| ACACCGTCGA | AGAGGTCACG | CTCGAAGCTC | CCCTCGCTCT | CCCCTCTCAA | GGCACCATTC | 16380 |
| TCATCCAGAT | CTCCGTCGGA | CCCATGGACG | AGGCGGGACG | AAGGTCGCTC | TCCCTCCATG | 16440 |
| GCCGGACCGA | GGACGCTCCT | CAGGACGCCC | CTTGGACGCG | CCACGCGAGC | GGGTCGCTCG | 16500 |
| CTAAAGCTGC | CCCCTCCCTC | TCCTTCGATC | TTCACGAATG | GGCTCCTCCG | GGGGCACGC | 16560 |
| CGGTGGACAC | CCAAGGCTCT | TACGCAGGCC | TCGAAAGCGG | GGGGCTCGCC | TATGGGCCTC | 16620 |
| AGTTCCAGGG | ACTTCGCTCC | GTCTGGAAGC | GCGGCGACGA | GCTCTTCGCC | GAGGCCAAGC | 16680 |
| TCCCGGACGC | AGGCGCCAAG | GATGCCGCTC | GGTTCGCCCT | CCACCCCGCC | CTGTTCGACA | 16740 |
| GCGCCCTGCA | CGCGCTTGTC | CTTGAAGACG | AGCGGACGCC | GGGCGTCGCT | CTGCCCTTCT | 16800 |
| CGTGGAGAGG | AGTCTCGCTG | CGCTCCGTCG | GCGCCACCAC | CCTGCGCGTG | CGCTTCCATC | 16860 |
| GTCCGAATGG | CAAGTCCTCC | GTGTCGCTCC | TCCTCGGCGA | CGCCGCAGGC | GAGCCCCTCG | 16920 |
| CCTCGGTCCA | AGCGCTCGCC | ACGCGCATCA | CGTCCCAGGA | GCAGCTCCGC | ACCCAGGGAG | 16980 |
| CTTCCCTCCA | CGATGCTCTC | TTCCGGGTTG | TCTGGAGAGA | TCTGCCCAGC | CCTACGTCGC | 17040 |
| TCTCTGAGGC | CCCGAAGGGT | GTCCTCCTAG | AGACAGGGGG | TCTCGACCTC | GCGCTGCAGG | 17100 |
| CGTCTCTCGC | CCGCTACGAC | GGTCTCGCTG | CCCTCCGGAG | CGCGCTCGAC | CAAGGCGCTT | 17160 |
| CGCCTCCGGG | CCTCGTCGTC | GTCCCCTTCA | TCGATTCGCC | CTCTGGCGAC | CTCATAGAGA | 17220 |
| GCGCTCACAA | CTCCACCGCG | CGCGCCCTCG | CCTTGCTGCA | AGCGTGGCTT | GACGACGAAC | 17280 |
| GCCTCGCCTC | CTCGCGCCCTC | GTCCTGCTCA | CCCGACAGGC | CATCGCAACC | CACCCCGACG | 17340 |

-continued

| | | | | | |
|---|---|---|---|---|---|
| AGGACGTCCT | CGACCTCCCT | CACGCTCCTC | TCTGGGGCCT | TGTGCGCACC | GCGCAAAGCG | 17400 |
| AACACCCGGA | GCTCCCTCTC | TTCCTCGTCG | ACCTGGACCT | CGGTCAGGCC | TCGGAGCGCG | 17460 |
| CCCTGCTCGG | CGCGCTCGAC | ACAGGAGAGC | GTCAGCTCGC | TCTCCGCCAT | GGAAAATGCC | 17520 |
| TCGTCCCGAG | GTTGGTGAAT | GCACGCTCGA | CAGAGGCGCT | CATCGCGCCG | AACGTATCCA | 17580 |
| CGTGGAGCCT | TCATATCCCG | ACCAAAGGCA | CCTTCGACTC | GCTCGCCCTC | GTCGACGCTC | 17640 |
| CTCTAGCCCG | TGCGCCCCTC | GCACAAGGCC | AAGTCCGCGT | CGCCGTGCAC | GCGGCAGGTC | 17700 |
| TCAACTTCCG | CGATGTCCTC | AACACCCTTG | GCATGCTTCC | GGACAACGCG | GGGCCGCTCG | 17760 |
| GCGGCGAAGG | CGCGGGCATT | GTCACCGAAG | TCGGCCCAGG | TGTTTCCCGA | TACACTGTAG | 17820 |
| GCGACCGGGT | GATGGGCATC | TTCCGCGGAG | GCTTTGGCCC | CACGGTCGTC | GCCGACGCCC | 17880 |
| GCATGATCTG | CCCCATCCCC | GATGCCTGGT | CCTTCGTCCA | AGCCGCCAGC | GTCCCCGTCG | 17940 |
| TCTTTCTCAC | CGCCTACTAT | GGACTCGTCG | ATGTCGGGCA | TCTCAAGCCC | AATCAACGTG | 18000 |
| TCCTCATCCA | TGCGGCCGCA | GGCGGCGTCG | GTACTGCCGC | CGTCCAGCTC | GCGCGCCACC | 18060 |
| TCGGCGCCGA | AGTCTTCGCC | ACCGCCAGTC | CAGGGAAGTG | GGACGCTCTG | CGCGCGCTCG | 18120 |
| GCTTCGACGA | TGCGCACCTC | GCGTCCTCAC | GTGACCTGGA | ATTCGAGCAG | CATTTCCTGC | 18180 |
| GCTCCACACG | AGGGCGCGGC | ATGGATGTCG | TCCTCAACGC | CTTGGCGCGC | GAGTTCGTCG | 18240 |
| ACGCTTCGCT | GCGTCTCCTG | CCGAGCGGTG | GAAGCTTTGT | CGAGATGGGC | AAGACGGATA | 18300 |
| TCCGCGAGCC | CGACGCCGTA | GGCCTCGCCT | ACCCCGGCGT | CGTTTACCGC | GCCTTCGATC | 18360 |
| TCTTGGAGGC | TGGACCGGAT | CGAATTCAAG | AGATGCTCGC | AGAGCTGCTC | GACCTGTTCG | 18420 |
| AGCGCGGCGT | GCTTCGTCCG | CCGCCCATCA | CGTCCTGGGA | CATCCGGCAT | GCCCCCCAGG | 18480 |
| CGTTCCGCGC | GCTCGCTCAG | GCGCGGCATA | TTGGAAAGTT | CGTCCTCACC | GTTCCCGTCC | 18540 |
| CATCGATCCC | CGAAGGCACC | ATCCTCGTCA | CGGGAGGCAC | CGGCACGCTC | GGCGCGCTCA | 18600 |
| TCGCGCGCCA | CCTCGTCGCC | AATCGCGGCG | ACAAGCACCT | GCTCCTCACC | TCGCGAAAGG | 18660 |
| GTGCGAGCGC | TCCGGGGGCC | GAGGCATTGC | GGAGCGAGCT | CGAAGCTCTG | GGGGCTGCGG | 18720 |
| TCACGCTCGC | CCGGTGCGAC | GCGGCCGATC | CACGCGCGCT | CCAAGCCCTC | TTGGACAGCA | 18780 |
| TCCCGAGCGC | TCACCCGCTC | ACGGCCGTCG | TGCACGCCGC | CGGCGCCCTT | GACGATGGGC | 18840 |
| TGATCAGCGA | CATGAGCCCC | GAGCGCATCG | ACCGCGTCTT | TGCTCCCAAG | CTCGACGCCG | 18900 |
| CTTGGCACTT | GCATCAGCTC | ACCCAGGACA | AGGCCGCTCG | GGGCTTCGTC | CTCTTCTCGT | 18960 |
| CCGCCTCCGG | CGTCCTCGGC | GGTATGGGTC | AATCCAACTA | CGCGGGGGGC | AATGCGTTCC | 19020 |
| TTGACGCGCT | CGCGCATCAC | CGACGCGTCC | ATGGGCTCCC | AGGCTCCTCG | CTCGCATGGG | 19080 |
| GCCATTGGGC | CGAGCGCAGC | GGAATGACCC | GACAACCTCA | GCGGCGTCGA | TACCGCTCGC | 19140 |
| ATGAGGCGCG | CGGTCTCCGA | TCCATCGCCT | CGGACGAGGG | TCTCGCCCTC | TTCGATATGG | 19200 |
| CGCTCGGGCG | CCCGGAGCCC | GCGCTGGTCC | CCGCCCGCTT | CGACATGAAC | GCGCTCGGCG | 19260 |
| CGAAGGCCGA | CGGGCTACCC | TCGATGTTCC | AGGGTCTCGT | CCGCGCTCGC | GTCGCGCGCA | 19320 |
| AGGTCGCCAG | CAATAATGCC | CTGGCCGCGT | CGCTCACCCA | GCGCCTCGCC | TCCCTCCCGC | 19380 |
| CCACCGACCG | CGAGCGCATG | CTGCTCGATC | TCGTCCGCGC | CGAAGCCGCC | ATCGTCCTCG | 19440 |
| GCCTCGCCTC | GTTCGAATCG | CTCGATCCCC | GTCGCCCTCT | TCAAGAGCTC | GGTCTCGATT | 19500 |
| CCCTCATGGC | CATCGAGCTC | CGAAATCGAC | TCGCCGCCGC | CACAGGCTTG | CGACTCCAAG | 19560 |
| CCACCCTCCT | CTTCGACCAC | CCGACGCCCG | CCGCGCTCGC | GACCCTGCTG | CTCGGGAAGC | 19620 |
| TCCTCCAGCA | TGAAGCTGCC | GATCCTCGCC | CCTTGGCCGC | AGAGCTCGAC | AGGCTAGAGG | 19680 |
| CCACTCTCTC | CGCGATAGCC | GTGGACGCTC | AAGCACGCCC | GAAGATCATA | TTACGCCTGC | 19740 |

| | | | | | |
|---|---|---|---|---|---|
| AATCCTGGTT | GTCGAAGTGG | AGCGACGCTC | AGGCTGCCGA | CGCTGGACCG | ATTCTCGGCA | 19800 |
| AGGATTTCAA | GTCTGCTACG | AAGGAAGAGC | TCTTCGCTGC | TTGTGACGAA | GCGTTCGGAG | 19860 |
| GCCTGGGTAA | ATGAATAACG | ACGAGAAGCT | TGTCTCCTAC | CTACAGCAGG | CGATGAATGA | 19920 |
| GCTTCAGCGT | GCTCATCAGC | CCCTCCGCGC | GGTCGAAGAG | AAGGAGCACG | AGCCCATCGC | 19980 |
| CATCGTGGCG | ATGAGCTGCC | GCTTCCGGG | CGACGTGCGC | ACGCCCGAGG | ATCTCTGGAA | 20040 |
| GCTCTTGCTC | GATGGGAAAG | ATGCTATCTC | CGACCTTCCC | CCAAACCGTG | GTTGGAAGCT | 20100 |
| CGACGCGCTC | GACGTCCACG | GTCGCTCCCC | AGTCGAGAG | GGAGGCTTCT | TCTACGACGC | 20160 |
| AGACGCCTTC | GATCCGGCCT | TCTTCGGGAT | CAGCCCACGC | GAGGCGCTCG | CCATCGATCC | 20220 |
| CCAGCAGCGG | CTCCTCCTCG | AGATCTCATG | GGAAGCCTTC | GAGCGTGCGG | GCATCGACCC | 20280 |
| TGCCTCGCTC | CAAGGGAGCC | AAAGCGGCGT | CTTCGTCGGC | GTGATACACA | ACGACTACGA | 20340 |
| CGCATTGCTG | GAGAACGCAG | CTGGCGAACA | CAAAGGATTC | GTTTCCACCG | GCAGCACAGC | 20400 |
| GAGCGTCGCC | TCCGGCCGGA | TCGCGTATAC | ATTCGGCTTT | CAAGGGCCCG | CCATCAGCGT | 20460 |
| GGACACGGCG | TGCAGCTCCT | CGCTCGTCGC | GGTTCACCTC | GCCTGCCAGG | CCCTGCGCCG | 20520 |
| TGGCGAATGC | TCCCTGGCGC | TCGCCGGCGG | CGTGACCGTC | ATGGCCACGC | CAGCAGTCTT | 20580 |
| CGTCGCGTTC | GATTCCGAGA | GCGCGGGCGC | CCCCGATGGT | CGCTGCAAGT | CGTTCTCGGT | 20640 |
| GGAGGCCAAC | GGTTCGGGCT | GGGCCGAGGG | CGCCGGGATG | CTCCTGCTCG | AGCGCCTCTC | 20700 |
| CGATGCCGTC | CAAAACGGTC | ATCCCGTCCT | CGCCGTCCTT | CGAGGCTCCG | CCGTCAACCA | 20760 |
| GGACGGCCGG | AGCCAAGGCC | TCACCGCGCC | CAATGGCCCT | GCCCAAGAGC | GCGTCATCCG | 20820 |
| GCAAGCGCTC | GACAGCGCGC | GGCTCACTCC | AAAGGACGTC | GACGTCGTCG | AGGCTCACGG | 20880 |
| CACGGGAACC | ACCCTCGGAG | ACCCCATCGA | GGCACAGGCC | ATTCTTGCCA | CCTATGGCGA | 20940 |
| GGCCCATTCC | CAAGACAGAC | CCCTCTGGCT | TGGAAGTCTC | AAGTCCAACC | TGGGACATGC | 21000 |
| TCAGGCCGCG | GCCGGCGTGG | GAAGCGTCAT | CAAGATGGTG | CTCGCGTTGC | AGCAAGGCCT | 21060 |
| CTTGCCCAAG | ACCCTCCATG | CCCAGAATCC | CTCCCCCAC | ATCGACTGGT | CTCCGGGCAC | 21120 |
| GGTAAAGCTC | CTGAACGAGC | CCGTCGTCTG | GACGACCAAC | GGGCATCCTC | GCCACGCCGG | 21180 |
| CGTCTCCGCC | TTCGGCATCT | CCGGCACCAA | CGCCCACGTC | ATCCTCGAAG | AGGCCCCCGC | 21240 |
| CATCGCCCGG | GTCGAGCCCG | CAGCGTCACA | GCCCGCGTCC | GAGCCGCTTC | CCGCAGCGTG | 21300 |
| GCCCGTGCTC | CTGTCGGCCA | AGAGCGAGGC | GGCCGTGCGC | GCCCAGGCAA | AGCGGCTCCG | 21360 |
| CGACCACCTC | CTCGCCAAAA | GCGAGCTCGC | CCTCGCCGAT | GTGGCCTATT | CGCTCGCGAC | 21420 |
| CACGCGCGCC | CACTTCGAGC | AGCGCGCCGC | TCTCCTCGTC | AAAGGCCGCG | ACGAGCTCCT | 21480 |
| CTCCGCCCTC | GATGCGCTGG | CCCAAGGACA | TTCCGCCGCC | GTGCTCGGAC | GAAGCGGGGC | 21540 |
| CCCAGGAAAG | CTCGCCGTCC | TCTTCACGGG | GCAAGGAAGC | CAGCGGCCCA | CCATGGGCCG | 21600 |
| CGGCCTCTAC | GACGTTTTCC | CCGTCTTCCG | GGACGCCCTC | GACACCGTCG | GCGCCCACCT | 21660 |
| CGACCGCGAG | CTCGACCGCC | CCCTGCGCGA | CGTCCTCTTC | GCTCCCGACG | GCTCCGAGCA | 21720 |
| GGCCGCGCGC | CTCGAGCAAA | CCGCCTTCAC | CCAGCCGGCC | CTGTTTGCCC | TCGAAGTCGC | 21780 |
| CCTCTTTCAG | CTTCTACAAT | CCTTCGGTCT | GAAGCCCGCT | CTCCTCCTCG | GACACTCCAT | 21840 |
| TGGCGAGCTC | GTCGCCGCCC | ACGTCGCCGG | CGTCCTTTCT | CTCCAGGACG | GCTGCACCCT | 21900 |
| CGTCGCCGCC | CGCGCAAAGC | TCATGCAAGC | GCTCCCACAA | GGCGGCGCCA | TGGTCACCCT | 21960 |
| CCGAGCCTCC | GAGGAGGAAG | TCCGCGACCT | TCTCCAGCCC | TACGAAGGCC | GAGCTAGCCT | 22020 |
| CGCCGCCCTC | AATGGGCCTC | TCTCCACCGT | CGTCGCTGGC | GATGAAGACG | CGGTGGTGGA | 22080 |
| GATCGCCCGC | CAGGCCGAAG | CCCTCGGACG | AAAGACCACA | CGCCTGCGCG | TCAGCCACGC | 22140 |

| | | | | | |
|---|---|---|---|---|---|
| CTTCCATTCC | CCGCACATGG | ACGGAATGCT | CGACGACTTC | CGCCGCGTCG | CCCAGAGCCT  22200 |
| CACCTACCAT | CCCGCACGCA | TCCCCATCAT | CTCCAACGTC | ACCGGCGCGC | GCGCCACGGA  22260 |
| CCACGAGCTC | GCCTCGCCCG | ACTACTGGGT | CCGCCACGTT | CGCCACACCG | TCCGCTTCCT  22320 |
| CGACGGCGTA | CGTGCCCTTC | ACGCCGAAGG | GGCACGTGTC | TTTCTGAGC  | TCGGGCCTCA  22380 |
| CGCTGTCCTC | TCCGCCCTTG | CGCAAGACGC | CCTCGGACAG | GACGAAGGCA | CGTCGCCATG  22440 |
| CGCCTTCCTT | CCCACCCTCC | GCAAGGGACG | CGACGACGCC | GAGGCGTTCA | CCGCCGCGCT  22500 |
| CGGCGCTCTC | CACTCCGCAG | GCATCACACC | CGACTGGAGC | GCTTCTTCG  | CCCCCTTCGC  22560 |
| TCCACGCAAG | GTCTCCCTCC | CCACCTATGC | CTTCCAGCGC | GAGCGCTTCT | GGCCCGACGC  22620 |
| CTCCAAGGCA | CCCGGCGCCG | ACGTCAGCCA | CCTTGCTCCG | CTCGAGGGGG | GGCTCTGGCA  22680 |
| AGCCATCGAG | CGCGGGGACC | TCGATGCGCT | CAGCGGTCAG | CTCCACGTGG | ACGGCGACGA  22740 |
| GCGGCGCGCC | GCGCTCGCCC | TGCTCCTTCC | CACCCTCTCG | AGCTTTCGCC | ACGAGCGGCA  22800 |
| AGAGCAGAGC | ACGGTCGACG | CCTGGCGCTA | CCGTATCACC | TGGAAGCCTC | TGACCACCGC  22860 |
| CGAAACACCC | GCCGACCTCG | CCGGCACCTG | GCTCGTCGTC | GTGCCGGCCG | CTCTGGACGA  22920 |
| CGACGCGCTC | CCCTCCGCGC | TCACCGAGGC | GCTCACCCGG | CGCGGCGCGC | GCGTCCTCGC  22980 |
| CTTGCGCCTG | AGCCAGGCCC | ACCTGGACCG | CGAGGCTCTC | GCCGAGCATC | TGCGCCAGGC  23040 |
| TTGCGCCGAG | ACCGCCCCGA | TTCGCGGCGT | GCTCTCGCTC | CTCGCCCTCG | ACGAGCGCCC  23100 |
| CCTCGCAGAC | CGTCCTGCCC | TGCCCGCCGG | ACTCGCCCTC | TCGCTTTCTC | TCGCTCAAGC  23160 |
| CCTCGGCGAC | CTCGACCTCG | AGGCGCCCTT | GTGGTTCTTC | ACGCGCGGCG | CCGTCTCCAT  23220 |
| TGGACACTCT | GACCCCCTCG | CCCATCCCGC | CCAGGCCATG | ACCTGGGGCT | TGGGCCGCGT  23280 |
| CATCGGCCTC | GAGCACCCCG | ACCGGTGGGG | AGGTCTCGTC | GACGTCTGCG | CTGGGGTCGA  23340 |
| CGAGAGCGCC | GTGGGCCGCT | TGCTGCCGGC | CCTCGCCGAG | CGCCACGACG | AAGACCAGCT  23400 |
| CGCTCTCCGC | CCGGCCGGAC | TCTACGCTCG | CCGCATCGTC | CGCGCCCCGC | TCGGCGATGC  23460 |
| GCCTCCCGCG | CGCGACTTCA | CGCCCGGAGG | CACCATTCTC | ATCACCGGCG | GCACCGGCGC  23520 |
| CATTGGCGCT | CACGTCGCCC | GATGGCTCGC | TCGAAGAGGC | GCTCAGCACC | TCGTCCTCAT  23580 |
| CAGCCGCCGA | GGCGCCGAGG | CCCCTGGCGC | CTCGGAGCTC | CACGACGAGC | TCTCGGCCCT  23640 |
| CGGCGCGCGC | ACCACCCTCG | CCGCGTGCGA | TGTCGCCGAC | CGGAATGCTG | TCGCCACGCT  23700 |
| TCTTGAGCAG | CTCGACGCCG | AAGGGTCGCA | GGTCCGCGCC | GTGTTCCACG | CGAGCGGCAT  23760 |
| CGAACACCAC | GCTCCGCTCG | ACGCCACCTC | TTTCAGGGAT | CTCGCCGAGG | TTGTCTCCGG  23820 |
| CAAGGTCGAA | GGTGCAAAGC | ACCTCCACGA | CCTGCTCGGC | TCTCGACCCC | TCGACGCCTT  23880 |
| TGTTCTCTTT | TCGTCCGGCG | CGGCCGTCTG | GGGCGGCGGA | CAGCAAGGCG | GCTACGCGGC  23940 |
| CGCAAACGCC | TTCCTCGACG | CCCTTGCCGA | GCATCGGCGC | AGCGCTGGAT | TGACAGCGAC  24000 |
| GTCGGTGGCC | TGGGCGCGT  | GGGCGGCGG  | CGGCATGGCC | ACCGATCAGG | CGGCAGCCCA  24060 |
| CCTCCAACAG | CGCGGTCTGT | CGCGGATGGC | CCCCTCGCTT | GCCCTGGCGG | CGCTCGCGCT  24120 |
| GGCTCTGGAG | CACGACGAGA | CCACCGTCAC | CGTCGCCGAC | ATCGACTGGG | CGCGCTTTGC  24180 |
| GCCTTCGTTC | AGCGCCGCTC | GCCCCCGCCC | GCTCCTGCGC | GATTTGCCCG | AGGCGCAGCG  24240 |
| CGCTCTCGAG | ACCAGCGAAG | GCGCGTCCTC | CGAGCATGGC | CCGGCCCCCG | ACCTCCTCGA  24300 |
| CAAGCTCCGG | AGCCGCTCGG | AGAGCGAGCA | GCTTCGTCTG | CTCGTCTCGC | TGGTGCGCCA  24360 |
| CGAGACGGCC | CTCGTCCTCG | GCCACGAAGG | CGCCTCCCAT | GTCGACCCCG | ACAAGGGCTT  24420 |
| CCTCGATCTC | GGTCTCGATT | CGCTCATGGC | CGTCGAGCTT | CGCCGGCGCT | TGCAACAGGC  24480 |
| CACCGGCATC | AAGCTCCCGG | CCACCCTCGC | CTTCGACCAT | CCCTCTCCTC | ATCGAGTCGC  24540 |

```
GCTCTTCTTG CGCGACTCGC TCGCCCACGC CCTCGGCACG AGGCTCTCCG TCGAGCCCGA    24600
CGCCGCCGCG CTCCCGGCGC TTCGCGCCGC GAGCGACGAG CCCATCGCCA TCGTCGGCAT    24660
GGCCCTCCGC CTGCCGGGCG GCGTCGGCGA TGTCGACGCT CTTTGGGAGT TCCTGGCCCA    24720
GGGACGCGAC GGCGTCGAGC CCATTCCAAA GGCCCGATGG GATGCCGCTG CGCTCTACGA    24780
CCCCGACCCC GACGCCAAGA CCAAGAGCTA CGTCCGGCAT GCCGCCATGC TCGACCAGGT    24840
CGACCTCTTC GACCCTGCCT TCTTTGGCAT CAGCCCCCGG GAGGCCAAAC ACCTCGACCC    24900
CCAGCACCGC CTGCTCCTCG AATCTGCCTG GCAGGCCCTC GAAGACGCCG GCATCGTCCC    24960
CCCCACCCTC AAGGATTCCC CCACCGGCGT CTTCGTCGGC ATCGGCGCCA GCGAATACGC    25020
ATTGCGAGAG GCGAGCACCG AAGATTCCGA CGCTTATGCC CTCCAAGGCA CCGCCGGGTC    25080
CTTTGCCGCG GGGCGCTTGG CCTACACGCT CGGCCTGCAA GGGCCCGCGC TCTCGGTCGA    25140
CACCGCCTGC TCCTCCTCGC TCGTCGCCCT CCACCTCGCC TGCCAAGCCC TCCGACAGGG    25200
CGAGTGCAAC CTCGCCCTCG CCGCGGGCGT CTCCGTCATG GCCTCCCCG  AGGGCTTCGT    25260
CCTCCTTTCC CGCCTGCGCG CCTTGGCGCC CGACGGCCGC TCCAAGACCT TCTCGGCCAA    25320
CGCCGACGGC TACGGACGCG GAGAAGGCGT CATCGTCCTT GCCCTCGAGC GGCTCGGTGA    25380
CGCCCTCGCC CGAGGACACC GCGTCCTCGC CCTCGTCCGC GGCACCGCCA TCAACCACGA    25440
CGGCGCGTCG AGCGGTATCA CCGCCCCCAA CGGCACCTCC CAGCAGAAGG TCCTCCGCGC    25500
CGCGCTCCAC GACGCCCGCA TCACCCCCGC CGACGTCGAC GTCGTCGAGT GCCATGGCAC    25560
CGGCACCTCC TTGGGAGACC CCATCGAGGT GCAAGCCCTG GCCGCCGTCT ACGCCGACGG    25620
CAGACCCGCT GAAAAGCCTC TCCTTCTCGG CGCGCTCAAG ACCAACATCG GCATCTCGA     25680
GGCCGCCTCC GGCCTCGCGG GCGTCGCCAA GATCGTCGCC TCCCTCCGCC ATGACGCCCT    25740
GCCCCCCACC CTCCACACGG GCCCGCGCAA TCCCTTGATT GATTGGGATA CACTCGCCAT    25800
CGACGTCGTT GATACCCCGA GGTCTTGGGC CCGCCACGAA GATAGCAGTC CCGCCGCGC     25860
CGGCGTCTCC GCCTTCGGAC TCTCCGGCAC CAACGCCCAC GTCATCCTCG AGGAGGCTCC    25920
CGCCGCCCTG TCGGGCGAGC CCGCCACCTC ACAGACGGCG TCGCGACCGC TCCCCGCGGC    25980
GTGTGCCGTG CTCCTGTCGG CCAGGAGCGA GGCCGCCGTC CGCGCCCAGG CGAAGCGGCT    26040
CCGCGACCAC CTCCTCGCCC ACGACGACCT CGCCCTTATC GATGTGGCCT ATTCGCAGGC    26100
CACCACCCGC GCCCACTTCG AGCACCGCGC CGCTCTCCTG GCCCGCGACC GCGACGAGCT    26160
CCTCTCCGCG CTCGACTCGC TCGCCCAGGA CAAGCCCGCC CCGAGCACCG TTCTCGGCCG    26220
GAGCGGAAGC CACGGCAAGG TCGTCTTCGT CTTTCCTGGG CAAGGCTCGC AGTGGGAAGG    26280
GATGGCCCTC TCCCTGCTCG ACTCCTCGCC GGTCTTCCGC GCTCAGCTCG AAGCATGCGA    26340
GCGCGCGCTC GCTCCTCACG TCGAGTGGAG CCTGCTCGCC GTCCTGCGCC GCGACGAGGG    26400
CGCCCCCTCC CTCGACCGCG TCGACGTCGT ACAGCCCGCC CTCTTTGCCG TCATGGTCTC    26460
CCTGGCCGCC CTCTGGCGCT CGCTCGGCGT CGAGCCCGCC GCCGTCGTCG GCCACAGCCA    26520
GGGCGAGATC GCCGCCGCCT TCGTCGCAGG CGCTCTCTCC CTCGAGGACG CGGCGCGCAT    26580
CGCCGCCCTG CGCAGGAAAG CGCTCACCAC CGTCGGCGGC AACGGCGGCA TGGCCGCCGT    26640
CGAGCTCGGC GCCTCCGACC TCCAGACCTA CCTCGCTCCC TGGGGCGACA GGCTCTCCAC    26700
CGCCGCCGTC AACAGCCCCA GGGCTACCCT CGTATCCGGC GAGCCCGCCG CCGTCGACGC    26760
GCTGCTCGAC GTCCTCACCG CCACCAAGGT GTTCGCCCGC AAGATCCGCG TCGACTACGC    26820
CTCCCACTCC GCCCAGATGG ACGCCGTCCA AGACGAGCTC GCCGCAGGTC TAGCCAACAT    26880
CGCTCCTCGG ACGTGCGAGC TCCCTCTTTA TTCGACCGTC ACCGGCACCA GGCTCGACGG    26940
```

```
CTCCGAGCTC GACGGCGCGT ACTGGTATCG AAACCTCCGG CAAACCGTCC TGTTCTCGAG    27000
CGCGACCGAG CGGCTCCTCG ACGATGGGCA TCGCTTCTCC GTCGAGGTCA GCCCCCATCC    27060
CGTGCTCACG CTCGCCCTCC GCGAGACCTG CGAGCGCTCA CCGCTCGATC CCGTCGTCGT    27120
CGGCTCCATT CGACGAGAAG AAGGCCACCT CGCCCGCCTG CTCCTCTCCT GGGCGGAGCT    27180
CTCTACCCGA GGCCTCGCGC TCGACTGGAA GGACTTCTTC GCGCCCTACG CTCCCCGCAA    27240
GGTCTCCCTC CCCACCTACC CCTTCCAGCG AGAGCGGTTC TGGCTCGACG TCTCCACGGA    27300
CGAACGCTTC CGACGTCGCC TCCGCAGGCC TGACCTCGGC CGACCAATCC CGCTGCTCGG    27360
CGCCGCCGTC GCCTTCGCCG ACCGCGGTGG CTTTCTCTTT ACAGGGCGGC TCTCCCTCGC    27420
AGAGCACCCG TGGCTCGAAG GCCATGCCGT CTTCGGCACA CCCATCCTAC CGGGCACCGG    27480
CTTTCTCGAG CTCGCCCTGC ACGTCGCCCA CCGCGTCGGC CTCGACACCG TCGAAGAGCT    27540
CACGCTCGAG GCCCCTCTCG CTCTCCCATC GCAGGACACC GTCCTCCTCC AGATCTCCGT    27600
CGGGCCCGTG GACGACGCAG GACGAAGGGC GCTCTCTTTC CATAGCCGAC AAGAGGACGC    27660
GCTTCAGGAT GGCCCCTGGA CTCGCCACGC CAGCGGCTCT CTCTCGCCGG CGACCCCATC    27720
CCTCTCCGCC GATCTCCACG AGTGGCCTCC CTCGAGTGCC ATCCGGTGG ACCTCGAAGG     27780
CCTCTACGCA ACCCTCGCCA ACCTCGGGCT TGCCTACGGC CCCGAGTTCC AGGGCCTCCG    27840
CTCCGTCTAC AAGCGCGGCG ACGAGCTCTT TGCCGAAGCC AAGCTCCCGG AAGCGGCCGA    27900
AAAGGATGCC GCCCGGTTTG CCCTCCACCC TGCGCTGCTC GACAGCGCCC TGCATGCACT    27960
GGCCTTTGAG GACGAGCAGA GAGGGACGGT CGCTCTGCCC TTCTCGTGGA GCGGAGTCTC    28020
GCTGCGCTCC GTCGGTGCCA CCACCTTGCG CGTGCGCTTC CACCGTCCCA AGGGTGAATC    28080
CTCCGTCTCG ATCGTCCTGG CCGACGCCGC AGGTGACCCT CTTGCCTCGG TGCAAGCGCT    28140
CGCCATGCGG ACGACGTCCG CCGCGCAGCT CCGCACCCCG GCAGCTTCCC ACCATGATGC    28200
GCTCTTCCGC GTCGACTGGA GCGAGCTCCA AAGCCCCACT TCACCGCCTG CCGCCCCGAG    28260
CGGCGTCCTT CTCGGCACAG GCGGCCACGA TCTCGCGCTC GACGCCCCGC TCGCCCGCTA    28320
CGCCGACCTC GCTGCCCTCC GAAGCGCCCT CGACCAGGGC GCTTCGCCTC CCGGCCTCGT    28380
CGTCGCCCCC TTCATCGATC GACCGGCAGG CGACCTCGTC CCGAGCGCCC ACGAGGCCAC    28440
CGCGCTCGCA CTCGCCCTCT TGCAAGCCTG GCTCGCCGAC GAACGCCTCG CCTCGTCGCG    28500
CCTCGTCCTC GTCACCCGAC GCGCCGTCGC CACCCACACC GAAGACGACG TCAAGGACCT    28560
CGCTCACGCG CCGCTCTGGG GGCTCGCGCG CTCCGCGCAA AGTGAGCACC CAGACCTCCC    28620
GCTCTTCCTC GTCGACATCG ACCTCAGCGA GGCCTCCCAG CAGGCCCTGC TAGGCGCGCT    28680
CGACACAGGA GAACGCCAGC TCGCCCTCCG CAACGGGAAA CCCCTCATCC CGAGGTTGGC    28740
GCAACCACGC TCGACGGACG CGCTCATCCC GCCGCAAGCA CCCACGTGGC GCCTCCATAT    28800
TCCGACCAAA GGCACCTTCG ACGCGCTCGC CCTCGTCGAC GCCCCGAGG CCCAGGCGCC     28860
CCTCGCACAC GGCCAAGTCC GCATCGCCGT GCACGCGGCA GGGCTCAACT TCCGCGATGT    28920
CGTCGACACC CTTGGCATGT ATCCGGGCGA CGCGCCGCCG CTCGGAGGCG AAGGCGCGGG    28980
CATCGTTACT GAAGTCGGTC CAGGTGTCTC CCGATACACC GTAGGCGACC GGGTGATGGG    29040
GGTCTTCGGC GCAGCCTTTG GTCCCACGGC CATCGCCGAC GCCCGCATGA TCTGCCCCAT    29100
CCCCCACGCC TGGTCCTTCG CCCAAGCCGC CAGCGTCCCC ATCATCTATC TCACCGCCTA    29160
CTATGGACTC GTCGATCTCG GGCATCTGAA ACCCAATCAA CGTGTCCTCA TCCATGCGGC    29220
CGCCGGCGGC GTCGGGACGG CCGCCGTTCA GCTCGCACGC CACCTCGGCG CCGAGGTCTT    29280
TGCCACCGCC AGTCCAGGGA AGTGGAGCGC TCTCCGCGCG CTCGGCTTCG ACGATGCGCA    29340
```

```
CCTCGCGTCC TCACGTGACC TGGGCTTCGA GCAGCACTTC CTGCGCTCCA CGCATGGGCG   29400
CGGCATGGAT GTCGTCCTCG ACTGTCTGGC ACGCGAGTTC GTCGACGCCT CGCTGCGCCT   29460
CATGCCGAGC GGTGGACGCT TCATCGAGAT GGGAAAGACG GACATCCGTG AGCCCGACGC   29520
GATCGGCCTC GCCTACCCTG GCGTCGTTTA CCGCGCCTTC GACGTCACAG AGGCCGGACC   29580
GGATCGAATT GGGCAGATGC TCGCAGAGCT GCTCAGCCTC TTCGAGCGCG GTGTGCTTCG   29640
TCTGCCACCC ATCACATCCT GGGACATCCG TCATGCCCCC CAGGCCTTCC GCGCGCTCGC   29700
CCAGGCGCGG CATGTTGGGA AGTTCGTCCT CACCATTCCC CGTCCGATCG ATCCCGAGGG   29760
GACCGTCCTC ATCACGGGAG GCACCGGGAC GCTAGGAGTC CTGGTCGCAC GCCACCTCGT   29820
CGCGAAACAC AGCGCCAAAC ACCTGCTCCT CACCTCGAGG AAGGGCGCGC GTGCTCCGGG   29880
CGCGGAGGCT CTGCGAAGCG AGCTCGAAGC GCTGGGGGCC TCGGTCACCC TCGTCGCGTG   29940
CGACGTGGCC GACCCACGCG CCCTCCGGAC CCTCCTGGAC AGCATCCCGA GGGATCATCC   30000
GATCACGGCC GTCGTGCACG CCGCCGGCGC CCTCGACGAC GGGCCGCTCG GTAGCATGAG   30060
CGCCGAGCGC ATCGCTCGCG TCTTTGACCC CAAGCTCGAT GCCGCTTGGT ACTTGCATGA   30120
GCTCACCCAG GACGAGCCGG TCGCGGCCTT CGTCCTCTTC TCGGCCGCCT CCGGCGTCCT   30180
TGGTGGTCCA GGTCAGTCGA ACTACGCCGC TGCCAATGCC TTCCTCGATG CGCTCGCACA   30240
TCACCGGCGC GCCCAAGGAC TCCCAGCCGC TTCGCTCGCC TGGGGCTACT GGGCCGAGCG   30300
CAGTGGGATG ACCCGGCACC TCAGCGCCGC CGACGCCGCT CGCATGAGGC GCGCCGGCGT   30360
CCGGCCCCTC GACACTGACG AGGCGCTCTC CCTCTTCGAT GTGGCTCTCT TGCGACCCGA   30420
GCCCGCTCTG GTCCCCGCCC CCTTCGACTA CAACGTGCTC AGCACGAGTG CCGACGGCGT   30480
GCCCCCGCTG TTCCAGCGTC TCGTCCGCGC TCGCATCGCG CGCAAGGCCG CCAGCAATAC   30540
TGCCCTCGCC TCGTCGCTTG CAGAGCACCT CTCCTCCCTC CCGCCCGCCG AACGCGAGCG   30600
CGTCCTCCTC GATCTCGTCC GCACCGAAGC CGCCTCCGTC CTCGGCCTCG CCTCGTTCGA   30660
ATCGCTCGAT CCCCATCGCC CTCTACAAGA GCTCGGCCTC GATTCCCTCA TGGCCCTCGA   30720
GCTCCGAAAT CGACTCGCCG CCGCCGCCGG GCTGCGGCTC CAGGCTACTC TCCTCTTCGA   30780
CTATCCAACC CCGACTGCGC TCTCACGCTT TTTCACGACG CATCTCTTCG GGGGAACCAC   30840
CCACCGCCCC GGCGTACCGC TCACCCCGGG GGGGAGCGAA GACCCTATCG CCATCGTGGC   30900
GATGAGCTGC CGCTTCCCGG GCGACGTGCG CACGCCCGAG GATCTCTGGA AGCTCTTGCT   30960
CGACGGACAA GATGCCATCT CCGGCTTTCC CCAAAATCGC GGCTGGAGTC TCGATGCGCT   31020
CGACGCCCCC GGTCGCTTCC CAGTCCGGGA GGGGGGCTTC GTCTACGACG CAGACGCCTT   31080
CGATCCGGCC TTCTTCGGGA TCAGTCCACG TGAAGCGCTC GCCGTTGATC CCCAACAGCG   31140
CATTTTGCTC GAGATCACAT GGGAAGCCTT CGAGCGTGCA GGCATCGACC CGGCCTCCCT   31200
CCAAGGAAGC CAAAGCGGGG TCTTCGTTGG CGTATGGCAG AGCGACTACC AATGCATCGC   31260
TGGTGAACGC GACTGGCGAA TACAAGGACT CGTTGCCACC GGTAGCGCAG CGCGTCCGTC   31320
CGGCCGAATC GCATACACGT TCGGACTTCA AGGGCCCGCC ATCAGCGTGG AGACGGCGTG   31380
CAGCTTCCTC GTCGCGGTTC ACCTCGCCTG CCAGGCCCCC CCCACGGCG AATACTCCCT   31440
GGCGCTCGCT GGCGGCGTGA CCATCATGGC CACGCCAGCC ATATTCATCG CGTTCGACTC   31500
CGAGAGCGCG GGTGCCCCCG ACGGTCGCTG CAAGGCCTTC TCGCCGGAAG CCGACGGTTC   31560
GGGCTGGGCC GAAGGCGCCG GGATGCTCCT GCTCGAGCGC CTCTCCGATG CCGTCCAAAA   31620
CGGTCATCCC GTCCTCGCCG TCCTTCGAGG CTCCGCCGTC AACCAGGACG GCCGGAGCCA   31680
AGGCCTCACC GCGCCCAATG GCCCTGCCCA GGAGCGCGTC ATCCGGCAAG CGCTCGACAG   31740
```

```
CGCGCGGCTC ACTCCAAAGG ACGTCGACGT CGTCGAGGCT CACGGCACGG GAACCACCCT    31800
CGGAGACCCC ATCGAGGCAC AGGCCGTTTT TGCCACCTAT GGCGAGGCCC ATTCCAAGA    31860
CAGACCCCTC TGGCTTGGAA GCCTCAAGTC CAACCTGGGA CATACTCAGG CCGCGGCCGG    31920
CGTCGGCGGC ATCATCAAGA TGGTGCTCGC GTTGCAGCAC GGTCTCTTGC CCAAGACCCT    31980
CCATGCCCAG AATCCCTCCC CCCACATCGA CTGGTCTCCA GGCATCGTAA AGCTCCTGAA    32040
CGAGGCCGTC GCCTGGACGA CCAGCGGACA TCCTCGCCGC GCCGGTGTTT CCTCGTTCGG    32100
CGTCTCCGGC ACCAACGCCC ATGTCATCCT CGAAGAGGCT CCCGCCGCCA CGCGGGCCGA    32160
GTCAGGCGCT TCACAGCCTG CATCGCAGCC GCTCCCCGCG GCGTGGCCCG TCGTCCTGTC    32220
GGCCAGGAGC GAGGCCGCCG TCCGCGCCCA GGCTCAAAGG CTCCGCGAGC ACCTGCTCGC    32280
CCAAGGCGAC CTCACCCTCG CCGATGTGGC CTATTCGCTG GCCACCACCC GCGCCCACTT    32340
CGAGCACCGC GCCGCTCTCG TAGCCCACGA CCGCGACGAG CTCCTCTCCG CGCTCGACTC    32400
GCTCGCCCAG GACAAGCCCG CACCGAGCAC CGTCCTCGGA CGGAGCGGAA GCCACGGCAA    32460
GGTCGTCTTC GTCTTTCCTG GGCAAGGCTC GCAGTGGGAA GGGATGGCCC TCTCCCTGCT    32520
CGACTCCTCG CCCGTCTTCC GCACACAGCT CGAAGCATGC GAGCGCGCGC TCCGTCCTCA    32580
CGTCGAGTGG AGCCTGCTCG CCGTCCTGCG CCGCGACGAG GGCGCCCCCT CCCTCGACCG    32640
CGTCGACGTC GTGCAGCCCG CCCTCTTTGC CGTCATGGTC TCCCTGGCCG CCCTCTGGCG    32700
CTCGCTCGGC GTCGAGCCCG CCGCCGTCGT CGGCCACAGC CAGGGCGAGA TAGCCGCCGC    32760
CTTCGTCGCA GGCGCTCTCT CCCTCGAGGA CGCGGCCCGC ATCGCCGCCC TGCGCAGCAA    32820
AGCGTCACCA CCGTCGCCGG CAACGGGCAT GGCCGCCGTC GAGCTCGGCG CCTCCGACCT    32880
CCAGACCTAC CTCGCTCCCT GGGGCGACAG GCTCTCCATC GCCGCCGTCA ACAGCCCCAG    32940
GGCCACGCTC GTATCCGGCG AGCCCGCCGC CGTCGACGCG CTGATCGACT CGCTCACCGC    33000
AGCGCAGGTC TTCGCCCGAA GAGTCCGCGT CGACTACGCC TCCCACTCAG CCCAGATGGA    33060
CGCCGTCCAA GACGAGCTCG CCGCAGGTCT AGCCAACATC GCTCCTCGGA CGTGCGAGCT    33120
CCCTCTTTAT TCGACCGTCA CCGGCACCAG GCTCGACGGC TCCGAGCTCG ACGGCGCGTA    33180
CTGGTATCGA AACCTCCGGC AAACCGTCCT GTTCTCGAGC GCGACCGAGC GGCTCCTCGA    33240
CGATGGGCAT CGCTTCTTCG TCGAGGTCAG CCCTCATCCC GTGCTCACGC TCGCCCTCCG    33300
CGAGACCTGC GAGCGCTCAC CGCTCGATCC CGTCGTCGTC GGCTCCATTC GACGCGACGA    33360
AGGCCACCTC CCCCGTCTCC TTGCTCTCTT GGGCCGAGCT CTATGGCCGG GCCTCACGCC    33420
CGAGTGGAAG GCCTTCTTCG CGCCCTTCGC TCCCCGCAAG GTCTCACTCC CCACCTACGC    33480
CTTCCAGCGC GAGCGTTTCT GGCTCGACGC CCCCAACGCA CACCCCGAAG GCGTCGCTCC    33540
CGCTGCGCCG ATCGATGGGC GGTTTTGGCA AGCCATCGAA CGCGGGGACC TCGACGCGCT    33600
CAGCGGCCAG CTCCACGCGG ACGGCGACGA GCAGCGCGCC GCCCTCGCCC TGCTCCTTCC    33660
CACCCTCTCG AGCTTTCACC ACCAGCGCCA AGAGCAGAGC ACGGTCGACA CCTGGCGCTA    33720
CCGCATCACG TGGAGGCCTC TGACCACCGC CGCCACGCCC GCCGACCTCG CCGGCACCTG    33780
GCTCCTCGTC GTGCCGTCCG CGCTCGGCGA CGACGCGCTC CCTGCCACGC TCACCGATGC    33840
GCTTACCCGG CGCGGCGCGC GTGTCCTCGC GCTGCGCCTG AGCCAGGTTC ACATAGGCCG    33900
CGCGGCTCTC ACCGAGCACC TGCGCGAGGC TGTTGCCGAG ACTGCCCCGA TTCGCGGCGT    33960
GCTCTCCCTC CTCGCCCTCG ACGAGCGCCC CCTCGCGGAC CATGCCGCCC TGCCCGCGGG    34020
CCTTGCCCTC TCGCTCGCCC TCGTCCAAGC CCTCGGCGAC CTCGCCCTCG AGGCTCCCTT    34080
GTGGCTCTTC ACGCGCGGCG CCGTCTCGAT TGGACACTCC GACCCACTCG CCCATCCCAC    34140
```

-continued

```
CCAGGCCATG ATCTGGGGCT TGGGCCGCGT CGTCGGCCTC GAGCACCCCG AGCGGTGGGG    34200
CGGGCTCGTC GACCTCGGCG CAGCGCTCGA CGCGAGCGCC GCAGGCCGCT TGCTCCCGGC    34260
CCTCGCCCAG CGCCACGACG AAGACCAGCT CGCGCTGCGC CCGGCCGGCC TCTACGCACG    34320
CCGCTTCGTC CGCGCCCCGC TCGGCGATGC GCCTGCCGCT CGCGGCTTCA TGCCCCGAGG    34380
CACCATCCTC ATCACCGGTG GTACCGGCGC CATTGGCGCT CACGTCGCCC GATGGCTCGC    34440
TCGAAAAGGC GCTGAGCACC TCGTCCTCAT CAGCCGACGA GGGGCCCAGG CCGAAGGCGC    34500
CGTGGAGCTC CACGCCGAGC TCACCGCCCT CGGCGCGCGC GTCACCTTCG CCGCGTGCGA    34560
TGTCGCCGAC AGGAGCGCTG TCGCCACGCT TCTCGAGCAG CTCGACGCCG GAGGGCCACA    34620
GGTGAGCGCC GTGTTCCACG CGGGCGGCAT CGAGCCCCAC GCTCCGCTCG CCGCCACCTC    34680
CATGGAGGAT CTCGCCGAGG TTGTCTCCGG CAAGGTACAA GGTGCAAGAC ACCTCCACGA    34740
CCTGCTCGGC TCTCGACCCC TCGACGCCTT TGTTCTCTTC TCGTCCGGCG CGGTCGTCTG    34800
GGGCGGCGGA CAACAAGGCG GCTATGCCGC TGCGAACGCC TTCCTCGATG CCCTGGCCGA    34860
GCAGCGGCGC AGCCTTGGGC TGACGGCGAC ATCGGTGGCC TGGGGCGTGT GGGGCGGCGG    34920
CGGCATGGCT ACCGGGCTCC TGGCAGCCCA GCTAGAGCAA CGCGGTCTGT CGCCGATGGC    34980
CCCCTCGCTG GCCGTGGCGA CGCTCGCGCT GGCGCTGGAG CACGACGAGA CCACCCTCAC    35040
CGTCGCCGAC ATCGACTGGG CGCGCTTTGC GCCTTCGTTC AGCGCCGCTC GCTCCCGCCC    35100
GCTCCTGCGC GATTTGCCCG AGGCGCAGCG CGCTCTCGAA GCCAGCGCCG ATGCGTCCTC    35160
CGAGCAAGAC GGGGCCACAG GCCTCCTCGA CAAGCTCCGA AACCGCTCGG AGAGCGAGCA    35220
GATCCACCTG CTCTCCTCGC TGGTGCGCCA CGAAGCGGCC CTCGTCCTGG GCCATACCGA    35280
CGCCTCCCAG GTCGACCCCC ACAAGGGCTT CATGGACCTC GGCCTCGATT CGCTCATGAC    35340
CGTCGAGCTT CGTCGGCGCT TGCAGCAGGC CACCGGCATC AAGCTCCCGG CCACCCTCGC    35400
CTTCGACCAT CCCTCTCCTC ATCGCGTCGC GCTCTTCTTG CGCGACTCGC TCGCCCACGC    35460
CCTCGGCGCG AGGCTCTCCG TCGAGCGCGA CGCCGCCGCG CTCCCGGCGC TTCGCTCGGC    35520
GAGCGACGAG CCCATCGCCA TCGTCGGCAT GGCCCTCCGC TTGCCGGGCG GCATCGGCGA    35580
TGTCGACGCT CTTTGGGAGT TCCTCGCCCA AGGACGCGAC GCCGTCGAGC CCATTCCCCA    35640
TGCCCGATGG GATGCCGGTG CCCTCTACGA CCCCGACCCC GACGCCAAGG CCAAGAGCTA    35700
CGTCCGGCAT GCCGCCATGC TCGACCAGGT CGACCTCTTC GATCCTGCCT TCTTTGGCAT    35760
CAGCCCTCGC GAGGCCAAAT ACCTCGACCC CCAGCACCGC CTGCTCCTCG AATCTGCCTG    35820
GCTGGCCCTC GAGGACGCCG GCATCGTCCC CTCCACCCTC AAGGATTCTC CACCGGCGT    35880
CTTCGTCGGC ATCGGCGCCA GCGAATACGC ACTGCGAAAC ACGAGCTCCG AAGAGGTCGA    35940
AGCGTATGCC CTCCAAGGCA CCGCCGGGTC CTTTGCCGCG GGGCGCTTGG CCTACACGCT    36000
CGGCCTGCAA GGGCCCGCGC TCTCGGTCGA CACCGCCTGC TCCTCCTCGC TCGTCGCCCT    36060
CCACCTCGCC TGCCAAGCCC TCCGACAGGG CGAGTGCAAC CTCGCCCTCG CCGCGGGCGT    36120
CTCCGTCATG GCCTCCCCCG GGCTCTTCGT CGTCCTTTCC CGCATGCGTG CTTTGGCGCC    36180
CGATGGCCGC TCCAAGACCT TCTCGACCAA CGCCGACGGC TACGGACGCG GAGAGGGCGT    36240
CGTCGTCCTT GCCCTCGAGC GGCTCGGCGA CGCCCTCGCC CGAGGACACC GCGTCCTCGC    36300
CCTCGTCCGC GGCACCGCCA TGAACCATGA CGGCGCGTCG AGCGGCATCA CCGCCCCCAA    36360
TGGCACCTCC CACCAGAAGG TCCTCCGCGC CGCGCTCCAC GACGCCCATA TCGGCCCTGC    36420
CGACGTCGAC GTCGTCGAAT GCCATGGCAC CGGCACCTCC TTGGGAGACC CCATCGAGGT    36480
GCAAGCCCTG GCCGCCGTCT ACGCCGATGG CAGACCCGCT GAAAAGCCTC TCCTTCTCGG    36540
```

```
CGCACTCAAG ACCAACATTG GCCATCTCGA GGCCGCCTCC GGCCTCGCGG GCGTCGCCAA    36600
GATCGTCGCC TCCCTCCGCC ATGACGCCCT GCCCCCCACC CTCCACACGA CCCCGCGCAA    36660
TCCCCTGATC GAGTGGGATG CGCTCGCCAT CGACGTCGTC GATGCCACGA GGGCGTGGGC    36720
CCGCCACGAA GATGGCAGTC CCCGCCGCGC CGGCGTCTCC GCCTTCGGAC TCTCCGGCAC    36780
CAACGCCCAC GTTATCCTCG AAGAGGCTCC CGCGATCCCG CAGGCCGAGC CCACCGCGGC    36840
ACAGCTCGCG TCGCAGCCGC TTCCCGCAGC CTGGCCCGTG CTCCTGTCGG CCAGGAGCGA    36900
GCCGGCCGTG CGCGCCCAGG CCCAGAGGCT CCGCGACCAC CTCCTCGCCC ACGACGACCT    36960
CGCCCTGGCC GATGTAGCCT ACTCGCTCGC CACCACCCGG GCTACCTTCG AGCACCGTGC    37020
CGCTCTCGTG GTCCACGACC GCGAAGAGCT CCTCTCCGCG CTCGATTCGC TCGCCCAGGG    37080
AAGGCCCGCC CCGAGCACCG TCGTCGAACG AAGCGGAAGC CACGGCAAGG TCGTCTTCGT    37140
CTTTCCTGGG CAAGGCTCGC AGTGGGAAGG GATGGCCCTC TCCCTGCTCG ATACCTCGCC    37200
GGTCTTCCGG GCACAGCTCG AAGCGTGCGA GCGCGCCCTC GCGCCCACG TGGACTGGTC    37260
GCTGCTCGCG GTGCTCCGCG GCGAGGAGGG CGCGCCCCG CTCGACCGGG TCGACGTGGT    37320
CCAGCCCGCG CTGTTCTCGA TGATGGTCTC GCTGGCCGCC CTGTGGCGCT CCATGGGCGT    37380
CGAGCCCGAC GCGGTGGTCG GCCATAGCCA GGGCGAGATC GCCGCGGCCT GTGTGGCGGG    37440
CGCGCTGTCG CTCGAGGACG CTGCCAAGCT GGTGGCGCTG CGCAGCCGTG CGCTCGTGGA    37500
GCTCGCCGGC CAGGGGGCCA TGGCCGCGGT GGAGCTGCCG GAGGCCGAGG TCGCACGGCG    37560
CCTCCAGCGC TATGGCGATC GGCTCTCCAT CGGGGCGATC AACAGCCCTC GTTCACGAC    37620
GATCTCCGGC GAGCCCCCTG CCGTCGCCGC CCTGCTCCGC GATCTGGAGT CCGAGGGCGT    37680
CTTCGCCCTC AAGCTGAGTT ACGACTTCGC CTCCCACTCC GCGCAGGTCG AGTCGATTCG    37740
CGACGAGCTC CTCGATCTCC TGTCGTGGCT CGAGCCGCGC TCGACGGCGG TCCCGTTCTA    37800
CTCCACGGTG AGCGGCGCCG CGATCGACGG GAGCGAGCTC GACGCCGCCT ACTGGTACCG    37860
GAACCTCCGG CAGCCGGTCC GCTTCGCAGA CGCTGTGCAA GGCCTCCTTG CCGGAGAACA    37920
TCGCTTCTTC GTGGAGGTGA GCCCCAGTCC TGTGCTGACC TTGGCCTTGC ACGAGCTCCT    37980
CGAAGCGTCG GAGCGCTCGG CGGCGGTGGT CGGCTCTCTG TGGAGCGACG AAGGGGATCT    38040
ACGGCGCTTC CTCGTCTCGC TCTCCGAGCT CTACGTCAAC GGCTTCGCCC TGGATTGGAC    38100
GACGATCCTG CCCCCCGGGA AGCGGGTGCC GCTGCCCACC TACCCCTTCC AGCGCGAGCG    38160
CTTCTGGCTC GACGCCTCCA CGGCACCCGC CGCCGGCGTC AACCACCTTG CTCCGCTCGA    38220
GGGGCGGTTC TGGCAGGCCA TCGAGAGCGG GAATATCGAC GCGCTCAGCG GCCAGCTCCA    38280
CGTGGACGGC GACGAGCAGC GCGCCGCCCT TGCCCTGCTC CTTCCACCC TCGCGAGCTT    38340
TCGCCACGAG CGGCAAGAGC AGGGCACGGT CGACGCCTGG CGCTACCGCA TCACGTGGAA    38400
GCCTCTGACC ACCGCCACCA CGCCCGCCGA CCTGGCCGGC ACCTGGCTCC TCGTCGTGCC    38460
GGCCGCTCTG GACGACGACG CGCTCCCCTC CGCGCTCACC GAGGCGCTCG CCCGGCGCGG    38520
CGCGCGCGTC CTCGCCGTGC GCCTGAGCCA GGCCCACCTG GACCGCGAGG CTCTCGCCGA    38580
GCACCTGCGC CAGGCTTGCG CCGAGACCGC GCCGCCTCGC GGCGTGCTCT CGCTCCTCGC    38640
CCTCGACGAA AGTCCCCTCG CCGACCATGC CGCCGTGCCC GCGGGACTCG CCTTCTCGCT    38700
CACCCTCGTC CAAGCCCTCG GCGACATCGC CCTCGACGCG CCCTTGTGGC TCTTCACCCG    38760
CGGCGCCGTC TCCGTCGGAC ACTCCGACCC CATCGCCCAT CCGACGCAGG CGATGACCTG    38820
GGGCCTGGGC CGCGTCGTCG GCCTCGAGCA CCCCGAGCGC TGGGAGGGC TCGTCGACGT    38880
CGGCGCAGCG ATCGACGCGA GCGCCGTGGG CCGCTTGCTC CCGGTCCTCG CCCTGCGCAA    38940
```

```
CGATGAGGAC CAGCTCGCTC TCCGCCCGGC CGGGTTCTAC GCTCGCCGCC TCGTCCGCGC    39000
TCCGCTCGGC GACGCGCCGC CCGCACGTAC CTTCAAGCCC CGAGGCACCC TCCTCATCAC    39060
CGGAGGCACC GGCGCCGCTG GCGCTCACGT CGCCCGATGG CTCGCTCGAG AAGGCGCAGA    39120
GCACCTCGTC CTCATCAGCC GCCGAGGGGC CCAGGCCGAG GGCGCCTCGG AGCTCCACGC    39180
CGAGCTCACG GCCCTGGGCG CGCGCGTCAC CTTCGCCGCG TGTGATGTCG CCGACAGGAG    39240
CGCTGTCGCC ACGCTTCTCG AGCAGCTCGA CGCCGAAGGG TCGCAGGTCC GCGCCGTGTT    39300
CCACGCGGGC GGCATCGGGC GCCACGCTCC GCTCGCCGCC ACCTCTCTCA TGGAGCTCGC    39360
CGACGTTGTC TCTGCCAAGG TCCTAGGCGC AGGGAACCTC ACGACCTGC TCGGTCCTCG      39420
ACCCCTCGAC GCCTTCGTCC TTTTCTCGTC CATCGCAGGC GTCTGGGGCG GCGGACAACA    39480
AGCCGGATAC GCCGCCGGAA ACGCCTTCCT CGACGCCCTG GCCGACCAGC GGCGCAGTCT    39540
TGGACAGCCG GACACGTCCG TGGTGTGGGG CGCGTGGGGC GGCGGCGGTG GTATATTCAC    39600
GGGGCCCCTG GCAGCCCAGC TGGAGCAACG TCGTCTGTCG CCGATGGCCC CTTCGCTGGC    39660
CGTGGCGGCG CTCGCGCAAG CCCTGGAGCA CGACGAGACC ACCGTCACCG TCGCCGACAT    39720
CGACTGGGCG CGCTTTGCGC CTTCGATCAG CGTCGCTCGC TCCGCCGCT CCTGCGCGAC      39780
TTGCCCGAGC AGCGCGCCCT CGAAGACAGA GAAGGCGCGT CCTCCTCCGA GCACGGCCCG    39840
GCCCCCCGAC CTCCTCGACA AGCTCCGGAG CCGCTCGGAG AGCGAGCAGC TCCGTCTGCT    39900
CGCCGCGCTG GTGTGCGACG AGACGGCCCT CGTCCTCGGC CACGAAGGCC GCTTCCCAGC    39960
TCGACCCCGA CAAGGCTTCT TCGACCTCGG TCTCGATTCG ATCATGACCG TCGAGCTTCG    40020
TCGGCGCTTG CAACAGGCCA CCGGCATCAA GCTCCCGGCC ACCCTCGCCT TCGACCATCC    40080
CTCTCCTCAT CGCGTCGCGC TCTTCATGCG CGACTCGCTC GCCCACGCCC TCGGCACGAG    40140
GCTCTCCGCC GAGGCGACGC CGCCGCGCTC CGGCCGCGCC TCGAGCGACG AGCCCATCGC    40200
CATCGTCGGC ATGGCCCTGC GCCTGCCGGG CGGCGTCGGC GATGTCGACG CTCTTTGGGA    40260
GTTCCTCCAC CAAGGGCGCG ACGCGGTCGA GCCCATTCCA CAGAGCCGCT GGGACGCCGG    40320
TGCCCTCTAC GACCCCGACC CCGACGCCGA CGCCAAGAGC TACGTCCGGC ATGCCGCGAT    40380
GCTCGACCAG ATCGACCTCT TCGACCCTGC CTTCTTCGGC ATCAGCCCCC GGGAGGCCAA    40440
ACACCTCGAC CCCCAGCACC GCCTGCTCCT CGAATCTGCC TGGCTGGCCC TCGAGGACGC    40500
CGGCATCGTC CCCACCTCCC TCAAGGACTC CCTCACCGGC GTCTTCGTCG GCATCTGCGC    40560
CGGCGAATAC GCGATGCAAG AGGCGAGCTC GGAAGGTTCC GAGGTTTACT TCATCCAAGG    40620
CACTTCCGCG TCCTTTGGCG CGGGGGGCTT GGCCTATACG CTCGGGCTCC AGGGGCCGCG    40680
ATCTTCGGTC GACACCGCCT GCTCCTCCTC GCTCGTCTCC CTCCACCTCG CCTGCCAAGC    40740
CCTCCGACAG GGCGAGTGCA ACCTCGCCCT CGCCGCGGGC GTGTCGCTCA TGGTCTCCCC    40800
CCAGACCTTC GTCATCCTTT CCCGTCTGCG CGCCTTGGCG CCCGACGGCC GCTCCAAGAC    40860
CTTCTCGGAC AACGCCGACG GCTACGGACG CGGAGAAGGC GTCGTCGTCC TTGCCCTCGA    40920
GCGGATCGGC GACGCCCTCG CCCGGAGACA CCGCGTCCTC GTCCTCGTCC GCGGCACCGC    40980
CATCAACCAC GACGGCGCGT CGAGCGGTAT CACCGCCCCC AACGGCACCT CCCAGCAGAA    41040
GGTCCTCCGG GCCGCGCTCC ACGACGCCCG CATCACCCCC GCCGACGTCG ACGTCGTCGA    41100
GTGCCATGGC ACCGGCACCT CGCTGGGAGA CCCCATCGAG GTGCAAGCCC TGGCCGCCGT    41160
CTACGCCGAC GGCAGACCCG CTGAAAAGCC TCTCCTTCTC GGCGCGCTCA AGACCAACAT    41220
CGGCCATCTC GAGGCCGCCT CCGGCCTCGC GGGCGTCGCC AAGATGGTCG CCTCGCTCCG    41280
CCACGACGCC CTGCCCCCCA CCCTCCACGC GACCCACGC AATCCCCTCA TCGAGTGGGA      41340
```

```
GGCGCTCGCC ATCGACGTCG TCGATACCCC GAGGCCTTGG CCCCGCCACG AAGATGGCAG    41400
TCCCCGCCGC GCCGGCATCT CCGCCTTCGG ATTCTCGGGC ACCAACGCCC ACGTCATCCT    41460
CGAAGAGGCT CCCGCCGCCC TGCCGGCCGA GCCCGCCACC TCACAGCCGG CGTCGCAAGC    41520
CGCTCCCGCG GCGTGGCCCG TGCTCCTGTC GGCCAGGAGC GAGGCCGCCG TCCGCGCCCA    41580
GGCGAAGCGG CTCCGCGACC ACCTCGTCGC CCACGACGAC CTCACCCTCG CGGATGTGGC    41640
CTATTCGCTG GCCACCACCC GCGCCCACTT CGAGCACCGC GCCGCTCTCG TAGCCCACAA    41700
CCGCGACGAG CTCCTCTCCG CGCTCGACTC GCTCGCCCAG GACAAGCCCG CCCCGAGCAC    41760
CGTCCTCGGA CGGAGCGGAA GCCACGGCAA GCTCGTCTTC GTCTTTCCTG GCAAGGCTC    41820
GCAGTGGGAA GGGATGGCCC TCTCGCTGCT CGACTCCTCG CCCGTCTTCC GCGCTCAGCT    41880
CGAAGCATGC GAGCGCGCGC TCGCTCCTCA CGTCGAGTGG AGCCTGCTCG CCGTCCTGCG    41940
CCGCGACGAG GGCGCCCCCT CCCTCGACCG CGTCGACGTC GTACAGCCCG CCCTCTTTGC    42000
CGTCATGGTC TCCCTGGCGG CCCTCTGGCG CTCGCTCGGC GTAGAGCCCG CCGCCGTCGT    42060
CGGCCACAGT CAGGGCGAGA TCGCCGCCGC CTTCGTCGCA GGCGCTCTCT CCCTCGAGGA    42120
CGCGGCCCGC ATCGCCGCCC TGCGCAGCAA AGCGCTCACC ACCGTCGCCG GCAACGGGGC    42180
CATGGCCGCC GTCGAGCTCG GCGCCTCCGA CCTCCAGACC TACCTCGCTC CTGGGGCGA    42240
CAGGCTCTCC ATCGCCGCCG TCAACAGCCC CAGGGCCACG CTCGTGTCCG GCGAGCCCGC    42300
CGCCATCGAC GCGCTGATCG ACTCGCTCAC CGCAGCGCAG GTCTTCGCCC GAAAAGTCCG    42360
CGTCGACTAC GCCTCCCACT CCGCCCAGAT GGACGCCGTC CAAGACGAGC TCGCCGCAGG    42420
TCTAGCCAAC ATCGCTCCTC GGACGTGCGA GCTCCCTCTT TATTCGACCG TCACCGGCAC    42480
CAGGCTCGAC GGCTCCGAGC TCGACGGCGC GTACTGGTAT CGAAACCTCC GGCAAACCGT    42540
CCTGTTCTCG AGCGCGACCG AGCGGCTCCT CGACGATGGG CATCGCTTCT TCGTCGAGGT    42600
CAGCCCCCAT CCCGTGCTCA CGCTCGCCCT CCGCGAGACC TGCGAGCGCT CACCGCTCGA    42660
TCCCGTCGTC GTCGGCTCCA TTCGACGCGA CGAAGGCCAC CTCGCCCGCC TGCTCCTCTC    42720
CTGGGCGGAG CTCTCTACCC GAGGCCTCGC GCTCGACTGG AACGCCTTCT TCGCGCCCTT    42780
CGCTCCCCGC AAGGTCTCCC TCCCCACCTA CCCCTTCCAA CGCGAGCGCT TCTGGCTCGA    42840
CGCCTCCACG GCGCACGCTG CCGACGTCGC CTCCGCAGGC CTGACCTCGG CCGACCACCC    42900
GCTGCTCGGC GCCGCCGTCG CCCTCGCCGA CCGCGATGGC TTTGTCTTCA CAGGACGGCT    42960
CTCCCTCGCA GAGCACCCGT GGCTCGAAGA CCACGTCGTC TTCGGCATAC CCTGTCCTGC    43020
CAGGCGCCGC CTCCTCGAGC TCGCCCTGCA TGTCGCCCAT CTCGTCGGCC TCGACACCGT    43080
CGAAGACGTC ACGCTCGACC CCCCCCTCGC TCTCCCATCG CAGGGCGCCG TCCTCCTCCA    43140
GATCTCCGTC GGGCCCGCGG ACGGTGCTGG ACGAAGGGCG CTCTCCGTTC ATAGCCGGCG    43200
CCACGACGCG CTTCAGGATG GCCCCTGGAC TCGCCACGCC AGCGGCTCTC TCGCGCAAGC    43260
TAGCCCGTCC CATTGCCTTC GATGCTCCGC GAATGGCCCC CCCTCGGGCG CCACCCAGGT    43320
GGACACCCAA GGTTTCTACG CAGCCCTCGA GAGCGCTGGG CTTGCTTATG GCCCCGAGTT    43380
CCAGGGCCTC CGCCGCCGTC TACAAGCGCG GCGACGAGCT CTTCGCCGAA GCCAAGCTCC    43440
CGGACGCCGC CGAAGAGGAC GCCGCTCGTT TTGCCCTCCA CCCCGCCCTG CTCGACAGCG    43500
CCTTGCAGGC GCTCGCCTTT GTAGACGACC AGGCAAAGGC CTTCAGGATG CCCTTCTCGT    43560
GGAGCGGAGT ATCGCTGCGC TCCGGTCGGA GCCACCACCC TGCGCGTGCG TTTCCACCGT    43620
CCTGAGGGCG AATCCTCGCG CTCGCTCCTC CTCGCCGACG CCAGAGGCGA ACCCATCGCC    43680
TCGGTGCAAG CGCTCGCCAT GCGCGCCGCG TCCGCCGAGC AGCTCCGCAG ACCCGGGAGC    43740
```

| | | | | | |
|---|---|---|---|---|---|
| GTCCCACCTC | GATGCCCTCT | TCCGCATCGA | CTGGAGCGAG | CTGCAAAGCC | CCACCTCACC | 43800
| GCCCATCGCC | CCGAGCGGTG | CCCTCCTCGG | CACAGAAGGT | CTCGACCTCG | GGACCAGGGT | 43860
| GCCTCTCGAC | CGCTATACCG | ACCTTGCTGC | TCTACGCAGC | GCCCTCGACC | AGGGCGCTTC | 43920
| GCCTCCAAGC | CTCGTCATCG | CCCCCTTCAT | CGCTCTGCCC | GAAGGCGACC | TCATCGCGAG | 43980
| CGCCCGCGAG | ACCACCGCGC | ACGCGCTCGC | CCTCTTGCAA | GCCTGGCTCG | CCGACGAGCG | 44040
| CCTCGCCTCC | TCGCGCCTCG | CCCTCGTCAC | CGACGCGCC | GTCGCCACCC | ACGCTGAAGA | 44100
| AGACGTCAAG | GGCCTCGCTC | ACGCGCCTCT | CTGGGTCTC | GCTCGCTCCG | CGCAGAGCGA | 44160
| GCACCCAGAG | CGCCCTCTCG | TCCTCGTCGA | CCTCGACGAC | AGCGAGGCCT | CCCAGCACGC | 44220
| CCTGCTCGGC | GCGCTCGACG | CAAGAGAGCC | AGAGATCGCC | CTCCGCAACG | GCAAACCCCT | 44280
| CGTTCCAAGG | CTCTCACGCC | TGCCCCAGGC | GCCCACGGAC | ACAGCGTCCC | CCGCAGGCCT | 44340
| CGGAGGCACC | GTCCTCATCA | CGGGAGGCAC | CGGCACGCTC | GGCGCCCTGG | TCGCGCGCCG | 44400
| CCTCGTCGTA | AACCACGACG | CCAAGCACCT | GCTCCTCACC | TCGCGCCAGG | GCGCGAGCGC | 44460
| TCCGGGTGCT | GATGTCTTGC | GAAGCGAGCT | CGAAGCTCTG | GGGGCTTCGG | TCACCCTCGC | 44520
| CGCGTGCGAC | GTGGCCGATC | CACGCGCTCT | AAAGGACCTT | CTGGATAACA | TTCCGAGCGC | 44580
| TCACCCGGTC | GCCGCCGTCG | TGCATGCCGC | CAGCGTCCTC | GACGGCGATC | TGCTCGGCGC | 44640
| CATGAGCCTC | GAGCGGATCG | ACCGCGTCTT | CGCCCCAAG | ATCGATGCCG | CCTGGCACTT | 44700
| GCATCAGCTC | ACCCAAGATA | AGCCCCTTGC | CGCCTTCATC | CTCTTCTCGT | CCGTCGCCGG | 44760
| CGTCCTCGGC | AGCTCAGGTC | ACTCCAACTA | CGCCGCTGCG | AGCGCCTTCC | TCGATGCGCT | 44820
| TGCGCACCAC | CGGCGCGCGC | AAGGGCTCCC | TGCCTCATCG | CTCGCGTGGA | GCCACTGGGC | 44880
| CGAGCGCAGC | GCAATGACAG | AGCACGTCAG | CGCCGCCGGC | GCCCCTCGCA | TGGAGCGCGC | 44940
| CGGCCTTCCC | TCGACCTCTG | AGGAGAGGCT | CGCCCTCTTC | GATGCGGCGC | TCTTCCGAAC | 45000
| CGAGACCGCC | CTGGTCCCCG | CGCGCTTCGA | CTTGAGCGCG | CTCAGGGCGA | ACGCCGGCAG | 45060
| CGTCCCCCCG | TTGTTCCAAC | GTCTCGTCCG | CGCTCGCACC | GTACGCAAGG | CCGCCAGCAA | 45120
| CACCGCCCAG | GCCTCGTCGC | TTACAGAGCG | CCTCTCAGCC | CTCCCGCCCG | CCGAACGCGA | 45180
| GCGTGCCCTG | CTCGATCTCA | TCCGCACCGA | AGCCGCCGCC | GTCCTCGGCC | TCGCCTCCTT | 45240
| CGAATCGCTC | GATCCCGATC | GCCTCCTCCA | AGAGCTTGGC | CTCGACTCCA | TCATCGCGCT | 45300
| CGATCTCCGA | AATCGGCTCG | CCGCCGCCAC | CGGCGTGCGA | CTCCCAGCCA | CCCTCCTCTT | 45360
| CGAGCATCCA | ACCCCAGCTG | CGCTCGCAGC | CTTGCTCTTG | GCTCGACTCG | AACCTGGAAT | 45420
| GCGAAGAGGA | CCGGCGAAGG | ACGGCGCCTC | TCCACGGAC | ACAGAGAGCG | ACGGCGCGCT | 45480
| CCTTGGAATG | GTTCAACCAG | CGAACGAGAT | CGGAGCGATC | GAAGAGGCCC | GAAATCTCAT | 45540
| CGCCGCGGCC | TTGAAAGTCC | GCCTGGCGGT | CGAAGACGCG | TCGAAGCGGT | CAGCGGTCGC | 45600
| GATCGCGGAG | GAGCCGCCCA | CTCGACTCGC | AAGGGGTCAA | GCGACACCCC | AGTTGATTTG | 45660
| CTTTCCGGCG | TTCGTGGTTC | CATCGGCGCC | TATTCAGTAC | GCGCGCTTCG | CTTCACACCT | 45720
| CAGGGACCGG | CGCGACATCT | GGTTCATACC | TCATCCAGGC | TACCGCCATA | AGACGCCGCT | 45780
| CACACGGAGC | CTCGACGAGC | TCGTTTCCTC | GCACGCAAGA | ACGACATTGG | CGTGCGCGCG | 45840
| CAATTCCCCC | TTCGTGCTGT | TCGGCCACTC | TTCGGGTGGA | AACATCGCCC | ACATGGTGGC | 45900
| CGAGCACCTG | GAGAGCATCG | GACACGGCCC | CGCCGGAGTC | GTGCTCCTGG | ACAGCTATGA | 45960
| TTACGCCAGT | CCAGCGGTAG | AGGCTGGGCT | GAAGATCTTC | CATGTAGAGC | AGCTGCAAAC | 46020
| TTGGGGCGCC | TCGGACGCCG | GCCTGACCGC | CGAGGCGTGG | TACTATGAAC | ACATCGGACT | 46080
| CGAGACCTGG | AAGCCTAGAC | AGCTGGCCGC | TCCGACATTG | CATGTCCGCG | CGACCGAACC | 46140

```
CATGAAGCAG TTCGTGGGGA GCGAAGGCGC TCCTGCGGAA TGGCGCGCGA GCTGGAAATT    46200
GCCGCATGTC GCGATAGATG CTCCAGGAGA CCACGCTACG GTGGTAGATC ACCCTTTCTT    46260
GGCGCAAGCG GTCGACGACT GGCTGTCCTC GCTCTCCAAC GAGCCGTCCA ACCAATAGGC    46320
GTTTTTTTCC GGACGCCGCT GCCGCTCTTG TCCGCCTCCG AACAAACTTC TATTGGAGGA    46380
TGAAACAACC ATGGACCCGA AACGAATCCA ATCCGTCATT GAACGCATCG AAATCATCGA    46440
CACGCTCACC ACCTTCACCC GCGCAGCAGA CATGCGTGAA TGGGATACGT GTCGGGCCAT    46500
CCTCGGAGAG ACGATCATCA ACGATCACGG CACGCCCGAG ACTCTCTCTC GCGACGCGCT    46560
CATCGAGCGG TGGCGTGTAC AGTCGCCCAC GCTCGACCTG ATCCATCACG TGACCACGGA    46620
TCATCTCGTC GTGATCGATG GCGACCTCGC GAAGGTCCAC ACCCAGTTCA TTATCACGGT    46680
GCGCGCGACG GGCGCGCCGA GCGGCGATCT GTGCACGCGC GGCGGCTCCT GCGATTACGA    46740
TCTGAAGCGG ACCGATGAAG GCTGGAAGCT CACGGGCTTC AAGTCGGTCA TCCAGTGGAG    46800
CATGGGGAGC GTGAACATCT AGCTTCCGGT CGGGGCATG AAGGACCGCC ATGCAAATTT    46860
CGCCAGGGGC TCGGACATCT CCCATCACGG CGGATAGCAA ACGAGGAAGC AATATGGCAT    46920
CGCAGCAGAT CGAGCTGATC AAAATGTTCA AACGGATGGT GGACGCCATG GCCAGCATCC    46980
AGTCCGCTGT CGACCAGGAC GCGCTCGCCG CTCAAGGTGG CACGCTCAAG CGCCTCATCG    47040
AGGACGGCTA CAACCTCGAG GCCGCTCAAG GTGCCGATCG CTTTCACAAC TGGGGGATGT    47100
TCACGAGGA GGTTTATCGT GATGTTCTTC AACAGCTGCC AGATTACGAC AAGAGCGACA    47160
CAGACGGTTA TTCGGAGCAG CTCTACGTCT ACACGCTGAA GCAAGTTCCG GCCGACGAAG    47220
ATCGGCCACG CAAGATCCTG GAGGTCGGCT GCAACACTGG GAAGGGCCTC AACTTCCTTT    47280
CCCGGATCGA GGGTCGCAGC ACCTTCGTCG GGCTCGACCT GTCGCAGCAA GCGGTGGACA    47340
TCGCCAACGC CCGGTTCTCG CGACCGGGCT CGTTGACCTA CGTTCAAGGC GACGCGGAGA    47400
ACCTTCCTTT CGCCGACGGC GAATTCGACG TCGTCATCAA TGTCGAGAGC TCGCACAACT    47460
ACCCTAATCT GCGCAAATCA TTCCTCGAAG TGGCGCGCGT GCTGCGACCG GCGGGTTCT    47520
TTTCGCATGT GGATGTCTTC TCGGACAATC GCTATTCGGT GATGCAGAAT TGCAAGCAGC    47580
AGACCAGCGG CGAGCTCGAC TGGCTCAAGG AGACCGACAT CTCGGAGTAC GTAAAAGAGG    47640
CTATCCGGCG ACGACTGGCG CCCGGCAGCA AGGCAAGGCA ACAGGTGGAG CGCGCGCTGC    47700
CGTACCCGCT CGGAAGGCTT TTCAGCTCGG TCATGATGCG CGGCTACGGA TCCGAGTTTG    47760
CCGTCGGACA GAAGTCGGAC GACTGGATCA GGAATGTCTC ATGGCTCAAC CCTCCCGGCC    47820
AGCAATGGTT GTCGCAGATC ACCTCGTATC GCCACACGCT CGCTACGAAG GCGCGCGGCC    47880
ACGGGTCTTG AGCGGCGGGC GAGCTGGCGG GCGCCGTGGC TCCGTCGCTT GATGCCCCCC    47940
TGGGCGTGTG TTGACGCTCA GCGGACGTGG ATGTCCGGCT TCGGGACCGG CGCCATCCCC    48000
TCCCCGATGT GGAAGCTCGG GTGAGGCGGC TGGTTGTAGG CGCCGTTCTG CCACGAGATG    48060
GCCACGCGGT ACTGCGGATC GTGCATCAGG GTGTGGATCC GGCTCGTGGC GACGCGGTTC    48120
GTGGTGAAGA TACGAATCGA GCTGCCGCAG CGGAAGATCA CCTCTTCGCG CCAGTCGCCG    48180
AGGATATCGG CGCTGAGGGT CGGGTTGCTC TTCGAGCCGT TGTTCGCGGT GCAGCCCTCG    48240
GCCGCGAAGT TGCTTCCCTC GCCGTCGGCC TGGCGGATGC TGTTGCCGTC GAGCAGCTCC    48300
CGGCTCAGAT CCGCGTCCCA CCAGATGAGG AAGTTGGACG ACGCGGGGCG GTTCCCGATG    48360
GCGTCGCCGT CCGCGCCGCT CAGGAGCTGG CTGCTATTGA CCCACGCCTC GCTGCCCGGG    48420
TTGCGCGGAT CGACGTCGGC CGCCACGCCG CGGCCGGGGC CCTCCTCGCC GCCGTTGCCC    48480
GGCCCCCGCC AGAGGACCTC GCACGTGCGC GCGTCGCGCA TGGCATAGGC GGGTGAGTCC    48540
```

| | | | | | |
|---|---|---|---|---|---|
| CCGCCCTCGT | ACGGCTGGAA | CACCTCGAGG | CCGGGGCGCG | ACAGGATGTG | ATCCGTGACG | 48600
| TGCAGCGCGT | CGCCGTGACC | GTAGTAGTCC | ACGGCGCACA | GGCCCTTGCC | GTCGTTGTCG | 48660
| AACGTGGCGC | CCCCGTTGAT | GATCTCCTGC | TGCGGATCGT | CATCCACGTT | GGCGACGCTG | 48720
| ATGGAGTGGG | TGCCCATGCC | GGCGTACGCC | CCGTTGTCGC | GGCTCGAGCT | GGAGTCGAAC | 48780
| GTCCAGAGGT | TCGTGAGCGC | GCCGTCGCGG | TAGTTCCACG | CCGACAGCGT | GGTGCGCGCG | 48840
| TAGTAGCCGC | GGCCGAACAC | CACGCTCGGA | CGACCGGTGT | CGTCGAGGAA | CGCGACCGTG | 48900
| CCGACGAAGC | GGTCGACGCG | ATTGCCGTAA | CACTCGTTGT | TGCCCCAGCT | GCACGGGTCG | 48960
| CCGCGCCCCA | CCACGAAGTC | GGTCGTCGCG | AGCTCGGCGC | CGGTCTCCCC | GGAGAACACG | 49020
| GTGAGGTACT | CCGGGCCGGT | CAGGATGTAG | CCGTCGTTGT | TGCGGTAGTC | CCGGCTGTCG | 49080
| TCGTCGTTCG | CCGCGGGCCC | CTTGCTGAGG | GGCTCGCCCG | TGCCGTCGCG | TGTCCCGGC | 49140
| GCCGTCTTGA | CGGCCACCTC | CGCCTTCCCG | TCGCCGTCGA | GATCGTAGAC | GAGGAACGGC | 49200
| GAGTAGTGCG | CTCCGGCCCG | GATGTTCACG | CCGAGGTCGA | TGCGCCAGAG | CCGCTCGCCC | 49260
| TCGAGCGAGT | AGGCGTCGAG | GTACGTCTTG | CCGGTGCGGC | CAGCCTGCGA | GTTGTCCTTG | 49320
| AGGTTCGACG | GGTCCCACTT | GACGATGATC | TCGTACCGCC | CGTCGCCGTC | CAGATCT | 49377

( 2 ) INFORMATION FOR SEQ ID NO:2:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="plant consensus translation
            initiator (Clontech)"

( x i ) SEQUENCE DESCRIPTION: SEQ ID NO:2:

GTCGACCATG GTC                                                13

( 2 ) INFORMATION FOR SEQ ID NO:3:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="plant consensus translation
            initiator (Joshi)"

( x i ) SEQUENCE DESCRIPTION: SEQ ID NO:3:

TAAACAATGG CT                                                12

( 2 ) INFORMATION FOR SEQ ID NO:4:

( i ) SEQUENCE CHARACTERISTICS:
        ( A ) LENGTH: 28958 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Sorangium cellulosum ( v i i ) IMMEDIATE SOURCE:
        ( B ) CLONE: p98/1

( x i ) SEQUENCE DESCRIPTION: SEQ ID NO:4:

-continued

```
CGATCGCGTC GGCCTCGACA CCGTCGAAGA GGTCACGCTC GAAGCTCCCC TCGCTCTCCC    60
CTCTCAAGGC ACCATTCTCA TCCAGATCTC CGTCGGACCC ATGGACGAGG CGGGACGAAG   120
GTCGCTCTCC CTCCATGGCC GGACCGAGGA CGCTCCTCAG GACGCCCTT GGACGCGCCA    180
CGCGAGCGGG TCGCTCGCTA AAGCTGCCCC CTCCCTCTCC TTCGATCTTC ACGAATGGGC   240
TCCTCCGGGG GGCACGCCGG TGGACACCCA AGGCTCTTAC GCAGGCCTCG AAAGCGGGGG   300
GCTCGCCTAT GGGCCTCAGT TCCAGGGACT TCGCTCCGTC TGGAAGCGCG GCGACGAGCT   360
CTTCGCCGAG GCCAAGCTCC CGGACGCAGG CGCCAAGGAT GCCGCTCGGT TCGCCCTCCA   420
CCCCGCCCTG TTCGACAGCG CCCTGCACGC GCTTGTCCTT GAAGACGAGC GGACGCCGGG   480
CGTCGCTCTG CCCTTCTCGT GGAGAGGAGT CTCGCTGCGC TCCGTCGGCG CCACCACCCT   540
GCGCGTGCGC TTCCATCGTC CGAATGGCAA GTCCTCCGTG TCGCTCCTCC TCGGCGACGC   600
CGCAGGCGAG CCCCTCGCCT CGGTCCAAGC GCTCGCCACG CGCATCACGT CCCAGGAGCA   660
GCTCCGCACC CAGGGAGCTT CCCTCCACGA TGCTCTCTTC CGGGTTGTCT GGAGAGATCT   720
GCCCAGCCCT ACGTCGCTCT CTGAGGCCCC GAAGGGTGTC CTCCTAGAGA CAGGGGGTCT   780
CGACCTCGCG CTGCAGGCGT CTCTCGCCCG CTACGACGGT CTCGCTGCCC TCCGGAGCGC   840
GCTCGACCAA GGCGCTTCGC CTCCGGGCCT CGTCGTCGTC CCCTTCATCG ATTCGCCCTC   900
TGGCGACCTC ATAGAGAGCG CTCACAACTC CACCGCGCGC GCCCTCGCCT TGCTGCAAGC   960
GTGGCTTGAC GACGAACGCC TCGCCTCCTC GCGCCTCGTC CTGCTCACCC GACAGGCCAT  1020
CGCAACCCAC CCCGACGAGG ACGTCCTCGA CCTCCCTCAC GCTCCTCTCT GGGGCCTTGT  1080
GCGCACCGCG CAAAGCGAAC ACCCGGAGCT CCCTCTCTTC CTCGTCGACC TGGACCTCGG  1140
TCAGGCCTCG GAGCGCGCCC TGCTCGGCGC GCTCGACACA GGAGAGCGTC AGCTCGCTCT  1200
CCGCCATGGA AAATGCCTCG TCCCGAGGTT GGTGAATGCA CGCTCGACAG AGGCGCTCAT  1260
CGCGCCGAAC GTATCCACGT GGAGCCTTCA TATCCCGACC AAAGGCACCT TCGACTCGCT  1320
CGCCCTCGTC GACGCTCCTC TAGCCCGTGC GCCCCTCGCA CAAGGCCAAG TCCGCGTCGC  1380
CGTGCACGCG GCAGGTCTCA ACTTCCGCGA TGTCCTCAAC ACCCTTGGCA TGCTTCCGGA  1440
CAACGCGGGG CCGCTCGGCG GCGAAGGCGC GGGCATTGTC ACCGAAGTCG GCCCAGGTGT  1500
TTCCCGATAC ACTGTAGGCG ACCGGGTGAT GGGCATCTTC CGCGGAGGCT TTGGCCCCAC  1560
GGTCGTCGCC GACGCCCGCA TGATCTGCCC CATCCCCGAT GCCTGGTCCT TCGTCCAAGC  1620
CGCCAGCGTC CCCGTCGTCT TTCTCACCGC CTACTATGGA CTCGTCGATG TCGGGCATCT  1680
CAAGCCCAAT CAACGTGTCC TCATCCATGC GGCCGCAGGC GGCGTCGGTA CTGCCGCCGT  1740
CCAGCTCGCG CGCCACCTCG GCGCCGAAGT CTTCGCCACC GCCAGTCCAG GGAAGTGGGA  1800
CGCTCTGCGC GCGCTCGGCT TCGACGATGC GCACCTCGCG TCCTCACGTG ACCTGGAATT  1860
CGAGCAGCAT TTCCTGCGCT CCACACGAGG GCGCGGCATG GATGTCGTCC TCAACGCCTT  1920
GGCGCGCGAG TTCGTCGACG CTTCGCTGCG TCTCCTGCCG AGCGGTGGAA GCTTTGTCGA  1980
GATGGGCAAG ACGGATATCC GCGAGCCCGA CGCCGTAGGC CTCGCCTACC CCGGCGTCGT  2040
TTACCGCGCC TTCGATCTCT TGGAGGCTGG ACCGGATCGA ATTCAAGAGA TGCTCGCAGA  2100
GCTGCTCGAC CTGTTCGAGC GCGGCGTGCT TCGTCCGCCG CCCATCACGT CCTGGGACAT  2160
CCGGCATGCC CCCCAGGCGT TCCGCGCGCT CGCTCAGGCG CGGCATATTG GAAAGTTCGT  2220
CCTCACCGTT CCCGTCCCAT CGATCCCCGA AGGCACCATC CTCGTCACGG GAGGCACCGG  2280
CACGCTCGGC GCGCTCATCG CGCGCCACCT CGTCGCCAAT CGCGGCGACA AGCACCTGCT  2340
CCTCACCTCG CGAAAGGGTG CGAGCGCTCC GGGGGCCGAG GCATTGCGGA GCGAGCTCGA  2400
```

```
AGCTCTGGGG GCTGCGGTCA CGCTCGCCCG GTGCGACGCG GCCGATCCAC GCGCGCTCCA    2460
AGCCCTCTTG GACAGCATCC CGAGCGCTCA CCCGCTCACG GCCGTCGTGC ACGCCGCCGG    2520
CGCCCTTGAC GATGGGCTGA TCAGCGACAT GAGCCCCGAG CGCATCGACC GCGTCTTTGC    2580
TCCCAAGCTC GACGCCGCTT GGCACTTGCA TCAGCTCACC CAGGACAAGG CCGCTCGGGG    2640
CTTCGTCCTC TTCTCGTCCG CCTCCGGCGT CCTCGGCGGT ATGGGTCAAT CCAACTACGC    2700
GGGGGGCAAT GCGTTCCTTG ACGCGCTCGC GCATCACCGA CGCGTCCATG GGCTCCCAGG    2760
CTCCTCGCTC GCATGGGGCC ATTGGGCCGA GCGCAGCGGA ATGACCCGAC AACCTCAGCG    2820
GCGTCGATAC CGCTCGCATG AGGCGCGCGG TCTCCGATCC ATCGCCTCGG ACGAGGGTCT    2880
CGCCCTCTTC GATATGGCGC TCGGGCGCCC GGAGCCCGCG CTGGTCCCCG CCCGCTTCGA    2940
CATGAACGCG CTCGGCGCGA AGGCCGACGG GCTACCCTCG ATGTTCCAGG GTCTCGTCCG    3000
CGCTCGCGTC GCGCGCAAGG TCGCCAGCAA TAATGCCCTG GCCGCGTCGC TCACCCAGCG    3060
CCTCGCCTCC CTCCCGCCCA CCGACCGCGA GCGCATGCTG CTCGATCTCG TCCGCGCCGA    3120
AGCCGCCATC GTCCTCGGCC TCGCCTCGTT CGAATCGCTC GATCCCCGTC GCCCTCTTCA    3180
AGAGCTCGGT CTCGATTCCC TCATGGCCAT CGAGCTCCGA AATCGACTCG CCGCCGCCAC    3240
AGGCTTGCGA CTCCAAGCCA CCCTCCTCTT CGACCACCCG ACGCCCGCCG CGCTCGCGAC    3300
CCTGCTGCTC GGGAAGCTCC TCCAGCATGA AGCTGCCGAT CCTCGCCCCT TGGCCGCAGA    3360
GCTCGACAGG CTAGAGGCCA CTCTCTCCGC GATAGCCGTG GACGCTCAAG CACGCCCGAA    3420
GATCATATTA CGCCTGCAAT CCTGGTTGTC GAAGTGGAGC GACGCTCAGG CTGCCGACGC    3480
TGGACCGATT CTCGGCAAGG ATTTCAAGTC TGCTACGAAG GAAGAGCTCT TCGCTGCTTG    3540
TGACGAAGCG TTCGGAGGCC TGGGTAAATG AATAACGACG AGAAGCTTGT CTCCTACCTA    3600
CAGCAGGCGA TGAATGAGCT TCAGCGTGCT CATCAGCCCC TCCGCGCGGT CGAAGAGAAG    3660
GAGCACGAGC CCATCGCCAT CGTGGCGATG AGCTGCCGCT TCCGGGCGA CGTGCGCACG    3720
CCCGAGGATC TCTGGAAGCT CTTGCTCGAT GGGAAAGATG CTATCTCCGA CCTTCCCCCA    3780
AACCGTGGTT GGAAGCTCGA CGCGCTCGAC GTCCACGGTC GCTCCCCAGT CCGAGAGGGA    3840
GGCTTCTTCT ACGACGCAGA CGCCTTCGAT CCGGCCTTCT TCGGGATCAG CCCACGCGAG    3900
GCGCTCGCCA TCGATCCCCA GCAGCGGCTC CTCCTCGAGA TCTCATGGGA AGCCTTCGAG    3960
CGTGCGGGCA TCGACCCTGC CTCGCTCCAA GGGAGCCAAA GCGGCGTCTT CGTCGGCGTG    4020
ATACACAACG ACTACGACGC ATTGCTGGAG AACGCAGCTG GCGAACACAA AGGATTCGTT    4080
TCCACCGGCA GCACAGCGAG CGTCGCCTCC GGCCGGATCG CGTATACATT CGGCTTTCAA    4140
GGGCCCGCCA TCAGCGTGGA CACGGCGTGC AGCTCCTCGC TCGTCGCGGT TCACCTCGCC    4200
TGCCAGGCCC TGCGCCGTGG CGAATGCTCC CTGGCGCTCG CCGGCGGCGT GACCGTCATG    4260
GCCACGCCAG CAGTCTTCGT CGCGTTCGAT TCGAGAGCG CGGGCGCCCC CGATGGTCGC    4320
TGCAAGTCGT TCTCGGTGGA GGCCAACGGT TCGGGCTGGG CCGAGGGCGC CGGGATGCTC    4380
CTGCTCGAGC GCCTCTCCGA TGCCGTCCAA AACGGTCATC CCGTCCTCGC CGTCCTTCGA    4440
GGCTCCGCCG TCAACCAGGA CGGCCGGAGC CAAGGCCTCA CCGCGCCCAA TGGCCCTGCC    4500
CAAGAGCGCG TCATCCGGCA AGCGCTCGAC AGCGCGCGGC TCACTCCAAA GGACGTCGAC    4560
GTCGTCGAGG CTCACGGCAC GGGAACCACC CTCGGAGACC CCATCGAGGC ACAGGCCATT    4620
CTTGCCACCT ATGGCGAGGC CCATTCCCAA GACAGACCCC TCTGGCTTGG AAGTCTCAAG    4680
TCCAACCTGG GACATGCTCA GGCCGCGGCC GGCGTGGGAA GCGTCATCAA GATGGTGCTC    4740
GCGTTGCAGC AAGGCCTCTT GCCCAAGACC CTCCATGCCC AGAATCCCTC CCCCCACATC    4800
```

```
GACTGGTCTC CGGGCACGGT AAAGCTCCTG AACGAGCCCG TCGTCTGGAC GACCAACGGG  4860
CATCCTCGCC ACGCCGGCGT CTCCGCCTTC GGCATCTCCG GCACCAACGC CCACGTCATC  4920
CTCGAAGAGG CCCCCGCCAT CGCCCGGGTC GAGCCCGCAG CGTCACAGCC CGCGTCCGAG  4980
CCGCTTCCCG CAGCGTGGCC CGTGCTCCTG TCGGCCAAGA GCGAGGCGGC CGTGCGCGCC  5040
CAGGCAAAGC GGCTCCGCGA CCACCTCCTC GCCAAAAGCG AGCTCGCCCT CGCCGATGTG  5100
GCCTATTCGC TCGCGACCAC GCGCGCCAC TTCGAGCAGC GCGCCGCTCT CCTCGTCAAA  5160
GGCCGCGACG AGCTCCTCTC CGCCCTCGAT GCGCTGGCCC AAGGACATTC CGCCGCCGTG  5220
CTCGGACGAA GCGGGGCCCC AGGAAAGCTC GCCGTCCTCT TCACGGGGCA AGGAAGCCAG  5280
CGGCCCACCA TGGGCCGCGG CCTCTACGAC GTTTTCCCCG TCTTCCGGGA CGCCCTCGAC  5340
ACCGTCGGCG CCCACCTCGA CCGCGAGCTC GACCGCCCCC TGCGCGACGT CCTCTTCGCT  5400
CCCGACGGCT CCGAGCAGGC CGCGCGCCTC GAGCAAACCG CCTTCACCCA GCCGGCCCTG  5460
TTTGCCCTCG AAGTCGCCCT CTTTCAGCTT CTACAATCCT TCGGTCTGAA GCCCGCTCTC  5520
CTCCTCGGAC ACTCCATTGG CGAGCTCGTC GCCGCCCACG TCGCCGGCGT CCTTTCTCTC  5580
CAGGACGGCT GCACCCTCGT CGCCGCCCGC GCAAAGCTCA TGCAAGCGCT CCCACAAGGC  5640
GGCGCCATGG TCACCCTCCG AGCCTCCGAG GAGGAAGTCC GCGACCTTCT CCAGCCCTAC  5700
GAAGGCCGAG CTAGCCTCGC CGCCCTCAAT GGGCCTCTCT CCACCGTCGT CGCTGGCGAT  5760
GAAGACGCGG TGGTGGAGAT CGCCCGCCAG GCCGAAGCCC TCGGACGAAA GACCACACGC  5820
CTGCGCGTCA GCCACGCCTT CCATTCCCCG CACATGGACG GAATGCTCGA CGACTTCCGC  5880
CGCGTCGCCC AGAGCCTCAC CTACCATCCC GCACGCATCC CCATCATCTC CAACGTCACC  5940
GGCGCGCGCG CCACGGACCA CGAGCTCGCC TCGCCCGACT ACTGGGTCCG CCACGTTCGC  6000
CACACCGTCC GCTTCCTCGA CGGCGTACGT GCCCTTCACG CCGAAGGGGC ACGTGTCTTT  6060
CTCGAGCTCG GGCCTCACGC TGTCCTCTCC GCCCTTGCGC AAGACGCCCT CGGACAGGAC  6120
GAAGGCACGT CGCCATGCGC CTTCCTTCCC ACCCTCCGCA AGGGACGCGA CGACGCCGAG  6180
GCGTTCACCG CCGCGCTCGG CGCTCTCCAC TCCGCAGGCA TCACACCCGA CTGGAGCGCT  6240
TTCTTCGCCC CCTTCGCTCC ACGCAAGGTC TCCCTCCCCA CCTATGCCTT CCAGCGCGAG  6300
CGCTTCTGGC CCGACGCCTC CAAGGCACCC GGCGCCGACG TCAGCCACCT TGCTCCGCTC  6360
GAGGGGGGGC TCTGGCAAGC CATCGAGCGC GGGGACCTCG ATGCGCTCAG CGGTCAGCTC  6420
CACGTGGACG GCGACGAGCG GCGCGCCGCG CTCGCCCTGC TCCTTCCCAC CCTCTCGAGC  6480
TTTCGCCACG AGCGGCAAGA GCAGAGCACG GTCGACGCCT GGCGCTACCG TATCACCTGG  6540
AAGCCTCTGA CCACCGCCGA ACACCCGCC GACCTCGCCG GCACCTGGCT CGTCGTCGTG  6600
CCGGCCGCTC TGGACGACGA CGCGCTCCCC TCCGCGCTCA CCGAGGCGCT CACCCGGCGC  6660
GGCGCGCGCG TCCTCGCCTT GCGCCTGAGC CAGGCCACC TGGACCGCGA GGCTCTCGCC  6720
GAGCATCTGC GCCAGGCTTG CGCCGAGACC GCCCCGATTC GCGGCGTGCT CTCGCTCCTC  6780
GCCCTCGACG AGCGCCCCCT CGCAGACCGT CCTGCCCTGC CCGCCGGACT CGCCCTCTCG  6840
CTTTCTCTCG CTCAAGCCCT CGGCGACCTC GACCTCGAGG CGCCCTTGTG GTTCTTCACG  6900
CGCGGCGCCG TCTCCATTGG ACACTCTGAC CCCCTCGCCC ATCCGCCCA GGCCATGACC  6960
TGGGGCTTGG GCCGCGTCAT CGGCCTCGAG CACCCCGACC GGTGGGGAGG TCTCGTCGAC  7020
GTCTGCGCTG GGGTCGACGA GAGCGCCGTG GGCCGCTTGC TGCCGGCCCT CGCCGAGCGC  7080
CACGACGAAG ACCAGCTCGC TCTCCGCCCG GCCGGACTCT ACGCTCGCCG CATCGTCCGC  7140
GCCCCGCTCG GCGATGCGCC TCCCGCGCGC GACTTCACGC CCGGAGGCAC CATTCTCATC  7200
```

```
ACCGGCGGCA CCGGCGCCAT TGGCGCTCAC GTCGCCCGAT GGCTCGCTCG AAGAGGCGCT    7260
CAGCACCTCG TCCTCATCAG CCGCCGAGGC GCCGAGGCCC CTGGCGCCTC GGAGCTCCAC    7320
GACGAGCTCT CGGCCCTCGG CGCGCGCACC ACCCTCGCCG CGTGCGATGT CGCCGACCGG    7380
AATGCTGTCG CCACGCTTCT TGAGCAGCTC GACGCCGAAG GGTCGCAGGT CCGCGCCGTG    7440
TTCCACGCGA GCGGCATCGA ACACCACGCT CCGCTCGACG CCACCTCTTT CAGGGATCTC    7500
GCCGAGGTTG TCTCCGGCAA GGTCGAAGGT GCAAAGCACC TCCACGACCT GCTCGGCTCT    7560
CGACCCCTCG ACGCCTTTGT TCTCTTTTCG TCCGGCGCGG CCGTCTGGGG CGGCGGACAG    7620
CAAGGCGGCT ACGCGGCCGC AAACGCCTTC CTCGACGCCC TTGCCGAGCA TCGGCGCAGC    7680
GCTGGATTGA CAGCGACGTC GGTGGCCTGG GGCGCGTGGG GCGGCGGCGG CATGGCCACC    7740
GATCAGGCGG CAGCCCACCT CCAACAGCGC GGTCTGTCGC GGATGGCCCC CTCGCTTGCC    7800
CTGGCGGCGC TCGCGCTGGC TCTGGAGCAC GACGAGACCA CCGTCACCGT CGCCGACATC    7860
GACTGGGCGC GCTTTGCGCC TTCGTTCAGC GCCGCTCGCC CCGCCCGCT CCTGCGCGAT    7920
TTGCCCGAGG CGCAGCGCGC TCTCGAGACC AGCGAAGGCG CGTCCTCCGA GCATGGCCCG    7980
GCCCCCGACC TCCTCGACAA GCTCCGGAGC CGCTCGGAGA GCGAGCAGCT TCGTCTGCTC    8040
GTCTCGCTGG TGCGCCACGA GACGGCCCTC GTCCTCGGCC ACGAAGGCGC CTCCCATGTC    8100
GACCCCGACA AGGGCTTCCT CGATCTCGGT CTCGATTCGC TCATGGCCGT CGAGCTTCGC    8160
CGGCGCTTGC AACAGGCCAC CGGCATCAAG CTCCCGGCCA CCCTCGCCTT CGACCATCCC    8220
TCTCCTCATC GAGTCGCGCT CTTCTTGCGC GACTCGCTCG CCCACGCCCT CGGCACGAGG    8280
CTCTCCGTCG AGCCCGACGC CGCCGCGCTC CCGGCGCTTC GCGCCGCGAG CGACGAGCCC    8340
ATCGCCATCG TCGGCATGGC CCTCCGCCTG CCGGGCGGCG TCGGCGATGT CGACGCTCTT    8400
TGGGAGTTCC TGGCCCAGGG ACGCGACGGC GTCGAGCCCA TTCCAAAGGC CCGATGGGAT    8460
GCCGCTGCGC TCTACGACCC CGACCCCGAC GCCAAGACCA AGAGCTACGT CCGGCATGCC    8520
GCCATGCTCG ACCAGGTCGA CCTCTTCGAC CCTGCCTTCT TTGGCATCAG CCCCCGGGAG    8580
GCCAAACACC TCGACCCCCA GCACCGCCTG CTCCTCGAAT CTGCCTGGCA GGCCCTCGAA    8640
GACGCCGGCA TCGTCCCCCC CACCCTCAAG GATTCCCCCA CCGGCGTCTT CGTCGGCATC    8700
GGCGCCAGCG AATACGCATT GCGAGAGGCG AGCACCGAAG ATTCCGACGC TTATGCCCTC    8760
CAAGGCACCG CCGGGTCCTT TGCCGCGGGG CGCTTGGCCT ACACGCTCGG CCTGCAAGGG    8820
CCCGCGCTCT CGGTCGACAC CGCCTGCTCC TCCTCGCTCG TCGCCCTCCA CCTCGCCTGC    8880
CAAGCCCTCC GACAGGGCGA GTGCAACCTC GCCCTCGCCG CGGGCGTCTC CGTCATGGCC    8940
TCCCCCGAGG GCTTCGTCCT CCTTTCCCGC CTGCGCGCCT TGGCGCCCGA CGGCCGCTCC    9000
AAGACCTTCT CGGCCAACGC CGACGGCTAC GGACGCGGAG AAGGCGTCAT CGTCCTTGCC    9060
CTCGAGCGGC TCGGTGACGC CCTCGCCCGA GGACACCGCG TCCTCGCCCT CGTCCGCGGC    9120
ACCGCCATCA ACCACGACGG CGCGTCGAGC GGTATCACCG CCCCAACGG CACCTCCCAG    9180
CAGAAGGTCC TCCGCGCCGC GCTCCACGAC GCCCGCATCA CCCCCGCCGA CGTCGACGTC    9240
GTCGAGTGCC ATGGCACCGG CACCTCCTTG GGAGACCCCA TCGAGGTGCA AGCCCTGGCC    9300
GCCGTCTACG CCGACGGCAG ACCCGCTGAA AAGCCTCTCC TTCTCGGCGC GCTCAAGACC    9360
AACATCGGCC ATCTCGAGGC CGCCTCCGGC CTCGCGGGCG TCGCCAAGAT CGTCGCCTCC    9420
CTCCGCCATG ACGCCCTGCC CCCCACCCTC CACACGGGCC CGCGCAATCC CTTGATTGAT    9480
TGGGATACAC TCGCCATCGA CGTCGTTGAT ACCCGAGGT CTTGGGCCCG CCACGAAGAT    9540
AGCAGTCCCC GCCGCGCCGG CGTCTCCGCC TTCGGACTCT CCGGCACCAA CGCCCACGTC    9600
```

```
ATCCTCGAGG AGGCTCCCGC CGCCCTGTCG GGCGAGCCCG CCACCTCACA GACGGCGTCG    9660
CGACCGCTCC CCGCGGCGTG TGCCGTGCTC CTGTCGGCCA GGAGCGAGGC CGCCGTCCGC    9720
GCCCAGGCGA AGCGGCTCCG CGACCACCTC CTCGCCCACG ACGACCTCGC CCTTATCGAT    9780
GTGGCCTATT CGCAGGCCAC CACCCGCGCC CACTTCGAGC ACCGCGCCGC TCTCCTGGCC    9840
CGCGACCGCG ACGAGCTCCT CTCCGCGCTC GACTCGCTCG CCCAGGACAA GCCCGCCCCG    9900
AGCACCGTTC TCGGCCGGAG CGGAAGCCAC GGCAAGGTCG TCTTCGTCTT TCCTGGGCAA    9960
GGCTCGCAGT GGGAAGGGAT GGCCCTCTCC CTGCTCGACT CCTCGCCGGT CTTCCGCGCT   10020
CAGCTCGAAG CATGCGAGCG CGCGCTCGCT CCTCACGTCG AGTGGAGCCT GCTCGCCGTC   10080
CTGCGCCGCG ACGAGGGCGC CCCCTCCCTC GACCGCGTCG ACGTCGTACA GCCCGCCCTC   10140
TTTGCCGTCA TGGTCTCCCT GGCCGCCCTC TGGCGCTCGC TCGGCGTCGA GCCCGCCGCC   10200
GTCGTCGGCC ACAGCCAGGG CGAGATCGCC GCCGCCTTCG TCGCAGGCGC TCTCTCCCTC   10260
GAGGACGCGG CGCGCATCGC CGCCCTGCGC AGGAAAGCGC TCACCACCGT CGGCGGCAAC   10320
GGCGGCATGG CCGCCGTCGA GCTCGGCGCC TCCGACCTCC AGACCTACCT CGCTCCCTGG   10380
GGCGACAGGC TCTCCACCGC CGCCGTCAAC AGCCCCAGGG CTACCCTCGT ATCCGGCGAG   10440
CCCGCCGCCG TCGACGCGCT GCTCGACGTC CTCACCGCCA CCAAGGTGTT CGCCCGCAAG   10500
ATCCGCGTCG ACTACGCCTC CCACTCCGCC CAGATGGACG CCGTCCAAGA CGAGCTCGCC   10560
GCAGGTCTAG CCAACATCGC TCCTCGGACG TGCGAGCTCC CTCTTTATTC GACCGTCACC   10620
GGCACCAGGC TCGACGGCTC CGAGCTCGAC GGCGCGTACT GGTATCGAAA CCTCCGGCAA   10680
ACCGTCCTGT TCTCGAGCGC GACCGAGCGG CTCCTCGACG ATGGGCATCG CTTCTCCGTC   10740
GAGGTCAGCC CCCATCCCGT GCTCACGCTC GCCCTCCGCG AGACCTGCGA GCGCTCACCG   10800
CTCGATCCCG TCGTCGTCGG CTCCATTCGA CGAGAAGAAG GCCACCTCGC CCGCCTGCTC   10860
CTCTCCTGGG CGGAGCTCTC TACCCGAGGC CTCGCGCTCG ACTGGAAGGA CTTCTTCGCG   10920
CCCTACGCTC CCCGCAAGGT CTCCCTCCCC ACCTACCCCT TCCAGCGAGA GCGGTTCTGG   10980
CTCGACGTCT CCACGGACGA ACGCTTCCGA CGTCGCCTCC GCAGGCCTGA CCTCGGCCGA   11040
CCAATCCCGC TGCTCGGCGC CGCCGTCGCC TTCGCCGACC GCGGTGGCTT TCTCTTTACA   11100
GGGCGGCTCT CCCTCGCAGA GCACCCGTGG CTCGAAGGCC ATGCCGTCTT CGGCACACCC   11160
ATCCTACCGG GCACCGGCTT TCTCGAGCTC GCCCTGCACG TCGCCCACCG CGTCGGCCTC   11220
GACACCGTCG AAGAGCTCAC GCTCGAGGCC CCTCTCGCTC TCCCATCGCA GGACACCGTC   11280
CTCCTCCAGA TCTCCGTCGG GCCCGTGGAC GACGCAGGAC GAAGGGCGCT CTCTTTCCAT   11340
AGCCGACAAG AGGACGCGCT TCAGGATGGC CCCTGGACTC GCCACGCCAG CGGCTCTCTC   11400
TCGCCGGCGA CCCCATCCCT CTCCGCCGAT CTCCACGAGT GGCCTCCCTC GAGTGCCATC   11460
CCGGTGGACC TCGAAGGCCT CTACGCAACC CTCGCCAACC TCGGGCTTGC CTACGGCCCC   11520
GAGTTCCAGG GCCTCCGCTC CGTCTACAAG CGCGGCGACG AGCTCTTTGC CGAAGCCAAG   11580
CTCCCGGAAG CGGCCGAAAA GGATGCCGCC CGGTTTGCCC TCCACCCTGC GCTGCTCGAC   11640
AGCGCCCTGC ATGCACTGGC CTTTGAGGAC GAGCAGAGAG GGACGGTCGC TCTGCCCTTC   11700
TCGTGGAGCG GAGTCTCGCT GCGCTCCGTC GGTGCCACCA CCTTGCGCGT GCGCTTCCAC   11760
CGTCCCAAGG GTGAATCCTC CGTCTCGATC GTCCTGGCCG ACGCCGCAGG TGACCCTCTT   11820
GCCTCGGTGC AAGCGCTCGC CATGCGGACG ACGTCCGCCG CGCAGCTCCG CACCCCGGCA   11880
GCTTCCCACC ATGATGCGCT CTTCCGCGTC GACTGGAGCG AGCTCCAAAG CCCCACTTCA   11940
CCGCCTGCCG CCCCGAGCGG CGTCCTTCTC GGCACAGGCG GCCACGATCT CGCGCTCGAC   12000
```

```
GCCCCGCTCG CCCGCTACGC CGACCTCGCT GCCCTCCGAA GCGCCCTCGA CCAGGGCGCT    12060
TCGCCTCCCG GCCTCGTCGT CGCCCCCTTC ATCGATCGAC CGGCAGGCGA CCTCGTCCCG    12120
AGCGCCCACG AGGCCACCGC GCTCGCACTC GCCCTCTTGC AAGCCTGGCT CGCCGACGAA    12180
CGCCTCGCCT CGTCGCGCCT CGTCCTCGTC ACCCGACGCG CCGTCGCCAC CCACACCGAA    12240
GACGACGTCA AGGACCTCGC TCACGCGCCG CTCTGGGGGC TCGCGCGCTC CGCGCAAAGT    12300
GAGCACCCAG ACCTCCCGCT CTTCCTCGTC GACATCGACC TCAGCGAGGC CTCCCAGCAG    12360
GCCCTGCTAG GCGCGCTCGA CACAGGAGAA CGCCAGCTCG CCCTCCGCAA CGGGAAACCC    12420
CTCATCCCGA GGTTGGCGCA ACCACGCTCG ACGGACGCGC TCATCCCGCC GCAAGCACCC    12480
ACGTGGCGCC TCCATATTCC GACCAAAGGC ACCTTCGACG CGCTCGCCCT CGTCGACGCC    12540
CCCGAGGCCC AGGCGCCCCT CGCACACGGC CAAGTCCGCA TCGCCGTGCA CGCGGCAGGG    12600
CTCAACTTCC GCGATGTCGT CGACACCCTT GGCATGTATC CGGGCGACGC GCCGCCGCTC    12660
GGAGGCGAAG GCGCGGGCAT CGTTACTGAA GTCGGTCCAG GTGTCTCCCG ATACACCGTA    12720
GGCGACCGGG TGATGGGGGT CTTCGGCGCA GCCTTTGGTC CCACGGCCAT CGCCGACGCC    12780
CGCATGATCT GCCCCATCCC CCACGCCTGG TCCTTCGCCC AAGCCGCCAG CGTCCCCATC    12840
ATCTATCTCA CCGCCTACTA TGGACTCGTC GATCTCGGGC ATCTGAAACC CAATCAACGT    12900
GTCCTCATCC ATGCGGCCGC CGGCGGCGTC GGGACGGCCG CCGTTCAGCT CGCACGCCAC    12960
CTCGGCGCCG AGGTCTTTGC CACCGCCAGT CCAGGGAAGT GGAGCGCTCT CCGCGCGCTC    13020
GGCTTCGACG ATGCGCACCT CGCGTCCTCA CGTGACCTGG GCTTCGAGCA GCACTTCCTG    13080
CGCTCCACGC ATGGGCGCGG CATGGATGTC GTCCTCGACT GTCTGGCACG CGAGTTCGTC    13140
GACGCCTCGC TGCGCCTCAT GCCGAGCGGT GGACGCTTCA TCGAGATGGG AAAGACGGAC    13200
ATCCGTGAGC CCGACGCGAT CGGCCTCGCC TACCCTGGCG TCGTTTACCG CGCCTTCGAC    13260
GTCACAGAGG CCGGACCGGA TCGAATTGGG CAGATGCTCG CAGAGCTGCT CAGCCTCTTC    13320
GAGCGCGGTG TGCTTCGTCT GCCACCCATC ACATCCTGGG ACATCCGTCA TGCCCCCCAG    13380
GCCTTCCGCG CGCTCGCCCA GGCGCGGCAT GTTGGGAAGT TCGTCCTCAC CATTCCCCGT    13440
CCGATCGATC CCGAGGGGAC CGTCCTCATC ACGGGAGGCA CCGGGACGCT AGGAGTCCTG    13500
GTCGCACGCC ACCTCGTCGC GAAACACAGC GCCAAACACC TGCTCCTCAC CTCGAGGAAG    13560
GGCGCGCGTG CTCCGGGCGC GGAGGCTCTG CGAAGCGAGC TCGAAGCGCT GGGGGCCTCG    13620
GTCACCCTCG TCGCGTGCGA CGTGGCCGAC CCACGCGCCC TCCGGACCCT CCTGGACAGC    13680
ATCCCGAGGG ATCATCCGAT CACGGCCGTC GTGCACGCCG CCGGCGCCCT CGACGACGGG    13740
CCGCTCGGTA GCATGAGCGC CGAGCGCATC GCTCGCGTCT TTGACCCCAA GCTCGATGCC    13800
GCTTGGTACT TGCATGAGCT CACCCAGGAC GAGCCGGTCG CGGCCTTCGT CCTCTTCTCG    13860
GCCGCCTCCG GCGTCCTTGG TGGTCCAGGT CAGTCGAACT ACGCCGCTGC CAATGCCTTC    13920
CTCGATGCGC TCGCACATCA CCGGCGCGCC CAAGGACTCC CAGCCGCTTC GCTCGCCTGG    13980
GGCTACTGGG CCGAGCGCAG TGGGATGACC CGGCACCTCA GCGCCGCCGA CGCCGCTCGC    14040
ATGAGGCGCG CCGGCGTCCG GCCCCTCGAC ACTGACGAGG CGCTCTCCCT CTTCGATGTG    14100
GCTCTCTTGC GACCCGAGCC CGCTCTGGTC CCCGCCCCCT TCGACTACAA CGTGCTCAGC    14160
ACGAGTGCCG ACGGCGTGCC CCCGCTGTTC CAGCGTCTCG TCCGCGCTCG CATCGCGCGC    14220
AAGGCCGCCA GCAATACTGC CCTCGCCTCG TCGCTTGCAG AGCACCTCTC CTCCCTCCCG    14280
CCCGCCGAAC GCGAGCGCGT CCTCCTCGAT CTCGTCCGCA CCGAAGCCGC CTCCGTCCTC    14340
GGCCTCGCCT CGTTCGAATC GCTCGATCCC CATCGCCCTC TACAAGAGCT CGGCCTCGAT    14400
```

-continued

```
TCCCTCATGG CCCTCGAGCT CCGAAATCGA CTCGCCGCCG CCGCCGGGCT GCGGCTCCAG    14460
GCTACTCTCC TCTTCGACTA TCCAACCCCG ACTGCGCTCT CACGCTTTTT CACGACGCAT    14520
CTCTTCGGGG GAACCACCCA CCGCCCCGGC GTACCGCTCA CCCCGGGGGG GAGCGAAGAC    14580
CCTATCGCCA TCGTGGCGAT GAGCTGCCGC TTCCCGGGCG ACGTGCGCAC GCCCGAGGAT    14640
CTCTGGAAGC TCTTGCTCGA CGGACAAGAT GCCATCTCCG GCTTTCCCCA AAATCGCGGC    14700
TGGAGTCTCG ATGCGCTCGA CGCCCCCGGT CGCTTCCCAG TCCGGGAGGG GGGCTTCGTC    14760
TACGACGCAG ACGCCTTCGA TCCGGCCTTC TTCGGGATCA GTCCACGTGA AGCGCTCGCC    14820
GTTGATCCCC AACAGCGCAT TTGCTCGAG ATCACATGGG AAGCTTCGA GCGTGCAGGC     14880
ATCGACCCGG CCTCCCTCCA AGGAAGCCAA AGCGGGGTCT TCGTTGGCGT ATGGCAGAGC    14940
GACTACCAAT GCATCGCTGG TGAACGCGAC TGGCGAATAC AAGGACTCGT TGCCACCGGT    15000
AGCGCAGCGC GTCCGTCCGG CCGAATCGCA TACACGTTCG GACTTCAAGG GCCCGCCATC    15060
AGCGTGGAGA CGGCGTGCAG CTTCCTCGTC GCGGTTCACC TCGCCTGCCA GGCCCCCCCC    15120
CACGGCGAAT ACTCCCTGGC GCTCGCTGGC GGCGTGACCA TCATGGCCAC GCCAGCCATA    15180
TTCATCGCGT TCGACTCCGA GAGCGCGGGT GCCCCCGACG GTCGCTGCAA GGCCTTCTCG    15240
CCGGAAGCCG ACGGTTCGGG CTGGGCCGAA GGCGCCGGGA TGCTCCTGCT CGAGCGCCTC    15300
TCCGATGCCG TCCAAAACGG TCATCCCGTC CTCGCCGTCC TTCGAGGCTC CGCCGTCAAC    15360
CAGGACGGCC GGAGCCAAGG CCTCACCGCG CCCAATGGCC CTGCCCAGGA GCGCGTCATC    15420
CGGCAAGCGC TCGACAGCGC GCGGCTCACT CCAAAGGACG TCGACGTCGT CGAGGCTCAC    15480
GGCACGGGAA CCACCCTCGG AGACCCCATC GAGGCACAGG CCGTTTTTGC CACCTATGGC    15540
GAGGCCCATT CCCAAGACAG ACCCCTCTGG CTTGGAAGCC TCAAGTCCAA CCTGGGACAT    15600
ACTCAGGCCG CGGCCGGCGT CGGCGGCATC ATCAAGATGG TGCTCGCGTT GCAGCACGGT    15660
CTCTTGCCCA AGACCCTCCA TGCCCAGAAT CCCTCCCCCC ACATCGACTG GTCTCCAGGC    15720
ATCGTAAAGC TCCTGAACGA GGCCGTCGCC TGGACGACCA GCGGACATCC TCGCCGCGCC    15780
GGTGTTTCCT CGTTCGGCGT CTCCGGCACC AACGCCCATG TCATCCTCGA AGAGGCTCCC    15840
GCCGCCACGC GGGCCGAGTC AGGCGCTTCA CAGCCTGCAT CGCAGCCGCT CCCCGCGGCG    15900
TGGCCCGTCG TCCTGTCGGC CAGGAGCGAG GCCGCCGTCC GCGCCCAGGC TCAAAGGCTC    15960
CGCGAGCACC TGCTCGCCCA AGGCGACCTC ACCCTCGCCG ATGTGGCCTA TTCGCTGGCC    16020
ACCACCCGCG CCCACTTCGA GCACCGCGCC GCTCTCGTAG CCCACGACCG CGACGAGCTC    16080
CTCTCCGCGC TCGACTCGCT CGCCCAGGAC AAGCCCGCAC CGAGCACCGT CCTCGGACGG    16140
AGCGGAAGCC ACGGCAAGGT CGTCTTCGTC TTTCCTGGGC AAGGCTCGCA GTGGGAAGGG    16200
ATGGCCCTCT CCCTGCTCGA CTCCTCGCCC GTCTTCCGCA CACAGCTCGA AGCATGCGAG    16260
CGCGCGCTCC GTCCTCACGT CGAGTGGAGC CTGCTCGCCG TCCTGCGCCG CGACGAGGGC    16320
GCCCCCTCCC TCGACCGCGT CGACGTCGTG CAGCCCGCCC TCTTTGCCGT CATGGTCTCC    16380
CTGGCCGCCC TCTGGCGCTC GCTCGGCGTC GAGCCCGCCG CCGTCGTCGG CCACAGCCAG    16440
GGCGAGATAG CCGCCGCCTT CGTCGCAGGC GCTCTCTCCC TCGAGGACGC GGCCCGCATC    16500
GCCGCCCTGC GCAGCAAAGC GTCACCACCG TCGCCGGCAA CGGGCATGGC CGCCGTCGAG    16560
CTCGGCGCCT CCGACCTCCA GACCTACCTC GCTCCCTGGG GCGACAGGCT CTCCATCGCC    16620
GCCGTCAACA GCCCCAGGGC CACGCTCGTA TCCGGCGAGC CCGCCGCCGT CGACGCGCTG    16680
ATCGACTCGC TCACCGCAGC GCAGGTCTTC GCCCGAAGAG TCCGCGTCGA CTACGCCTCC    16740
CACTCAGCCC AGATGGACGC CGTCCAAGAC GAGCTCGCCG CAGGTCTAGC CAACATCGCT    16800
```

-continued

```
CCTCGGACGT GCGAGCTCCC TCTTTATTCG ACCGTCACCG GCACCAGGCT CGACGGCTCC    16860
GAGCTCGACG GCGCGTACTG GTATCGAAAC CTCCGGCAAA CCGTCCTGTT CTCGAGCGCG    16920
ACCGAGCGGC TCCTCGACGA TGGGCATCGC TTCTTCGTCG AGGTCAGCCC TCATCCCGTG    16980
CTCACGCTCG CCCTCCGCGA GACCTGCGAG CGCTCACCGC TCGATCCCGT CGTCGTCGGC    17040
TCCATTCGAC GCGACGAAGG CCACCTCCCC CGTCTCCTTG CTCTCTTGGG CCGAGCTCTA    17100
TGGCCGGGCC TCACGCCCGA GTGGAAGGCC TTCTTCGCGC CCTTCGCTCC CCGCAAGGTC    17160
TCACTCCCCA CCTACGCCTT CCAGCGCGAG CGTTTCTGGC TCGACGCCCC CAACGCACAC    17220
CCCGAAGGCG TCGCTCCCGC TGCGCCGATC GATGGGCGGT TTTGGCAAGC CATCGAACGC    17280
GGGGACCTCG ACGCGCTCAG CGGCCAGCTC CACGCGGACG GCGACGAGCA GCGCGCCGCC    17340
CTCGCCCTGC TCCTTCCCAC CCTCTCGAGC TTTCACCACC AGCGCCAAGA GCAGAGCACG    17400
GTCGACACCT GGCGCTACCG CATCACGTGG AGGCCTCTGA CCACCGCCGC CACGCCCGCC    17460
GACCTCGCCG GCACCTGGCT CCTCGTCGTG CCGTCCGCGC TCGGCGACGA CGCGCTCCCT    17520
GCCACGCTCA CCGATGCGCT TACCCGGCGC GGCGCGCGTG TCCTCGCGCT GCGCCTGAGC    17580
CAGGTTCACA TAGGCCGCGC GGCTCTCACC GAGCACCTGC GCGAGGCTGT TGCCGAGACT    17640
GCCCCGATTC GCGGCGTGCT CTCCCTCCTC GCCCTCGACG AGCGCCCCT CGCGGACCAT    17700
GCCGCCCTGC CCGCGGGCCT TGCCCTCTCG CTCGCCCTCG TCCAAGCCCT CGGCGACCTC    17760
GCCCTCGAGG CTCCCTTGTG GCTCTTCACG CGCGGCGCCG TCTCGATTGG ACACTCCGAC    17820
CCACTCGCCC ATCCCACCCA GGCCATGATC TGGGGCTTGG GCCGCGTCGT CGGCCTCGAG    17880
CACCCCGAGC GGTGGGGCGG GCTCGTCGAC CTCGGCGCAG CGCTCGACGC GAGCGCCGCA    17940
GGCCGCTTGC TCCCGGCCCT CGCCCAGCGC CACGACGAAG ACCAGCTCGC GCTGCGCCCG    18000
GCCGGCCTCT ACGCACGCCG CTTCGTCCGC GCCCCGCTCG GCGATGCGCC TGCCGCTCGC    18060
GGCTTCATGC CCCGAGGCAC CATCCTCATC ACCGGTGGTA CCGGCGCCAT TGGCGCTCAC    18120
GTCGCCCGAT GGCTCGCTCG AAAAGGCGCT GAGCACCTCG TCCTCATCAG CCGACGAGGG    18180
GCCCAGGCCG AAGGCGCCGT GGAGCTCCAC GCCGAGCTCA CCGCCCTCGG CGCGCGCGTC    18240
ACCTTCGCCG CGTGCGATGT CGCCGACAGG AGCGCTGTCG CCACGCTTCT CGAGCAGCTC    18300
GACGCCGGAG GGCCACAGGT GAGCGCCGTG TTCCACGCGG GCGGCATCGA GCCCCACGCT    18360
CCGCTCGCCG CCACCTCCAT GGAGGATCTC GCCGAGGTTG TCTCCGGCAA GGTACAAGGT    18420
GCAAGACACC TCCACGACCT GCTCGGCTCT CGACCCCTCG ACGCCTTTGT TCTCTTCTCG    18480
TCCGGCGCGG TCGTCTGGGG CGGCGGACAA CAAGGCGGCT ATGCCGCTGC GAACGCCTTC    18540
CTCGATGCCC TGGCCGAGCA GCGGCGCAGC CTTGGGCTGA CGGCGACATC GGTGGCCTGG    18600
GGCGTGTGGG GCGGCGGCGG CATGGCTACC GGGCTCCTGG CAGCCCAGCT AGAGCAACGC    18660
GGTCTGTCGC CGATGGCCCC CTCGCTGGCC GTGGCGACGC TCGCGCTGGC GCTGGAGCAC    18720
GACGAGACCA CCCTCACCGT CGCCGACATC GACTGGGCGC GCTTTGCGCC TTCGTTCAGC    18780
GCCGCTCGCT CCCGCCCGCT CCTGCGCGAT TTGCCCGAGG CGCAGCGCGC TCTCGAAGCC    18840
AGCGCCGATG CGTCCTCCGA GCAAGACGGG GCCACAGGCC TCCTCGACAA GCTCCGAAAC    18900
CGCTCGGAGA GCGAGCAGAT CCACCTGCTC TCCTCGCTGG TGCGCCACGA AGCGGCCCTC    18960
GTCCTGGGCC ATACCGACGC CTCCCAGGTC GACCCCACA AGGGCTTCAT GGACCTCGGC    19020
CTCGATTCGC TCATGACCGT CGAGCTTCGT CGGCGCTTGC AGCAGGCCAC CGGCATCAAG    19080
CTCCCGGCCA CCCTCGCCTT CGACCATCCC TCTCCTCATC GCGTCGCGCT CTTCTTGCGC    19140
GACTCGCTCG CCCACGCCCT CGGCGCGAGG CTCTCCGTCG AGCGCGACGC CGCCGCGCTC    19200
```

```
CCGGCGCTTC GCTCGGCGAG CGACGAGCCC ATCGCCATCG TCGGCATGGC CCTCCGCTTG    19260
CCGGGCGGCA TCGGCGATGT CGACGCTCTT TGGGAGTTCC TCGCCCAAGG ACGCGACGCC    19320
GTCGAGCCCA TTCCCCATGC CCGATGGGAT GCCGGTGCCC TCTACGACCC CGACCCCGAC    19380
GCCAAGGCCA AGAGCTACGT CCGGCATGCC GCCATGCTCG ACCAGGTCGA CCTCTTCGAT    19440
CCTGCCTTCT TTGGCATCAG CCCTCGCGAG GCCAAATACC TCGACCCCCA GCACCGCCTG    19500
CTCCTCGAAT CTGCCTGGCT GGCCCTCGAG GACGCCGGCA TCGTCCCCTC CACCCTCAAG    19560
GATTCTCCCA CCGGCGTCTT CGTCGGCATC GGCGCCAGCG AATACGCACT GCGAAACACG    19620
AGCTCCGAAG AGGTCGAAGC GTATGCCCTC CAAGGCACCG CCGGGTCCTT TGCCGCGGGG    19680
CGCTTGGCCT ACACGCTCGG CCTGCAAGGG CCCGCGCTCT CGGTCGACAC CGCCTGCTCC    19740
TCCTCGCTCG TCGCCCTCCA CCTCGCCTGC CAAGCCCTCC GACAGGGCGA GTGCAACCTC    19800
GCCCTCGCCG CGGGCGTCTC CGTCATGGCC TCCCCCGGGC TCTTCGTCGT CCTTTCCCGC    19860
ATGCGTGCTT TGGCGCCCGA TGGCCGCTCC AAGACCTTCT CGACCAACGC CGACGGCTAC    19920
GGACGCGGAG AGGGCGTCGT CGTCCTTGCC CTCGAGCGGC TCGGCGACGC CCTCGCCCGA    19980
GGACACCGCG TCCTCGCCCT CGTCCGCGGC ACCGCCATGA ACCATGACGG CGCGTCGAGC    20040
GGCATCACCG CCCCCAATGG CACCTCCCAC CAGAAGGTCC TCCGCGCCGC GCTCCACGAC    20100
GCCCATATCG GCCCTGCCGA CGTCGACGTC GTCGAATGCC ATGGCACCGG CACCTCCTTG    20160
GGAGACCCCA TCGAGGTGCA AGCCCTGGCC GCCGTCTACG CCGATGGCAG ACCCGCTGAA    20220
AAGCCTCTCC TTCTCGGCGC ACTCAAGACC AACATTGGCC ATCTCGAGGC CGCCTCCGGC    20280
CTCGCGGGCG TCGCCAAGAT CGTCGCCTCC CTCGCCATG ACGCCCTGCC CCCCACCCTC    20340
CACACGACCC CGCGCAATCC CCTGATCGAG TGGGATGCGC TCGCCATCGA CGTCGTCGAT    20400
GCCACGAGGG CGTGGGCCCG CCACGAAGAT GGCAGTCCCC GCCGCGCCGG CGTCTCCGCC    20460
TTCGGACTCT CCGGCACCAA CGCCCACGTT ATCCTCGAAG AGGCTCCCGC GATCCGCAG    20520
GCCGAGCCCA CCGCGGCACA GCTCGCGTCG CAGCCGCTTC CCGCAGCCTG GCCCGTGCTC    20580
CTGTCGGCCA GGAGCGAGCC GGCCGTGCGC GCCCAGGCCC AGAGGCTCCG CGACCACCTC    20640
CTCGCCCACG ACGACCTCGC CCTGGCCGAT GTAGCCTACT CGCTCGCCAC CACCCGGGCT    20700
ACCTTCGAGC ACCGTGCCGC TCTCGTGGTC CACGACCGCG AAGAGCTCCT CTCCGCGCTC    20760
GATTCGCTCG CCCAGGGAAG GCCCGCCCCG AGCACCGTCG TCGAACGAAG CGGAAGCCAC    20820
GGCAAGGTCG TCTTCGTCTT TCCTGGGCAA GGCTCGCAGT GGGAAGGGAT GGCCCTCTCC    20880
CTGCTCGATA CCTCGCCGGT CTTCCGGGCA CAGCTCGAAG CGTGCGAGCG CGCCCTCGCG    20940
CCCCACGTGG ACTGGTCGCT GCTCGCGGTG CTCCGCGGCG AGGAGGGCGC GCCCCGCTC    21000
GACCGGGTCG ACGTGGTCCA GCCCGCGCTG TTCTCGATGA TGGTCTCGCT GGCCGCCCTG    21060
TGGCGCTCCA TGGGCGTCGA GCCCGACGCG GTGGTCGGCC ATAGCCAGGG CGAGATCGCC    21120
GCGGCCTGTG TGGCGGGCGC GCTGTCGCTC GAGGACGCTG CCAAGCTGGT GGCGCTGCGC    21180
AGCCGTGCGC TCGTGGAGCT CGCCGGCCAG GGGGCCATGG CCGCGGTGGA GCTGCCGGAG    21240
GCCGAGGTCG CACGGCGCCT CCAGCGCTAT GGCGATCGGC TCTCCATCGG GGCGATCAAC    21300
AGCCCTCGTT TCACGACGAT CTCCGGCGAG CCCCCTGCCG TCGCCGCCCT GCTCCGCGAT    21360
CTGGAGTCCG AGGGCGTCTT CGCCCTCAAG CTGAGTTACG ACTTCGCCTC CCACTCCGCG    21420
CAGGTCGAGT CGATTCGCGA CGAGCTCCTC GATCTCCTGT CGTGGCTCGA GCCGCGCTCG    21480
ACGGCGGTCC CGTTCTACTC CACGGTGAGC GGCGCCGCGA TCGACGGGAG CGAGCTCGAC    21540
GCCGCCTACT GGTACCGGAA CCTCCGGCAG CCGGTCCGCT TCGCAGACGC TGTGCAAGGC    21600
```

```
CTCCTTGCCG GAGAACATCG CTTCTTCGTG GAGGTGAGCC CCAGTCCTGT GCTGACCTTG   21660
GCCTTGCACG AGCTCCTCGA AGCGTCGGAG CGCTCGGCGG CGGTGGTCGG CTCTCTGTGG   21720
AGCGACGAAG GGGATCTACG GCGCTTCCTC GTCTCGCTCT CCGAGCTCTA CGTCAACGGC   21780
TTCGCCCTGG ATTGGACGAC GATCCTGCCC CCCGGGAAGC GGGTGCCGCT GCCCACCTAC   21840
CCCTTCCAGC GCGAGCGCTT CTGGCTCGAC GCCTCCACGG CACCCGCCGC CGGCGTCAAC   21900
CACCTTGCTC CGCTCGAGGG GCGGTTCTGG CAGGCCATCG AGAGCGGGAA TATCGACGCG   21960
CTCAGCGGCC AGCTCCACGT GGACGGCGAC GAGCAGCGCG CCGCCCTTGC CCTGCTCCTT   22020
CCCACCCTCG CGAGCTTTCG CCACGAGCGG CAAGAGCAGG GCACGGTCGA CGCCTGGCGC   22080
TACCGCATCA CGTGGAAGCC TCTGACCACC GCCACCACGC CCGCCGACCT GGCCGGCACC   22140
TGGCTCCTCG TCGTGCCGGC CGCTCTGGAC GACGACGCGC TCCCCTCCGC GCTCACCGAG   22200
GCGCTCGCCC GGCGCGGCGC GCGCGTCCTC GCCGTGCGCC TGAGCCAGGC CCACCTGGAC   22260
CGCGAGGCTC TCGCCGAGCA CCTGCGCCAG GCTTGCGCCG AGACCGCGCC GCCTCGCGGC   22320
GTGCTCTCGC TCCTCGCCCT CGACGAAAGT CCCCTCGCCG ACCATGCCGC CGTGCCCGCG   22380
GGACTCGCCT TCTCGCTCAC CCTCGTCCAA GCCCTCGGCG ACATCGCCCT CGACGCGCCC   22440
TTGTGGCTCT TCACCCGCGG CGCCGTCTCC GTCGGACACT CCGACCCCAT CGCCCATCCG   22500
ACGCAGGCGA TGACCTGGGG CCTGGGCCGC GTCGTCGGCC TCGAGCACCC CGAGCGCTGG   22560
GGAGGGCTCG TCGACGTCGG CGCAGCGATC GACGCGAGCG CCGTGGGCCG CTTGCTCCCG   22620
GTCCTCGCCC TGCGCAACGA TGAGGACCAG CTCGCTCTCC GCCGGCCGG GTTCTACGCT   22680
CGCCGCCTCG TCCGCGCTCC GCTCGGCGAC GCGCCGCCCG CACGTACCTT CAAGCCCCGA   22740
GGCACCCTCC TCATCACCGG AGGCACCGGC GCCGCTGGCG CTCACGTCGC CCGATGGCTC   22800
GCTCGAGAAG GCGCAGAGCA CCTCGTCCTC ATCAGCCGCC GAGGGCCCA GGCCGAGGGC   22860
GCCTCGGAGC TCCACGCCGA GCTCACGGCC CTGGGCGCGC GCGTCACCTT CGCCGCGTGT   22920
GATGTCGCCG ACAGGAGCGC TGTCGCCACG CTTCTCGAGC AGCTCGACGC CGAAGGGTCG   22980
CAGGTCCGCG CCGTGTTCCA CGCGGGCGGC ATCGGGCGCC ACGCTCCGCT CGCCGCCACC   23040
TCTCTCATGG AGCTCGCCGA CGTTGTCTCT GCCAAGGTCC TAGGCGCAGG GAACCTCCAC   23100
GACCTGCTCG GTCCTCGACC CCTCGACGCC TTCGTCCTTT TCTCGTCCAT CGCAGGCGTC   23160
TGGGCGGCG GACAACAAGC CGGATACGCC GCCGGAAACG CCTTCCTCGA CGCCCTGGCC   23220
GACCAGCGGC GCAGTCTTGG ACAGCCGGAC ACGTCCGTGG TGTGGGCGC GTGGGCGGC   23280
GGCGGTGGTA TATTCACGGG GCCCCTGGCA GCCCAGCTGG AGCAACGTCG TCTGTCGCCG   23340
ATGGCCCCTT CGCTGGCCGT GGCGGCGCTC GCGCAAGCCC TGGAGCACGA CGAGACCACC   23400
GTCACCGTCG CCGACATCGA CTGGGCGCGC TTTGCGCCTT CGATCAGCGT CGCTCGCTCC   23460
CGCCGCTCCT GCGCGACTTG CCCGAGCAGC GCGCCCTCGA AGACAGAGAA GGCGCGTCCT   23520
CCTCCGAGCA CGGCCCGGCC CCCCGACCTC CTCGACAAGC TCCGGAGCCG CTCGGAGAGC   23580
GAGCAGCTCC GTCTGCTCGC CGCGCTGGTG TGCGACGAGA CGGCCCTCGT CCTCGGCCAC   23640
GAAGGCCGCT TCCCAGCTCG ACCCCGACAA GGCTTCTTCG ACCTCGGTCT CGATTCGATC   23700
ATGACCGTCG AGCTTCGTCG GCGCTTGCAA CAGGCCACCG GCATCAAGCT CCCGGCCACC   23760
CTCGCCTTCG ACCATCCCTC TCCTCATCGC GTCGCGCTCT TCATGCGCGA CTCGCTCGCC   23820
CACGCCCTCG GCACGAGGCT CTCCGCCGAG GCGACGCCGC CGCGCTCCGG CCGCGCCTCG   23880
AGCGACGAGC CCATCGCCAT CGTCGGCATG GCCCTGCCGC TGCCGGGCGG CGTCGGCGAT   23940
GTCGACGCTC TTTGGGAGTT CCTCCACCAA GGGCGCGACG CGGTCGAGCC CATTCCACAG   24000
```

```
AGCCGCTGGG ACGCCGGTGC CCTCTACGAC CCCGACCCCG ACGCCGACGC CAAGAGCTAC    24060
GTCCGGCATG CCGCGATGCT CGACCAGATC GACCTCTTCG ACCCTGCCTT CTTCGGCATC    24120
AGCCCCCGGG AGGCCAAACA CCTCGACCCC CAGCACCGCC TGCTCCTCGA ATCTGCCTGG    24180
CTGGCCCTCG AGGACGCCGG CATCGTCCCC ACCTCCCTCA AGGACTCCCT CACCGGCGTC    24240
TTCGTCGGCA TCTGCGCCGG CGAATACGCG ATGCAAGAGG CGAGCTCGGA AGGTTCCGAG    24300
GTTTACTTCA TCCAAGGCAC TTCCGCGTCC TTTGGCGCGG GGGCTTGGC CTATACGCTC     24360
GGGCTCCAGG GGCCGCGATC TTCGGTCGAC ACCGCCTGCT CCTCCTCGCT CGTCTCCCTC    24420
CACCTCGCCT GCCAAGCCCT CCGACAGGGC GAGTGCAACC TCGCCCTCGC CGCGGGCGTG    24480
TCGCTCATGG TCTCCCCCCA GACCTTCGTC ATCCTTTCCC GTCTGCGCGC CTTGGCGCCC    24540
GACGGCCGCT CCAAGACCTT CTCGGACAAC GCCGACGGCT ACGGACGCGG AGAAGGCGTC    24600
GTCGTCCTTG CCCTCGAGCG GATCGGCGAC GCCCTCGCCC GGAGACACCG CGTCCTCGTC    24660
CTCGTCCGCG GCACCGCCAT CAACCACGAC GGCGCGTCGA GCGGTATCAC CGCCCCCAAC    24720
GGCACCTCCC AGCAGAAGGT CCTCCGGGCC GCGCTCCACG ACGCCCGCAT CACCCCCGCC    24780
GACGTCGACG TCGTCGAGTG CCATGGCACC GGCACCTCGC TGGGAGACCC CATCGAGGTG    24840
CAAGCCCTGG CCGCCGTCTA CGCCGACGGC AGACCCGCTG AAAAGCCTCT CCTTCTCGGC    24900
GCGCTCAAGA CCAACATCGG CCATCTCGAG GCCGCCTCCG GCCTCGCGGG CGTCGCCAAG    24960
ATGGTCGCCT CGCTCCGCCA CGACGCCCTG CCCCCCACCC TCCACGCGAC CCCACGCAAT    25020
CCCCTCATCG AGTGGGAGGC GCTCGCCATC GACGTCGTCG ATACCCCGAG GCCTTGGCCC    25080
CGCCACGAAG ATGGCAGTCC CCGCCGCGCC GGCATCTCCG CCTTCGGATT CTCGGGCACC    25140
AACGCCCACG TCATCCTCGA AGAGGCTCCC GCCGCCCTGC CGGCCGAGCC CGCCACCTCA    25200
CAGCCGGCGT CGCAAGCCGC TCCCGCGGCG TGGCCCGTGC TCCTGTCGGC CAGGAGCGAG    25260
GCCGCCGTCC GCGCCCAGGC GAAGCGGCTC CGCGACCACC TCGTCGCCCA CGACGACCTC    25320
ACCCTCGCGG ATGTGGCCTA TTCGCTGGCC ACCACCGCG CCCACTTCGA GCACCGCGCC     25380
GCTCTCGTAG CCCACAACCG CGACGAGCTC CTCTCCGCGC TCGACTCGCT CGCCCAGGAC    25440
AAGCCCGCCC CGAGCACCGT CCTCGGACGG AGCGGAAGCC ACGGCAAGCT CGTCTTCGTC    25500
TTTCCTGGGC AAGGCTCGCA GTGGGAAGGG ATGGCCCTCT CGCTGCTCGA CTCCTCGCCC    25560
GTCTTCCGCG CTCAGCTCGA AGCATGCGAG CGCGCGCTCG CTCCTCACGT CGAGTGGAGC    25620
CTGCTCGCCG TCCTGCGCCG CGACGAGGGC GCCCCCTCCC TCGACCGCGT CGACGTCGTA    25680
CAGCCCGCCC TCTTTGCCGT CATGGTCTCC CTGGCGGCCC TCTGGCGCTC GCTCGGCGTA    25740
GAGCCCGCCG CCGTCGTCGG CCACAGTCAG GGCGAGATCG CCGCCGCCTT CGTCGCAGGC    25800
GCTCTCTCCC TCGAGGACGC GGCCCGCATC GCCGCCCTGC GCAGCAAAGC GCTCACCACC    25860
GTCGCCGGCA ACGGGGCCAT GGCCGCCGTC GAGCTCGGCG CCTCCGACCT CCAGACCTAC    25920
CTCGCTCCCT GGGGCGACAG GCTCTCCATC GCCGCCGTCA ACAGCCCCAG GGCCACGCTC    25980
GTGTCCGGCG AGCCCGCCGC CATCGACGCG CTGATCGACT CGCTCACCGC AGCGCAGGTC    26040
TTCGCCCGAA AAGTCCGCGT CGACTACGCC TCCCACTCCG CCCAGATGGA CGCCGTCCAA    26100
GACGAGCTCG CCGCAGGTCT AGCCAACATC GCTCCTCGGA CGTGCGAGCT CCCTCTTTAT    26160
TCGACCGTCA CCGGCACCAG GCTCGACGGC TCCGAGCTCG ACGGCGCGTA CTGGTATCGA    26220
AACCTCCGGC AAACCGTCCT GTTCTCGAGC GCGACCGAGC GGCTCCTCGA CGATGGGCAT    26280
CGCTTCTTCG TCGAGGTCAG CCCCCATCCC GTGCTCACGC TCGCCCTCCG CGAGACCTGC    26340
GAGCGCTCAC CGCTCGATCC CGTCGTCGTC GGCTCCATTC GACGCGACGA AGGCCACCTC    26400
```

```
GCCCGCCTGC TCCTCTCCTG GGCGGAGCTC TCTACCCGAG GCCTCGCGCT CGACTGGAAC    26460
GCCTTCTTCG CGCCCTTCGC TCCCCGCAAG GTCTCCCTCC CCACCTACCC CTTCCAACGC    26520
GAGCGCTTCT GGCTCGACGC CTCCACGGCG CACGCTGCCG ACGTCGCCTC CGCAGGCCTG    26580
ACCTCGGCCG ACCACCCGCT GCTCGGCGCC GCCGTCGCCC TCGCCGACCG CGATGGCTTT    26640
GTCTTCACAG GACGGCTCTC CCTCGCAGAG CACCCGTGGC TCGAAGACCA CGTCGTCTTC    26700
GGCATACCCT GTCCTGCCAG GCGCCGCCTC CTCGAGCTCG CCCTGCATGT CGCCCATCTC    26760
GTCGGCCTCG ACACCGTCGA AGACGTCACG CTCGACCCCC CCCTCGCTCT CCCATCGCAG    26820
GGCGCCGTCC TCCTCCAGAT CTCCGTCGGG CCCGCGGACG GTGCTGGACG AAGGGCGCTC    26880
TCCGTTCATA GCCGGCGCCA CGACGCGCTT CAGGATGGCC CCTGGACTCG CCACGCCAGC    26940
GGCTCTCTCG CGCAAGCTAG CCCGTCCCAT TGCCTTCGAT GCTCCGCGAA TGGCCCCCCC    27000
TCGGGCGCCA CCCAGGTGGA CACCCAAGGT TTCTACGCAG CCCTCGAGAG CGCTGGGCTT    27060
GCTTATGGCC CCGAGTTCCA GGGCCTCCGC CGCCGTCTAC AAGCGCGGCG ACGAGCTCTT    27120
CGCCGAAGCC AAGCTCCCGG ACGCCGCCGA AGAGGACGCC GCTCGTTTTG CCCTCCACCC    27180
CGCCCTGCTC GACAGCGCCT TGCAGGCGCT CGCCTTTGTA GACGACCAGG CAAAGGCCTT    27240
CAGGATGCCC TTCTCGTGGA GCGGAGTATC GCTGCGCTCC GGTCGGAGCC ACCACCCTGC    27300
GCGTGCGTTT CCACCGTCCT GAGGGCGAAT CCTCGCGCTC GCTCCTCCTC GCCGACGCCA    27360
GAGGCGAACC CATCGCCTCG GTGCAAGCGC TCGCCATGCG CGCCGCGTCC GCCGAGCAGC    27420
TCCGCAGACC CGGGAGCGTC CCACCTCGAT GCCCTCTTCC GCATCGACTG GAGCGAGCTG    27480
CAAAGCCCCA CCTCACCGCC CATCGCCCCG AGCGGTGCCC TCCTCGGCAC AGAAGGTCTC    27540
GACCTCGGGA CCAGGGTGCC TCTCGACCGC TATACCGACC TTGCTGCTCT ACGCAGCGCC    27600
CTCGACCAGG GCGCTTCGCC TCCAAGCCTC GTCATCGCCC CCTTCATCGC TCTGCCCGAA    27660
GGCGACCTCA TCGCGAGCGC CCGCGAGACC ACCGCGCACG CGCTCGCCCT CTTGCAAGCC    27720
TGGCTCGCCG ACGAGCGCCT CGCCTCCTCG CGCCTCGCCC TCGTCACCCG ACGCGCCGTC    27780
GCCACCCACG CTGAAGAAGA CGTCAAGGGC CTCGCTCACG CGCCTCTCTG GGGTCTCGCT    27840
CGCTCCGCGC AGAGCGAGCA CCCAGAGCGC CCTCTCGTCC TCGTCGACCT CGACGACAGC    27900
GAGGCCTCCC AGCACGCCCT GCTCGGCGCG CTCGACGCAA GAGAGCCAGA GATCGCCCTC    27960
CGCAACGGCA AACCCCTCGT TCCAAGGCTC TCACGCCTGC CCCAGGCGCC CACGGACACA    28020
GCGTCCCCCG CAGGCCTCGG AGGCACCGTC CTCATCACGG GAGGCACCGG CACGCTCGGC    28080
GCCCTGGTCG CGCGCCGCCT CGTCGTAAAC CACGACGCCA AGCACCTGCT CCTCACCTCG    28140
CGCCAGGGCG CGAGCGCTCC GGGTGCTGAT GTCTTGCGAA GCGAGCTCGA AGCTCTGGGG    28200
GCTTCGGTCA CCCTCGCCGC GTGCGACGTG GCCGATCCAC GCGCTCTAAA GGACCTTCTG    28260
GATAACATTC CGAGCGCTCA CCCGGTCGCC GCCGTCGTGC ATGCCGCCAG CGTCCTCGAC    28320
GGCGATCTGC TCGGCGCCAT GAGCCTCGAG CGGATCGACC GCGTCTTCGC CCCCAAGATC    28380
GATGCCGCCT GGCACTTGCA TCAGCTCACC CAAGATAAGC CCCTTGCCGC CTTCATCCTC    28440
TTCTCGTCCG TCGCCGGCGT CCTCGGCAGC TCAGGTCACT CCAACTACGC CGCTGCGAGC    28500
GCCTTCCTCG ATGCGCTTGC GCACCACCGG CGCGCGCAAG GGCTCCCTGC CTCATCGCTC    28560
GCGTGGAGCC ACTGGGCCGA GCGCAGCGCA ATGACAGAGC ACGTCAGCGC CGCCGGCGCC    28620
CCTCGCATGG AGCGCGCCGG CCTTCCCTCG ACCTCTGAGG AGAGGCTCGC CCTCTTCGAT    28680
GCGGCGCTCT TCCGAACCGA GACCGCCCTG GTCCCCGCGC GCTTCGACTT GAGCGCGCTC    28740
AGGGCGAACG CCGGCAGCGT CCCCCCGTTG TTCCAACGTC TCGTCCGCGC TCGCACCGTA    28800
```

```
CGCAAGGCCG  CCAGCAACAC  CGCCCAGGCC  TCGTCGCTTA  CAGAGCGCCT  CTCAGCCCTC    28860

CCGCCCGCCG  AACGCGAGCG  TGCCCTGCTC  GATCTCATCC  GCACCGAAGC  CGCCGCCGTC    28920

CTCGGCCTCG  CCTCCTTCGA  ATCGCTCGAT  CCCGATCG                              28958
```

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:5:

```
AATTCTAAAG  CATGCCGATC  GG                                                    22
```

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:6:

```
AATTCCGATC  GGCATGCTTT  A                                                     21
```

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:7:

```
AATTCTAAAC  CATGGCGATC  GG                                                    22
```

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:8:

```
AATTCCGATC  GCCATGGTTT  A                                                     21
```

( 2 ) INFORMATION FOR SEQ ID NO:9:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
         ( A ) DESCRIPTION: /desc ="oligonucleotide"

( x i ) SEQUENCE DESCRIPTION: SEQ ID NO:9:

CCAGCTGGAA TTCCG                                                                    15

( 2 ) INFORMATION FOR SEQ ID NO:10:

( i ) SEQUENCE CHARACTERISTICS:
         ( A ) LENGTH: 19 base pairs
         ( B ) TYPE: nucleic acid
         ( C ) STRANDEDNESS: single
         ( D ) TOPOLOGY: linear ( i i ) MOLECULE TYPE: other nucleic acid
         ( A ) DESCRIPTION: /desc ="oligonucleotide"

( x i ) SEQUENCE DESCRIPTION: SEQ ID NO:10:

CGGAATTCCA GCTGGCATG                                                                19

What is claimed is:

1. An isolated DNA molecule from the genome of *Sorangium cellulosum* encoding at least one polypeptide necessary for the biosynthesis of a soraphen, wherein said DNA molecule comprises at least one of the following: sorA Mod 1, sorA Mod 2, sorA Mod 3, sorB Mod 1, sorB Mod 2, sorB Mod 3, sorB Mod 4, and sorb Mod 5.

2. The isolated DNA molecule of claim 1, wherein said DNA molecule has the sequence of SEQ ID NO:1.

3. The isolated DNA molecule of claim 1, wherein said DNA molecule comprises all of the following: sorA Mod 1, sorA Mod 2, sorA Mod 3, sorB Mod 1, sorB Mod 2, sorB Mod 3, sorB Mod 4, and sorb Mod 5.

4. The isolated DNA molecule of claim 1, wherein said DNA molecule comprises sorA Mod 1.

5. The isolated DNA molecule of claim 4, wherein sorA Mod 1 comprises nucleotides 942–7115 of SEQ ID NO:1.

6. The isolated DNA moluculc of claim 1, wherein said DNA molecule comprises sorA Mod 2.

7. The isolated DNA molecule of claim 6, wherein sorA Mod 2 comprises nucleotides 7203–12884 of SEQ ID NO:1.

8. The isolated DNA molecule of claim 1, wherein said DNA molecule comprises sorA Mod 3.

9. The isolated DNA molecule of claim 8, wherein sofa Mod 3 comprises nucleotides 13455–19616 of SEQ ID NO:1.

10. The isolated DNA molecule of claim 1, wherein said DNA molecule comprises sorB Mod 1.

11. The isolated DNA molecule of claim 10, wherein sorB Mod 1 comprises nucleotides 19870–24556 of SEQ ID NO:1.

12. The isolated DNA molecule of claim 1, wherein said DNA molecule comprises sorB Mod 2.

13. The isolated DNA molecule of claim 12, wherein sorB Mod 2 comprises nucleotides 24638–30820 of SEQ ID NO:1.

14. The isolated DNA molecule of claim 1, wherein said DNA molecule comprises sorB Mod 3.

15. The isolated DNA molecule of claim 14, wherein sorB Mod 3 comprises nucleotides 30881–35446 of SEQ ID NO:1.

16. The isolated DNA molecule of claim 1, wherein said DNA molecule comprises sorB Mod 4.

17. The isolated DNA molecule of claim 16, wherein sorB Mod 4 comprises nucleotides 35528–40114 of SEQ ID NO:1.

18. The isolated DNA molecule of claim 1, wherein said DNA molecule comprises sorB Mod 5.

19. The isolated DNA molecule of claim 18, wherein sorB Mod 5 comprises nucleotides 40190–46318 of SEQ ID NO:1.

20. A chimeric gene comprising a heterologous promoter operatively linked to the DNA molecule of claim 1.

21. The chimeric gene of claim 20, wherein said promoter is a constitutive promoter.

22. The chimeric gene of claim 20, wherein said promoter is a chemically inducible promoter.

23. A vector comprising the DNA molecule of claim 1.

24. A host cell transformed with the vector of claim 23.

25. The host cell of claim 24, which is a bacteria.

26. The host cell of claim 24, which is a fungus.

27. The host cell of claim 24, which is a plant.

28. A cosmid clone designated pJL3 and deposited as NRRL B-21254.

29. A cosmid clone designated pVKM 15 and deposited as NRRL B-21651.

* * * * *